United States Patent
Ralph

(10) Patent No.: US 10,953,045 B2
(45) Date of Patent: Mar. 23, 2021

(54) AGENTS AND COMPOSITIONS FOR ELICITING AN IMMUNE RESPONSE

(71) Applicant: Cancure Limited, Surfers Paradise (AU)

(72) Inventor: Stephen Ralph, Mermaid Waters (AU)

(73) Assignee: CANCURE LIMITED, Surfers Paradise (AU)

( * ) Notice: Subject to any disclaimer, the term of this patent is extended or adjusted under 35 U.S.C. 154(b) by 444 days.

(21) Appl. No.: 15/563,815

(22) PCT Filed: Apr. 1, 2016

(86) PCT No.: PCT/AU2016/050250
§ 371 (c)(1),
(2) Date: Oct. 2, 2017

(87) PCT Pub. No.: WO2016/154684
PCT Pub. Date: Oct. 6, 2016

(65) Prior Publication Data
US 2018/0360879 A1 Dec. 20, 2018

(30) Foreign Application Priority Data
Apr. 2, 2015 (AU) .............................. 2015901218

(51) Int. Cl.
*A61K 35/17* (2015.01)
*C07K 14/705* (2006.01)
*A61K 39/00* (2006.01)
*A61P 35/00* (2006.01)
*A61P 27/00* (2006.01)

(52) U.S. Cl.
CPC .............. *A61K 35/17* (2013.01); *A61K 39/00* (2013.01); *A61P 27/00* (2018.01); *A61P 35/00* (2018.01); *C07K 14/70532* (2013.01); *C07K 14/70575* (2013.01); *A61K 2039/5152* (2013.01); *A61K 2039/5154* (2013.01); *A61K 2039/5256* (2013.01); *A61K 2039/545* (2013.01); *A61K 2039/55522* (2013.01); *A61K 2039/572* (2013.01); *C12N 2501/24* (2013.01); *C12N 2510/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2004/0161806 A1* | 8/2004 | Tykocinski | A61K 39/0011 435/7.21 |
| 2004/0209363 A1* | 10/2004 | Watts | C12N 5/0636 435/455 |
| 2004/0235156 A1 | 11/2004 | Ralph | |
| 2005/0002916 A1* | 1/2005 | Jooss | A61K 38/193 424/93.21 |
| 2006/0034810 A1* | 2/2006 | Riley | A61K 39/21 424/93.21 |
| 2010/0240585 A1* | 9/2010 | Shirwan | C07K 14/70532 514/3.7 |
| 2012/0225043 A1* | 9/2012 | Chen | A61K 39/0011 424/93.71 |
| 2016/0250322 A1* | 9/2016 | Schreiber | C07K 14/70575 424/172.1 |

FOREIGN PATENT DOCUMENTS

WO    WO 2001/088097 A1    11/2001
WO    WO 2005/118788 A2    12/2015

OTHER PUBLICATIONS

Kitada et al. (1999) British Journal of Haematology, 1999, 106: 995-1004.*
Gershan et al. Journal for ImmunoTherapy of Cancer 2013, 1(Suppl 1): p. 74 (one page).*
Iinuma et al. (1998) Biotherapy 12 (12): 1559-1565 (in Japanese, with an English Abstract).*
Luster et al. Mol Cancer Ther 2015; 14(12 Suppl 2): Abstract A69 (5 pages).*
Hiroishi et al. Gene Therapy (1999) 6: 1988-1994.*
Jollow et al. (1999) Transplantation 68(3): 430-439.*
Niemann-Masanek et al. (2002) Nephron 92(3): 542-556.*
Mangsbo et al. (2015) Clin Cancer Res; 21(5): 1115-1126.*
Dezfouli, S., et al., Enhancing CTL responses to melanoma cell vaccines in vivo: synergistic increases obtained using IFN gamma primed and IFNbeta treated B 7-1+ B16-F10 melanoma cells, Immunology and Cell Biology, vol. 81, pp. 459-471, 2003.
Habib-Agahi, M., et al., Preferential T cell expansion by artificial antigen presenting cells expressing 4-1BBL alone or in combination with CD80 or CD86, Iranian Journal of Immunology, vol. 5, pp. 136-147, 2008.
Macatonia, S.E., et al., Dendritic cell infection, depletion and dysfunction in HIV-infected individuals, Immunology, vol. 71, pp. 38-45, 1990.
Powell, K.L., et al., Development of a potent melanoma vaccine capable of stimulating CD8(+) T-cells independently of dendritic cells in a mouse model, Cancer Immunology and Immunotherapy, vol. 64, pp. 861-872, 2015.
Sturmhoefel, K., et al., Potent activity of soluble B7-IgG fusion proteins in therapy of established tumors and as vaccine adjuvant, Cancer Research, vol. 59, pp. 4964-4972, 1999.
Yan, X., et al., Induction of a VLA-2 (CD49b )—expressing effector T cell population by a cell-based neuroblastoma vaccine expressing CD137L, Journal of Immunology, vol. 181, pp. 4621-4631, 2008.
International Search Report, dated Jun. 28, 2016, in International Application No. PCT/AU2016/050250.

(Continued)

*Primary Examiner* — Ilia I Ouspenski
(74) *Attorney, Agent, or Firm* — Knobbe, Martens, Olson & Bear LLP

(57) ABSTRACT

Immune-potentiating compositions include cells exhibiting enhanced antigen-presenting functions. The compositions are generally useful in facilitating the stimulation of host immune cell responses, including selective and targeted immune cell responses, and are particularly useful in the treatment and/or prophylaxis of cancers, tumors and pathogenic infections.

21 Claims, 29 Drawing Sheets

Specification includes a Sequence Listing.

(56) References Cited

OTHER PUBLICATIONS

Search Information Statement (SIS), dated Jun. 28, 2016, in International Application No. PCT/AU2016/050250.
Guinn, B.-a., et al., 4-1BBL Cooperates with B7-1 and B7-2 in Converting a B Cell Lymphoma Cell Line into a Long-Lasting Anti-Tumor Vaccine, The Journal of Immunology, vol. 162, No. 8, pp. 5003-5010, 1999.
Lu, Z.-Y., et al., B7-1 and 4-1BB ligand expression on a myeloma cell lines makes it opposable to expand autologous tumor-specific cytotoxic T cells in vitro, *Experimental Hematology*, vol. 35, No. 3, pp. 443-453, 2007.

\* cited by examiner

AGENTS AND COMPOSITIONS FOR ELICITING AN IMMUNE RESPONSE

PRIORITY AND CROSS REFERENCE TO RELATED APPLICATIONS

This application is the U.S. National Phase Application under 35 U.S.C. § 371 of International Application No. PCT/AU2016/050250, filed Apr. 1, 2016, designating the U.S. and published in English as WO 2016/154684 A1 on Oct. 6, 2016, which claims the benefit of Australian Patent Application No. AU 2015901218, filed Apr. 2, 2015. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled DAVI549001APCSEQLIST.txt, created and last saved on Feb. 27, 2018, which is 15,149 bytes in size. The information in the Electronic Sequence Listing is incorporated herein by reference in its entirety in accordance with 35 U.S.C. § 1.52(e).

FIELD OF THE INVENTION

This invention relates generally to immune potentiating compositions. More particularly, the present invention is directed to compositions comprising cells exhibiting enhanced antigen-presenting functions. The compositions of the present invention are generally useful in facilitating the stimulation of host immune cell responses, including selective and targeted immune cell responses and are particularly useful in the treatment and/or prophylaxis of cancers, tumors, and pathogenic infections.

BACKGROUND OF THE INVENTION

Cancer remains as one of the leading causes of morbidity and mortality worldwide with malignant melanoma being one type that significantly contributes to these statistics (Trotter et al., 2014; Bray et al., 2012). It is partly due to this sizeable global burden that research into cancer is so prolific (Trotter et al., 2014; Jemal et al., 2011). A plethora of research investigating the pathogenesis, molecular mechanisms and potential treatment options of malignant melanoma has been undertaken (Lee et al., 2014; Yang, 2011; and Fang et al., 2008). However, despite the amount of research that has been conducted, there is still no vaccine that has been approved for use in preventing or treating malignant melanoma.

One methodology for targeting a vaccine to specific cancers relies on using a patient's own cells, either melanoma cells and/or dendritic cells, to generate customized vaccines in order to boost the immune response of the patient against their own cancer cells. This technology has been adopted and tested in several studies (Berd et al., 1997; Soiffer et al., 2003; O'Rourke et al., 2003; de Rosa et al., 2014). However, a concern with personalized therapies, including treatments based on autologous cancer cell and/or dendritic cell vaccines, is the highly time-consuming nature of the process and the substantial costs of manufacture. These two characteristics represent significant impediments for the timely and cost effective production of personalized cancer vaccines and may explain the disinterest of pharmaceutical companies to proactively engage in the development of such therapeutics (Jaffee et al., 2001; Sondak et al., 2006; Ralph 2007). A related technology that might be more commercially viable is the use of allogeneic whole cell based vaccines. These vaccines are based on allogeneic tissue with favourable immunogenic properties, and are increasing in popularity and recent research has provided useful information about the relationship between cancer and patients' immune responses (Dezfouli et al., 2003; Fang, 2008).

The most successful whole cell vaccine to date has been CANVAXIN™, which was comprised of three irradiated, allogeneic melanoma cell lines that between them expressed over 20 different melanoma antigens (Hsueh and Morton, 2003). Although this vaccine reached Phase III clinical testing, the trial was halted after the Data Safety Monitoring Board determined that CANVAXIN™ treated patients were unlikely to show any survival benefit compared to the unvaccinated control patients (Sondak et al., 2006). However, this trial provided a useful methodology for vaccine development, which has been utilised in studies since (Faries et al., 2009; Lotem et al., 2011). A separate study by Dezfouli et al. (2003) identified that engineering melanoma cells to express B7.1 on the cell surface and subsequently treating with a combination of IFNγ/β not only enhanced B7.1 expression, but also induced specific cytotoxic T lymphocyte responses to melanoma cells. Furthermore, this study concluded that the addition of B7.1 onto the melanoma vaccine mediated the observed CD8$^+$ T cell responses independently of CD4$^+$ helper T cells (Dezfouli et al., 2003).

SUMMARY OF THE INVENTION

The present inventors have surprisingly discovered that a stronger immune response to a target antigen can be elicited by vaccination with an antigen-presenting cell having a B7 molecule and a 4-1BB agonist presented on its surface, and whose antigen presenting properties have been enhanced by exposure to an interferon treatment. The combination of interferon treatment, and surface expression of B7 molecule and 4-1BB agonist produces a synergistic enhancement in antigen-presenting function of the cell which when introduced into a suitable host elicits a markedly improved immune response against antigens presented by that cell. The artificial antigen-presenting cell of the present invention has particular advantages in the treatment of subjects who have depleted natural antigen-presenting cell populations (e.g., macrophages, dendritic cells, etc.).

Thus, in one aspect of the present invention, there is provided an artificial antigen-presenting cell comprising a B7 molecule and a 4-1BB agonist on its surface, wherein the antigen-presenting function of the cell (e.g., a higher level of major histocompatability complex on the cell surface) is enhanced by exposure to at least one interferon (IFN). Suitably, the antigen-presenting function of the cell is enhanced by contacting the cell with (e.g., culturing in the presence of) at least one exogenous IFN.

In each of the aspects and embodiments described herein, the artificial antigen-presenting cell is generally derived from an animal cell, which is typically a vertebrate cell (e.g., a mammalian cell). Suitably, the animal cell is a cancer or tumor cell (e.g., a melanoma cell).

In each of the aspects and embodiments described herein, the 4-1BB agonist is suitably a 4-1BB ligand.

In another aspect of the present invention, a composition is provided, comprising a B7 molecule, a 4-1BB agonist and animal cells contacted with (e.g., culturing in the presence of) at least one exogenous IFN for a time and under conditions sufficient to enhance the antigen presenting function of the cells.

The B7 molecule can be present on the surface of the cells or in soluble form. Similarly, the 4-1BB agonist can be present on the surface of said cells or in soluble form. In illustrative examples of this type, one of the B7 molecule and 4-1BB agonist is present on the cell surface and the other is in soluble form. In other illustrative examples, the B7 molecule and 4-1BB agonist are each present on the surface of the cells. Alternatively, both the B7 molecule and 4-1BB agonist are in soluble form.

In each of the aspects and embodiments described herein, the animal cells are generally vertebrate cells, typically mammalian cells, non-limiting examples of which include cancer or tumor cells (e.g., melanoma cells).

In a further aspect of the present invention, there is provided a method for producing an artificial antigen presenting cell, the method comprising:

exposing animal cells expressing a B7 molecule and a 4-1BB agonist on their cell surface to at least one (typically exogenous) IFN for a time and under conditions sufficient to enhance the antigen presenting functions of the cells.

In still a further aspect of the present invention, there is provided a method for enhancing immunopotentiation of animal cells, the method comprising:

exposing animal cells expressing a B7 molecule and a 4-1BB agonist on their cell surface to at least one (typically exogenous) IFN for a time and under conditions sufficient to enhance the antigen presenting functions of the cells.

In some embodiments, the method further comprises isolating cells expressing one or both of the B7 molecule and the 4-1BB agonist from a heterogeneous population of animal cells.

In some embodiments, the method further comprises modifying the animal cells to express one or both of the B7 molecule on their cell surface. Suitably, the step of modification comprises introducing into the animal cells at least one polynucleotide from which one or both of the B7 molecule and the 4-1BB agonist are expressible.

In each of the aspects and embodiments described herein, exposure of the animal cells to the at least one IFN suitably comprises contacting the cells with (e.g., culturing in the presence of) a type II IFN for a time and under conditions sufficient to permit cellular responsiveness to at least one type I IFN and contacting the cells with the at least one type I IFN for a time and under conditions to enhance the antigen presenting function of the cells. The cells may be contacted sequentially or simultaneously with the type II IFN and the type I IFN. In illustrative examples of this type, the cells are first contacted with the type II IFN and subsequently contacted with a type II IFN. In other illustrative examples, the cells are contacted simultaneously with a type II IFN and a type I IFN.

Generally, the type II IFN is selected from an IFN-gamma or a biologically active fragment thereof.

The at least one type I IFN is generally selected from an IFN-alpha, an IFN-beta or biologically active fragments thereof.

In some embodiments of the methods broadly described above, the animal cells are rendered inactive or incapable of proliferation. For example, the animal cells may be irradiated with a suitable amount of radiation such as, for example, gamma-irradiation, as is known in the art, to render the animal cells incapable of proliferating in the intended host.

In yet another aspect, the invention provides a method for enhancing immunopotentiation of animal cells, comprising:

exposing the animal cells to at least one (typically exogenous) IFN for a time and under conditions sufficient to enhance the antigen presenting functions of the cells; and combining the cells so exposed with a B7 molecule and a 4-1BB agonist, wherein at least one of the B7 molecule and the 4-1BB agonist is in soluble form.

Another aspect of the present invention resides in a composition comprising a B7 molecule, a 4-1BB agonist, and animal cells contacted with (e.g., culturing in the presence of) an IFN-gamma (which is typically exogenous) and optionally one or both of a first type I IFN (which is typically exogenous) and a second type I IFN (which is typically exogenous) for a time and under conditions sufficient to enhance the antigen presenting function of the cells, wherein the first type I IFN is selected from an IFN-beta or a biologically active fragment thereof, and wherein the second type I interferon is selected an IFN-alpha or a biologically active fragment thereof. Suitably, at least one of the B7 molecule and the 4-1BB agonist is expressed on the surface of the animal cells or present in soluble form.

Another aspect of the present invention provides a composition for use in eliciting an immune response against a target antigen, wherein the composition comprises a B7 molecule, a 4-1BB agonist, and animal cells contacted with (e.g., cultured in the presence of) at least one (typically exogenous) IFN for a time and under conditions sufficient to enhance the antigen presenting functions of the cells, wherein an antigen corresponding to the target antigen is presented by the animal cells (e.g., for stimulation of the immune system).

In each of the aspects and embodiments described herein, the composition broadly described above may comprise any one or more of a pharmaceutically acceptable carrier, an adjuvant, a diluent or an ancillary therapeutic agent. Suitably, the ancillary therapeutic agent comprises an agent that targets rapidly dividing cells and/or disrupts the cell cycle.

In yet another aspect, the invention provides a method for treatment and/or prophylaxis of a disease or condition associated with enhanced or aberrant expression of a target antigen, comprising administering to a subject in need thereof an effective amount of a cell or composition as broadly described above. In some embodiments, the disease or condition is a cancer or tumor. In some embodiments, the subject is exposed to a medical treatment that targets rapidly dividing cells and/or disrupts the cell cycle. In some embodiments, the administered cell (whether naked or as part of a composition) is autologous, syngeneic, allogeneic or xenogeneic relative to the subject.

According to a further aspect, the invention provides a kit comprising a composition that comprises animal cells contacted with (e.g., cultured in the presence of) at least one (typically exogenous) IFN for a time and under conditions sufficient to enhance the antigen presenting function of said cells, together with a B7 molecule and an 4-1BBL agonist.

In yet another aspect of the present invention, a method is provided for treatment and/or prophylaxis of tumorigenesis, the method comprising administering to a patient in need thereof an effective amount of a cell or composition as broadly described above.

BRIEF DESCRIPTION OF THE FIGURES

An example of the present invention will now be described with reference to the accompanying drawings, in which:—

1BBL/IFNγ/β vaccinated mice were cultured in MLC for 5 days and then used for CTL assays. The target B16-F10/B7.1 cells were stained with DiI (red) and SYTOX Green was used to detect the percentage of dead cells. Bright field, green and red fluorescence images were recorded for various wells within the CTL assays that contained either 100% live targets alone (IFNγ/β treated B16-F10/B7.1 cells), 100% dead targets alone (IFNγ/β B16-F10/B7.1 cells treated with 0.4% NP9), 100% live effectors alone (lymphocytes) or effectors plus targets combined in a 10:1 ratio. Overlaid images are also included as shown.

Figure 16:
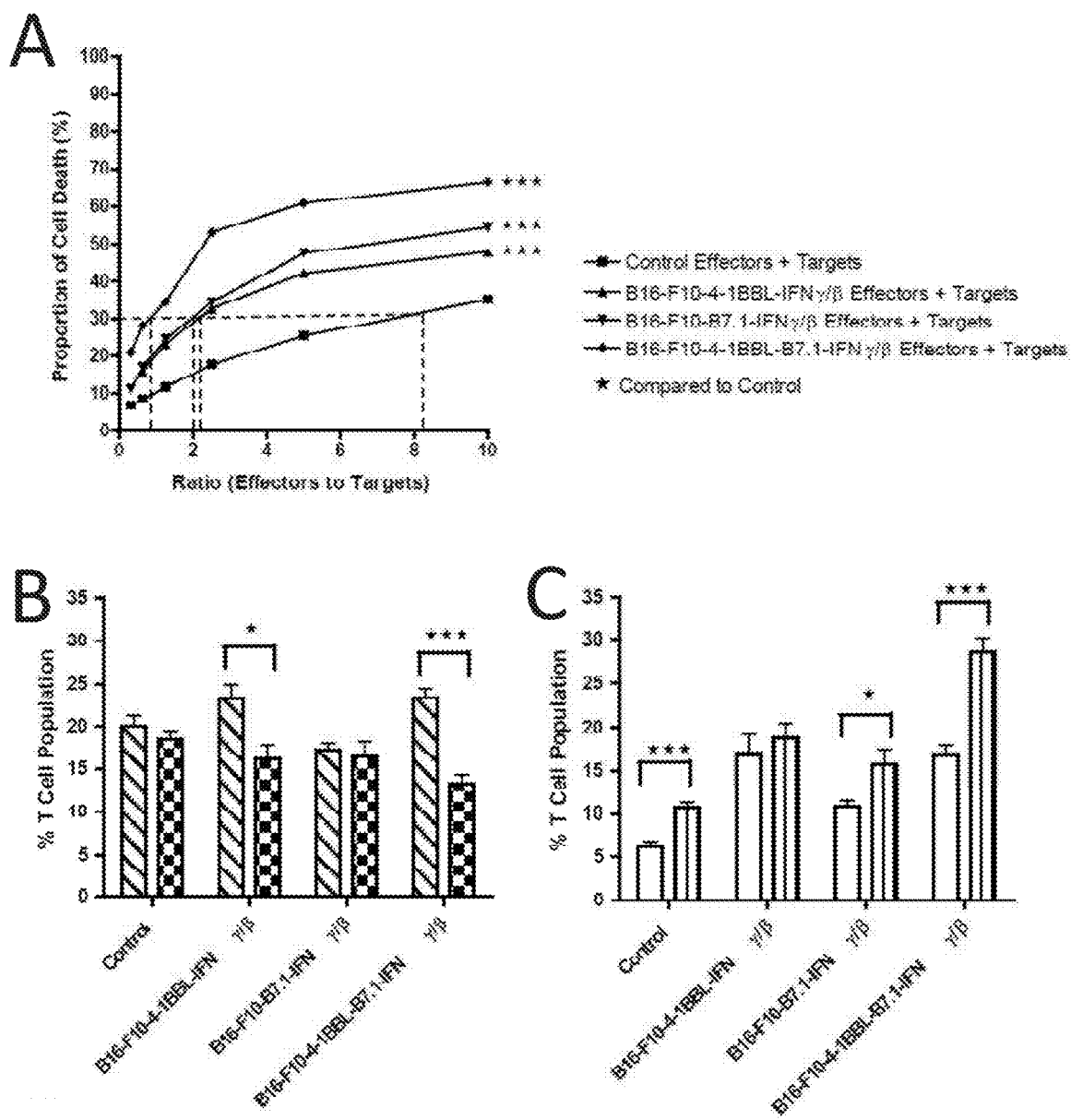

FIG. 16. (A) Cell death in CTL assays using MLC derived splenic lymphocytes in response to the B16-F10-4-1BBL-B7.1-IFNγ/β vaccine. Splenic lymphocytes from naïve control C57BL/6 mice or mice vaccinated with either B16-F10-4-1BBL-IFNγ/β, B16-F10-B7.1-IFNγ/β or B16-F10-4-1BBL-B7.1-IFNγ/β cells according to vaccination protocol 2 were purified and cultured as effectors (E) with B16-F10-B7.1-IFNγ/β antigenic stimulators in MLCs for five days. SYTOX Green nuclear uptake was used to detect cell death using a spectrophotometer with settings of an excitation wavelength of 485 nm and an emission wavelength of 525 nm. The ratios of the effector (E) to live cancer target cells (T) ranged from 0.3:1 up to 10:1 and the mean and standard error of the proportion of cell death for each ratio of E:T are plotted. The proportion of cell death was calculated and the data analysed using the general linear model. (B), (C) % $CD4^+$ but increased % $CD8^+$ T cells in MLC of splenic lymphocytes derived from mice vaccinated with B16-F10-4-1BBL-B7.1-IFNγ/β cells. C57BL/6 mice were either used as controls (n=21) or injected as shown using vaccination protocol 1 or 2 with either B16-F10/4-1BBL/IFNγ/β (n=15), B16-F10/B7.1/IFNγ/β (n=16) or B16-F10/4-1BBL/B7.1/IFNγ/β (n=18) vaccines. Spleens from control and vaccinated mice were harvested, lymphocytes isolated and expanded in MLCs containing a monolayer of inactivated IFNγ/β treated B16-F10/B7.1 cells. After five days in the MLCs, the mixed lymphocyte population was collected and analysed for changes in $CD4^+$ and $CD8^+$ T cells by flow cytometry. Data are representative of four independent experiments. The mean and SE are displayed and the data was analysed using independent-samples T tests. Diagonally striped bars: $CD4^+$ T cells (Protocol 1); Checkered bars: $CD4^+$ T cells (Protocol 2); Clear bars: $CD8^+$ T cells (Protocol 1); and Vertically striped bars: $CD8^+$ T cells (Protocol 2). The difference between the mean value is indicated in boxplots (B) and (C).

Figure 17:
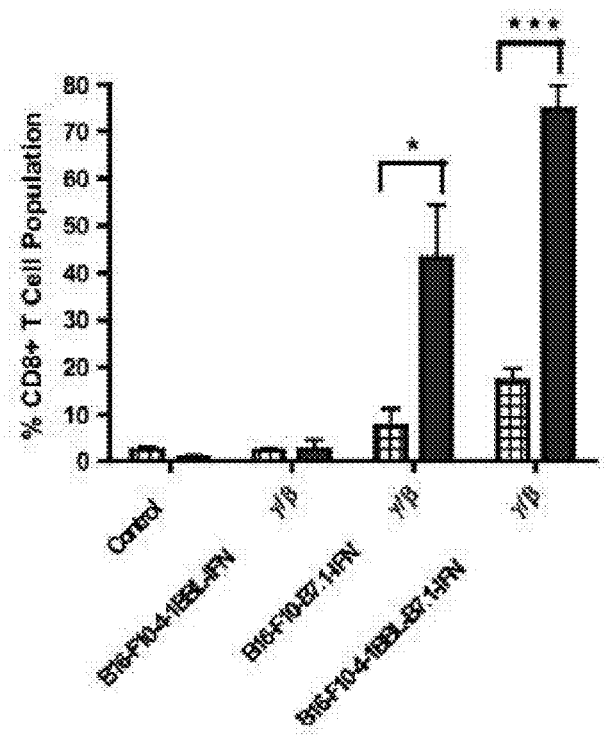
Figure 17:
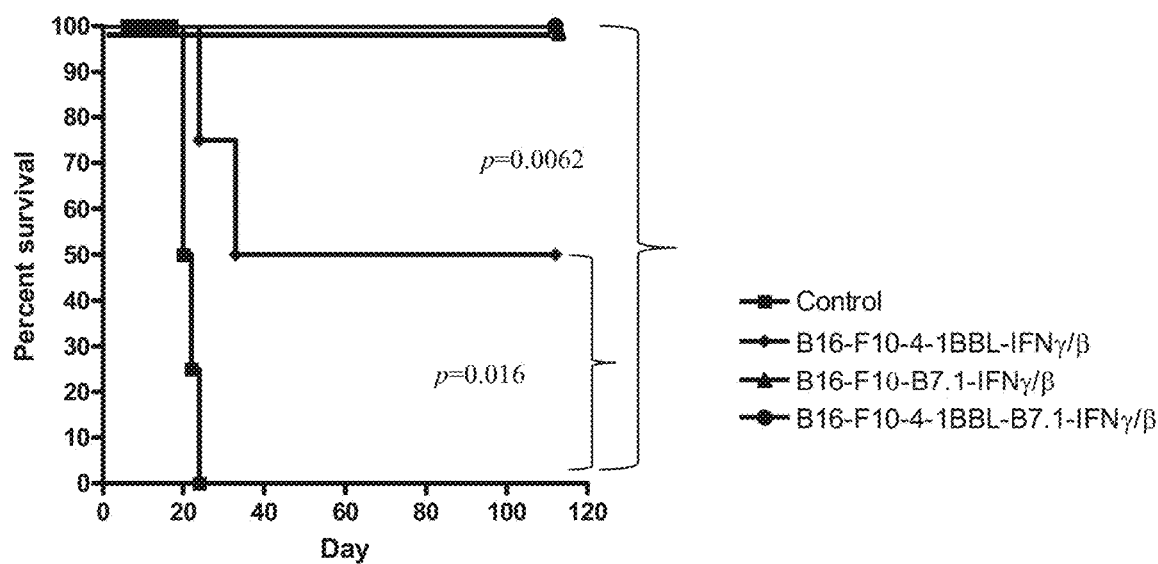

FIG. 17. (A) Activated $CD8^+$ T cell populations from splenic derived lymphocytes expanded in MLCs from mice treated with the B16-F10/4-1BBL/B7.1/IFNγ/β cell vaccine following Protocol 2. Lymphocytes from control mice or mice vaccinated with either B16-F10/4-1BBL/IFNγ/β, B16-F10/B7.1/IFNγ/β or B16-F10/4-1BBL/B7.1/IFNγ/β cells according to Protocol 1 or 2 were cultured in MLC for 5 days with a monolayer of B16-F10-B7.1-IFNγ/β cells as antigenic stimulators. Lymphocytes were then analysed for the expression of CD8 as well as the activation markers CD107a and IFNγ by flow cytometry. This data is representative of 4 independent experiments. The mean and SE are displayed and the differences between the groups were analysed by independent-sample T tests. (B) Mice vaccinations with the Protocol 1 prime/boost strategy of two vaccine doses significantly increases survival after challenge with $5\times10^5$ live B16-F10-B7.1 cells. C57BL/6 mice were either used as controls or injected intraperitoneally with two doses of either B16-F10/4-1BBL/IFNγ/β, B16-F10/-B7.1/IFNγ/β or B16-F10/4-1BBL/B7.1/IFNγ/β vaccines following vaccination Protocol 1 (n=4 per group). Four days following the final vaccination, all mice were subcutaneously injected with $5\times10^5$ live B16-F10/B7.1 cells on the rear left flank. Tumor growth was measured every two to three days using calipers and mice were euthanized when the tumor reached a maximum of 2.0 cm in length in any direction. This data is representative of a single experiment and survival was analysed using the Log rank test.

Figure 18:
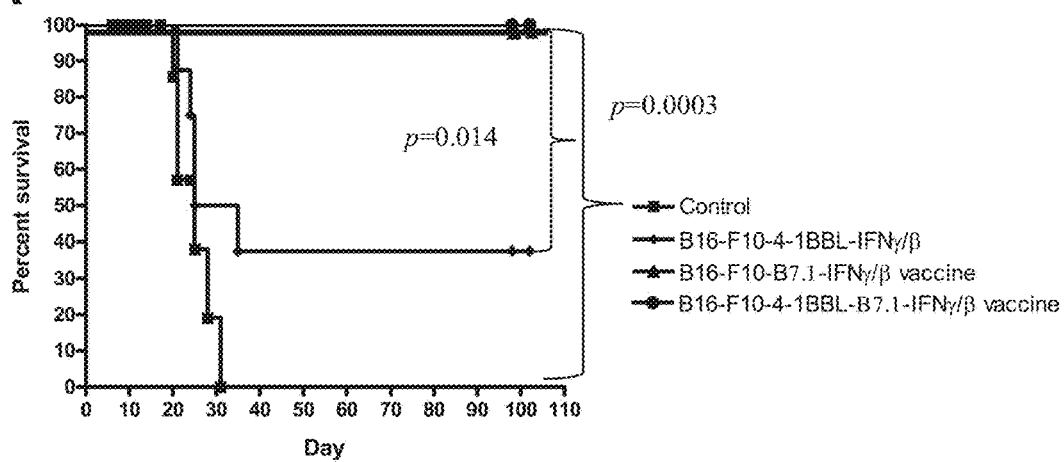
Figure 18:
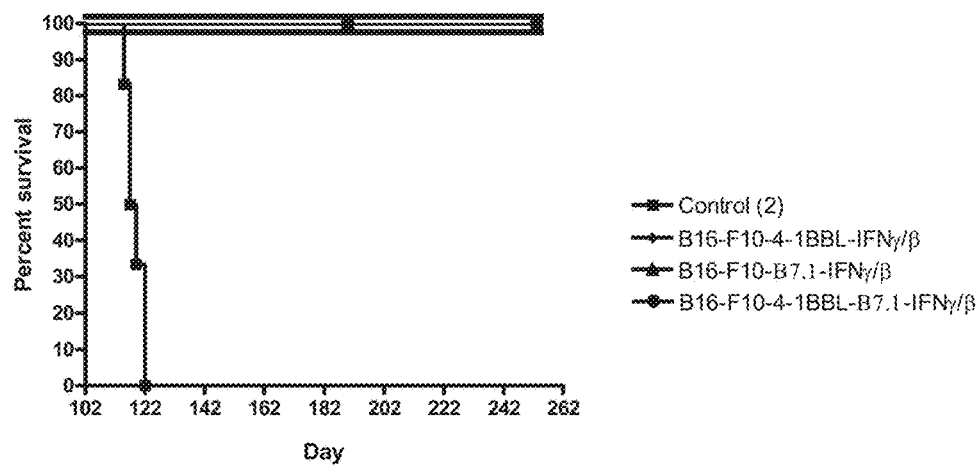
Figure 18:
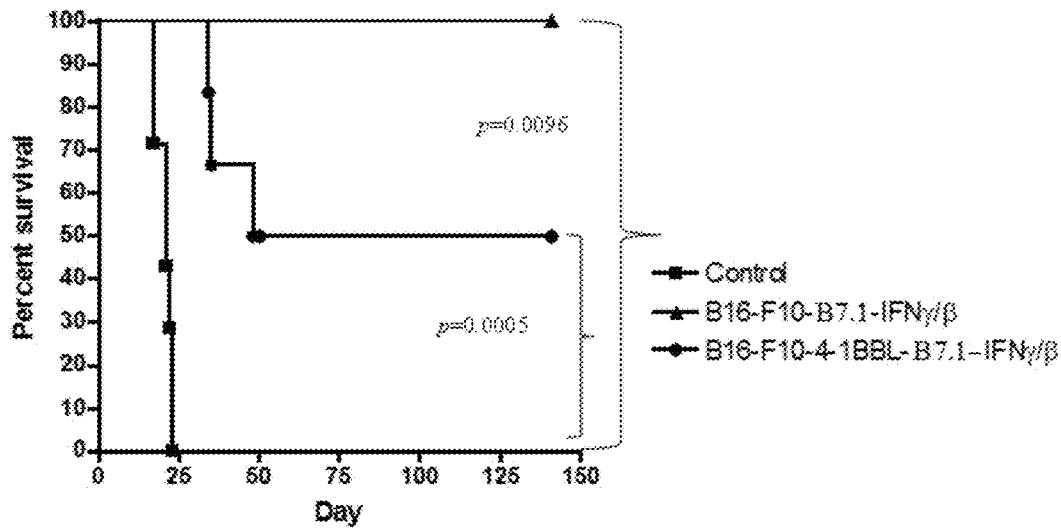

FIG. 18. Vaccinating mice with four doses of either the B16-F10/B7.1/IFNγ/β or B16-F10/4-1BBL/B7.1/IFNγ/β cells to assess tumor development upon challenge. C57BL/6 mice received four doses of either B16-F10/4-1BBL/IFNγ/β (n=6), B16-F10/B7.1/IFNγ/β (n=7) or B16-F10/4-1BBL/B7.1/IFNγ/β cell vaccines (n=7) according to Protocol 2 or remained unvaccinated (n=6) as controls. four days following the final vaccination, all mice were challenged by subcutaneous injection with $5\times10^5$ live B16-F10/B7.1 cells on the rear left flank. (A) Tumor growth was measured every 2 to 3 days using calipers and mice were euthanized when any dimension of the tumor reached a maximum of 2.0 cm in length. (B) The mice that survived the initial tumor challenge were further boosted with an additional two doses of vaccine on days 94 and 98 following the initial tumor challenge. The vaccinated mice and a separate group of naïve mice were challenged four days following the final booster injection with $5\times10^5$ live B16-F10/B7.1 cells (on day 102) and tumor growth was monitored every two to three days. This data is representative of two independent experiments and survival was analysed using the Log rank test. (C) C57BL/6 mice were either used as controls (n=7) or injected with four doses of either B16-F10/B7.1/IFNγ/β (n=3) or B16-F10/4-1BBL/B7.1/IFNγ/β cells (n=6). four days after the fourth and final vaccination, all mice received a live tumor challenge by subcutaneous injection with an increased tumor burden of $1\times10^6$ live B16-F10/B7.1 cells on the rear left flank. Tumor growth was measured as described for (A) and (B). Graph traces: ■Control; ◆B16-F10/4-1BBL/IFNγ/β; ▼B16-F10/B7.1/IFNγ/β; and ●B16-F10/4-1BBL/B7.1/IFNγ/β.

Figure 19:
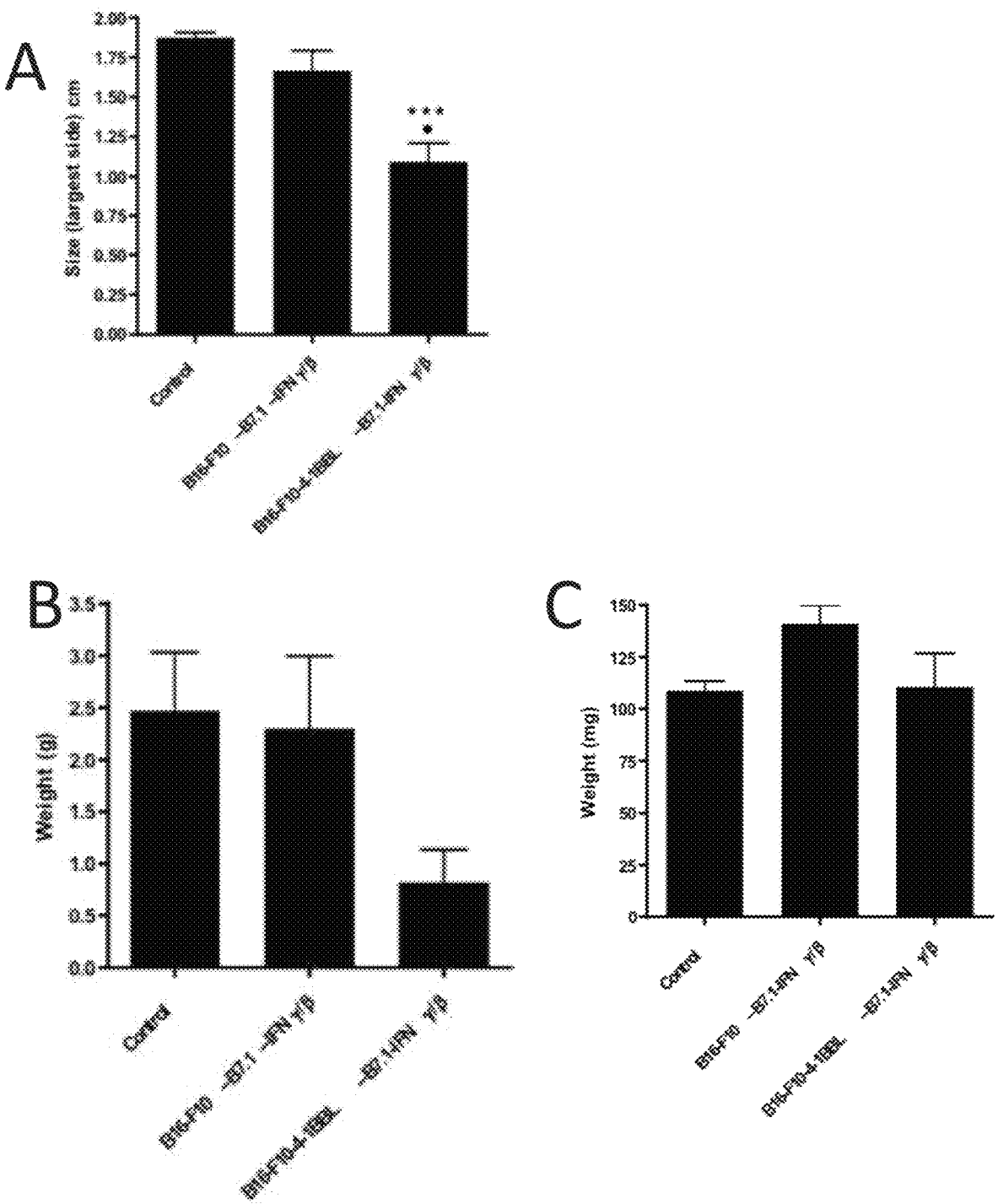

FIG. 19. Tumor growth in mice treated with four doses of the cell vaccines. C57BL/6 mice were either used as controls or were injected with four doses of either the B16-F10/B7.1/IFNγ/β or B16-F10/4-1BBL/B7.1/IFNγ/β whole cell vaccines. Four days after the final vaccination, all mice were challenged with a subcutaneous injection of $5\times10^5$ live wild type B16-F10 cells (n=3) on the rear left flank. (A) Tumor sizes were measured on day 17 and recorded before they were euthanized. Tumors (B) and spleens (C) were harvested the sacrificed mice and weighed. The mean±SE of the data is shown and One-way ANOVAs were performed to compare the weight of tumors and spleens between groups. The results are shown as the mean±SE and one-way ANOVA was performed to compare the size of the tumors.

Figure 20:
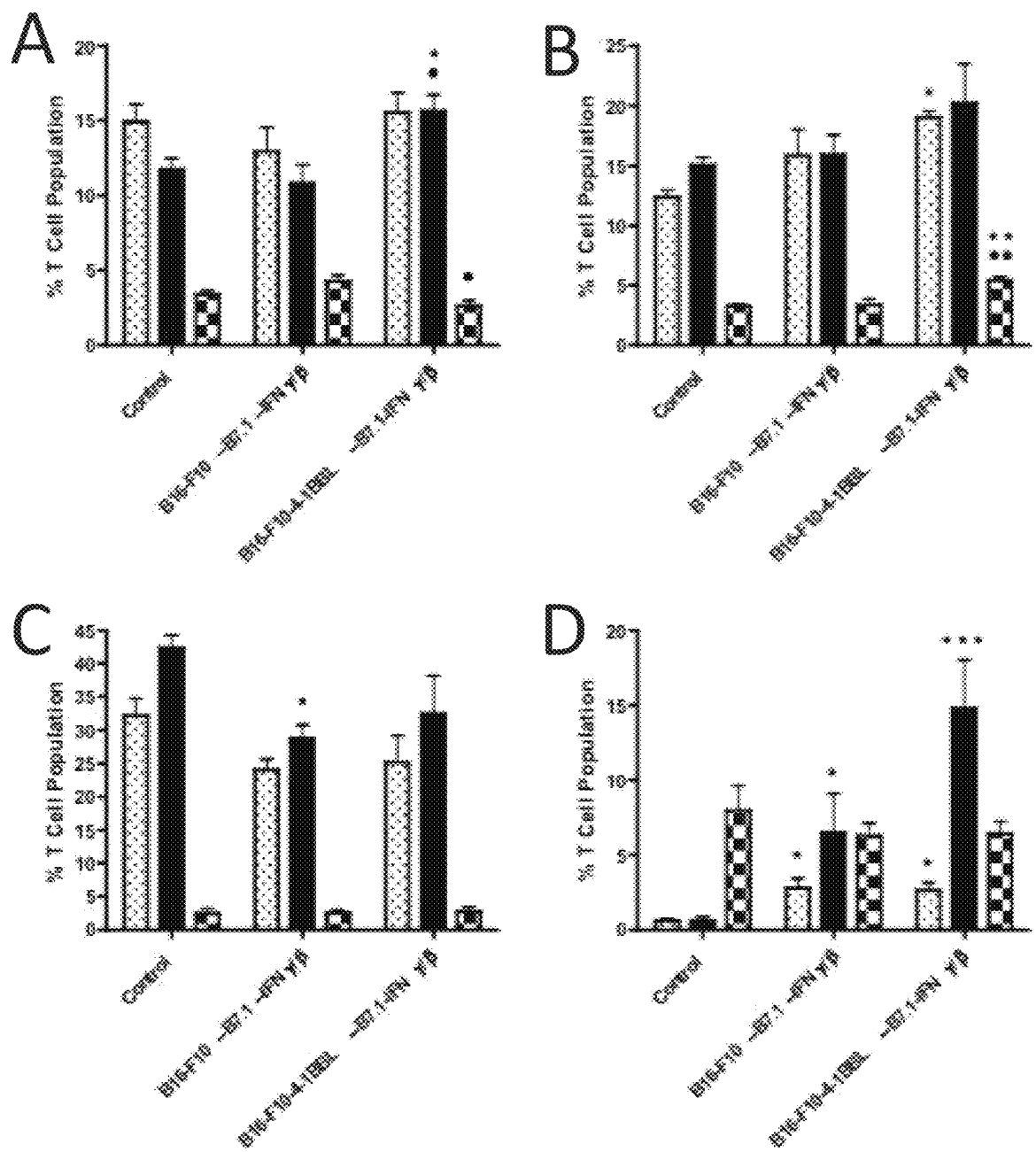

FIG. 20. $CD8^+$ T cells populations in spleen, tumors, blood and lymph nodes in mice receiving vaccine doses before challenge with live B16-F10 cells. C57BL/6 mice were used as controls or were vaccinated with four doses of either the B16-F10/B7.1/IFNγ/β or B16-F10/4-1BBL/B7.1/IFNγ/β cell vaccines. All mice were subcutaneously challenged with $5\times10^5$ live B16-F10 cells and were sacrificed at day 17 post challenge. Spleens (A), blood (B), lymph nodes (C) and tumors (D) were collected from all of the mice and then processed to purify the lymphocytes. The cell samples were then analysed for the % $CD4^+$, $CD8^+$ and regulatory T cell populations by flow cytometry. The mean and SE is shown.

Figure 21:
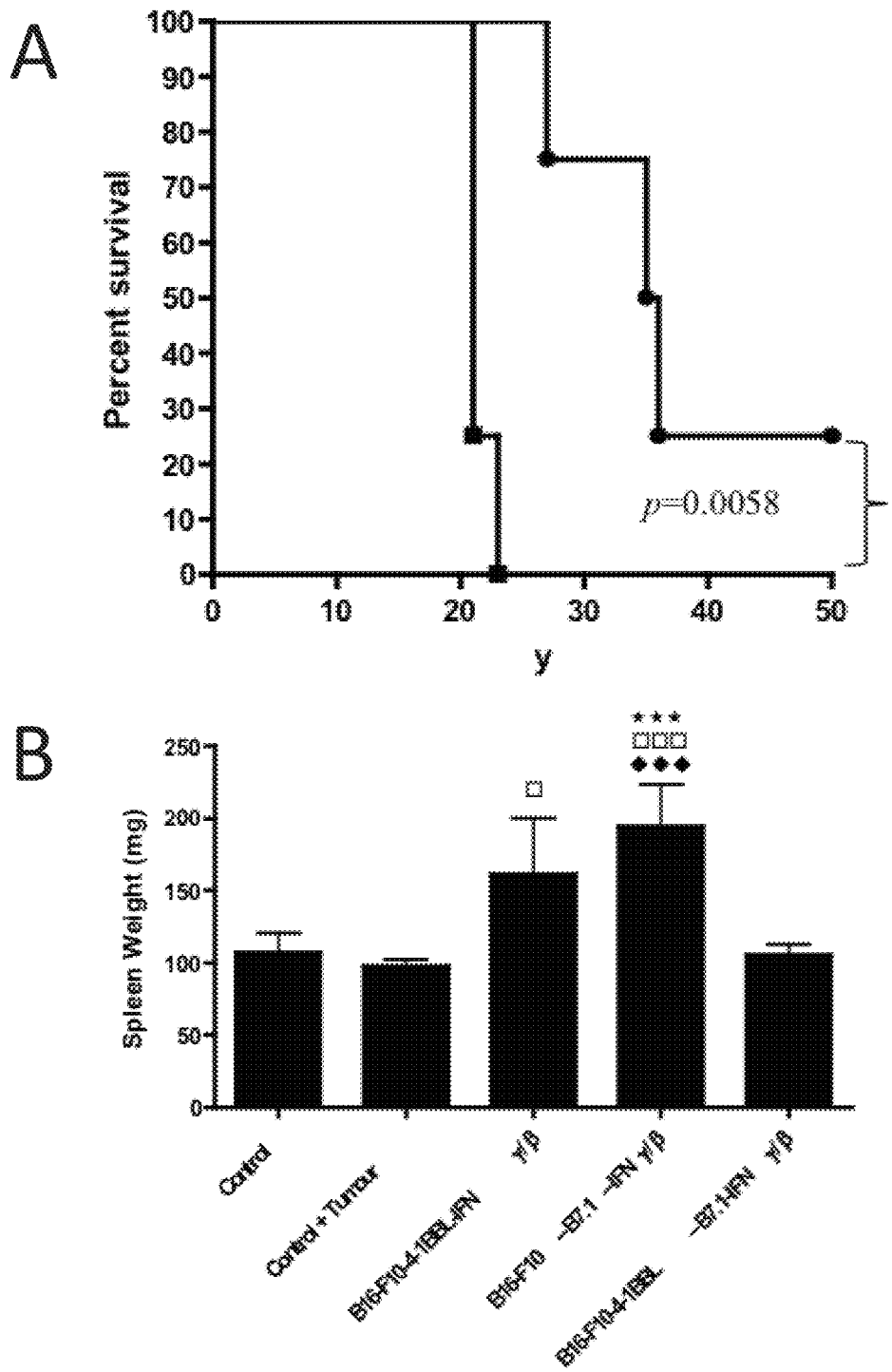

FIG. 21. Survival of mice receiving four doses of the anticancer vaccines before challenge with live B16-F10 cells. (A) C57BL/6 mice were either used as unvaccinated, controls or vaccinated with four doses of B16-F10/4-1BBL/B7.1/IFNγ/β cells (n=4) before subcutaneous challenge with $5 \times 10^4$ live B16-F10 cells. Tumor growth was monitored every two to three days and mice were euthanized when tumors reached a maximum of 2.0 cm in any direction. This data was translated into a survival analysis and significance was determined using the Log rank test. (B) Mice were prepared as described in (A), except challenged with $5 \times 10^5$ live B16-F10/B7.1 cells. The mice that remained tumor free for at least 112 days were given an additional two doses of vaccine as either B16-F10/4-1BBL/IFNγ/β (n=2), B16-F10/B7.1/IFNγ/β (n=4) or B16-F10/4-1BBL/B7.1/IFNγ/β (n=4) cells. Vaccinated and control, unvaccinated (n=4) mice were challenged with $5 \times 10^5$ live B16-F10/B7.1 cells (n=4) and the control mice remained untreated (n=4). Spleens were collected nine days following injection with live tumor burden and weights were recorded as the mean and SE.

Figure 22:
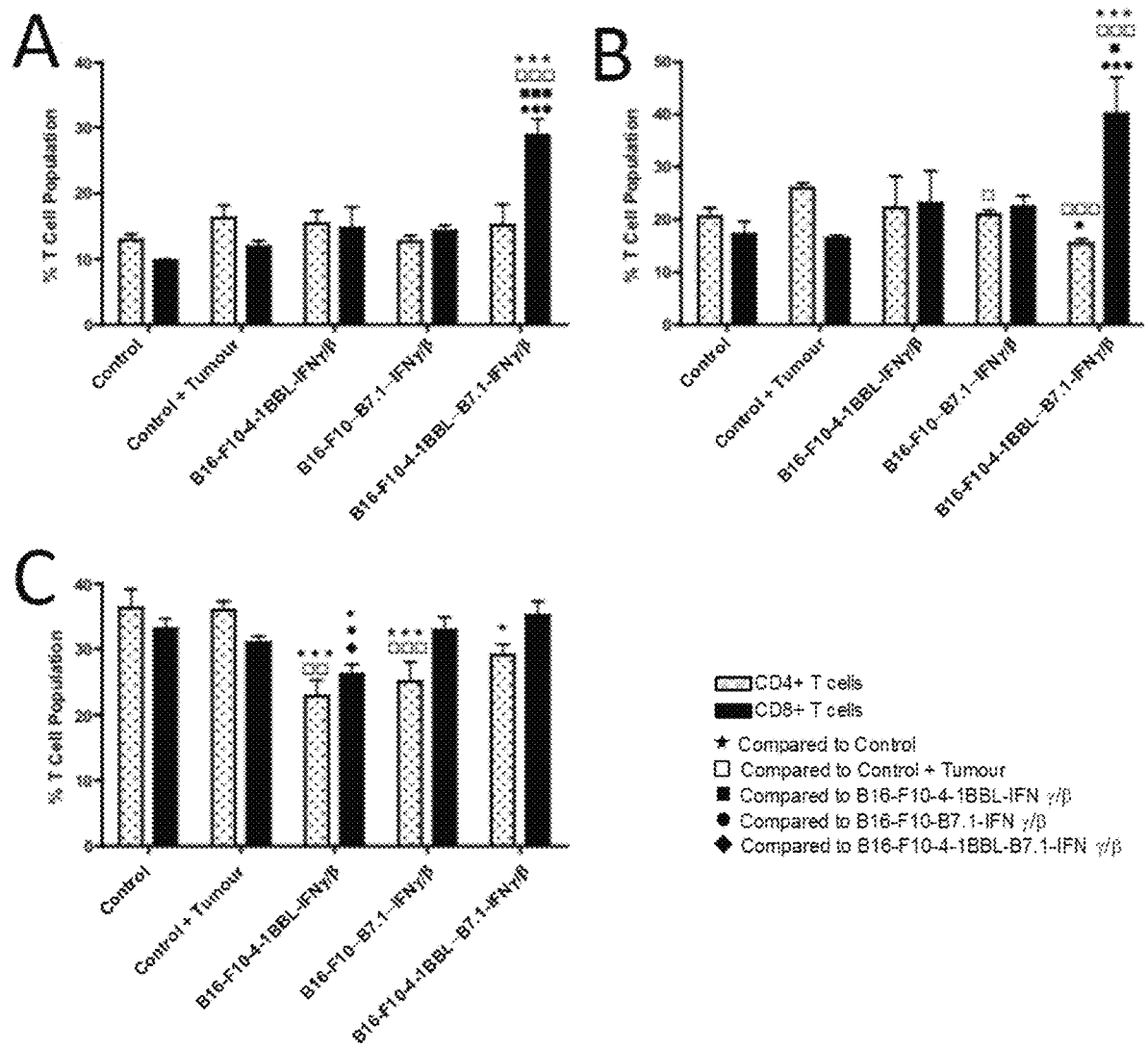

FIG. 22. Analysis of CD8$^+$ T cell populations in vaccinated mice that remained tumor free for an extended period of time after challenge with live tumor cells. C57BL/6 mice were used as controls or were treated with two doses of either the B16-F10/4-1BBL/IFNγ/β, B16-F10/B7.1/IFNγ/β or B16-F10/4-1BBL/B7.1/IFNγ/β cell vaccine before challenge with $5 \times 10^5$ live B16-F10/B7.1 cells. The mice that remained tumor free for at least 112 days were given an additional two booster doses of the same vaccines either as B16-F10/4-1BBL/IFNγ/β (n=2), B16-F10/B7.1/IFNγ/β (n=4) or B16-F10/4-1BBL/B7.1/IFNγ/β (n=4) cells. Vaccinated or control, unvaccinated mice (n=4) were challenged with 5×105 live B16-F10/B7.1 cells, four days following the final booster vaccination and control mice remained untreated (n=4). Mice were euthanized and their spleens (A), blood (B) and lymph nodes (C) were harvested nine days following the injection with live tumor burden. The lymphocytes were purified and analysed for % CD4$^+$ and CD8$^+$ T cell populations by flow cytometry. The mean and standard error are displayed.

Figure 23:
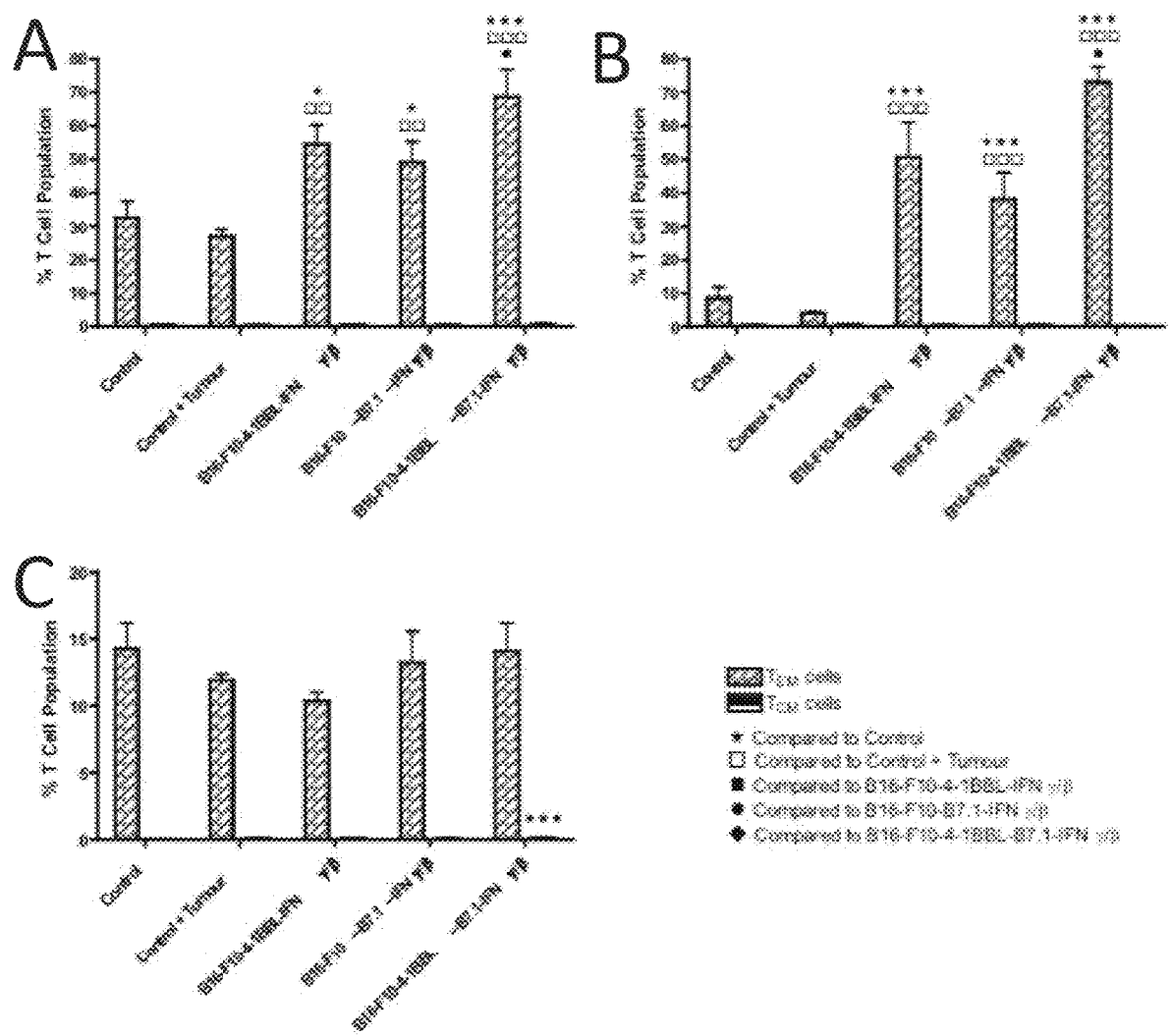

FIG. 23. Analysis of T$_{EM}$ cells in vaccinated mice that remained tumor free for an extended period of time after challenge with live tumor cells. C57BL/6 mice were used as controls or were treated with two doses of either the B16-F10/4-1BBL/IFNγ/β, B16-F10/B7.1/IFNγ/β or B16-F10/4-1BBL/B7.1/IFNγ/β cell vaccine before challenge with $5 \times 10^5$ live B16-F10/B7.1 cells. The mice that remained tumor free for at least 112 days were given an additional two booster doses of the same vaccines either as B16-F10/4-1BBL/IFNγ/β (n=2), B16-F10/B7.1/IFNγ/β (n=4) or B16-F10/4-1BBL/B7.1/IFNγ/β (n=4) cells. Vaccinated or control, unvaccinated mice (n=4) were challenged with $5 \times 10^5$ live B16-F10/B7.1 cells, four days following the final booster vaccination and control mice remained untreated (n=4). Mice were euthanized and their spleens (A), blood (B) and lymph nodes (C) were harvested nine days following the injection with live tumor burden. The lymphocytes were purified and CD8$^+$ T cell populations identified and simultaneously analysed for the presence of TEM and TCM CD8$^+$ T cell subpopulations by flow cytometry. The mean and standard error are displayed.

Figure 24:
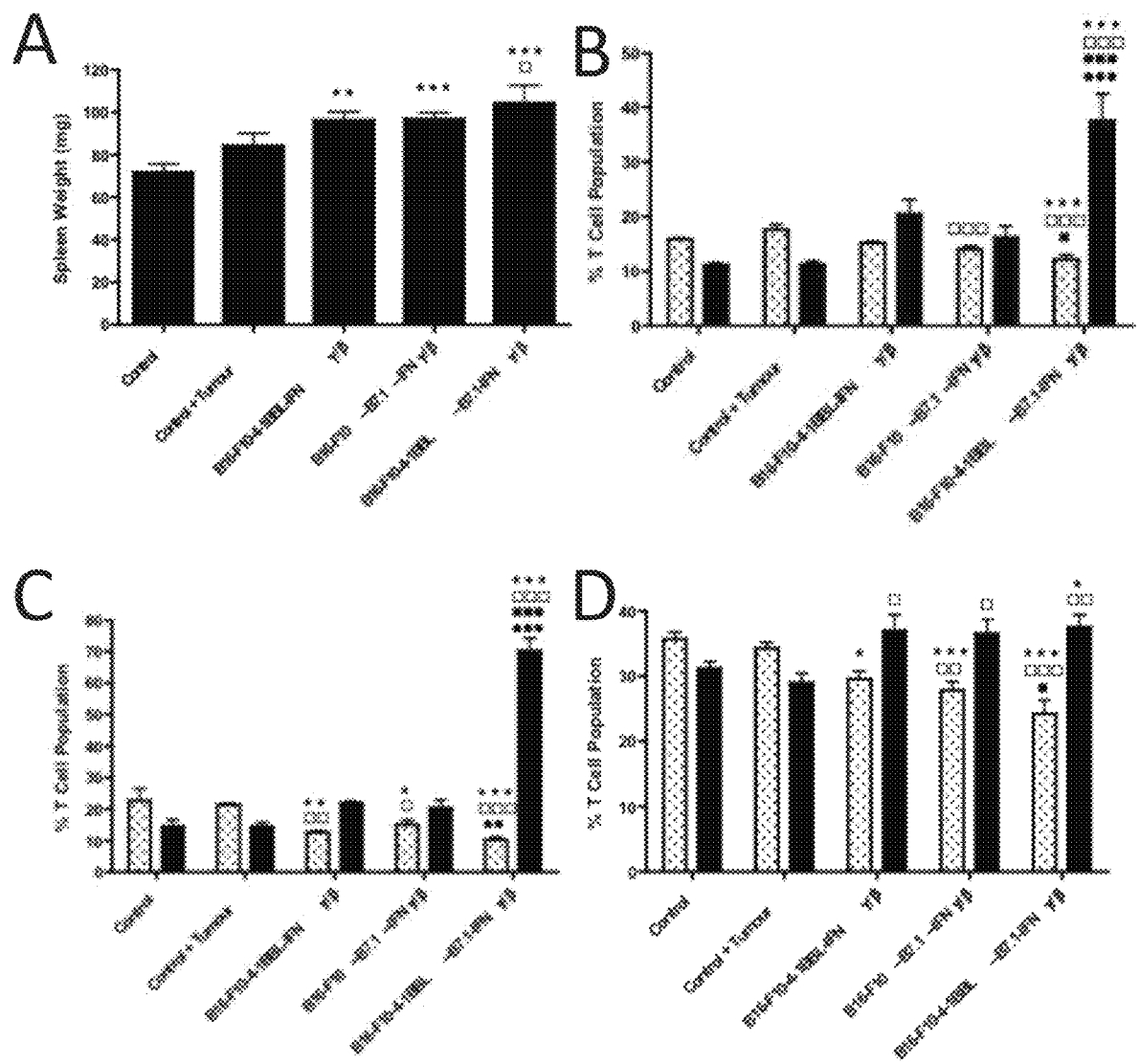

FIG. 24. Analysis of spleen weights and T cell populations in vaccinated mice that remained tumor free for an extended period of time after double challenge. C57BL/6 mice were either used as controls or vaccinated with four doses of either the B16-F10/4-1BBL/IFNγ/β, B16-F10/B7.1/IFNγ/β or B16-F10/4-1BBL/B7.1/IFNγ/β cell vaccine and then challenged with $5 \times 10^5$ live B16-F10/B7.1 cells. The mice remained tumor free for 102 days before being further boosted twice with the same vaccine cells and re-challenged with another $5 \times 10^5$ live B16-F10/B7.1 cells. The mice from the previous studies (FIG. 18) had remained tumor free for at least 190 days when they were boosted twice more four days apart with either the B16-F10/4-1BBL/IFNγ/β (n=3), B16-F10/B7.1/IFNγ/β (n=7) or B16-F10/4-1BBL/B7.1/IFNγ/β (n=6) cells. Vaccinated and control, unvaccinated (n=4) mice were challenged with $5 \times 10^5$ live B16-F10/B7.1 cells four days following the final booster vaccination and the control mice remained untreated (n=4). Mice were euthanized 6 days following injection with live tumor burden and (A) spleen weights were recorded as the mean. Spleens (B), blood (C) and lymph nodes (D) were harvested, the lymphocytes were purified and analysed for % CD4$^+$ and CD8$^+$ T cell populations by flow cytometry. The mean and standard error are displayed.

Figure 25:
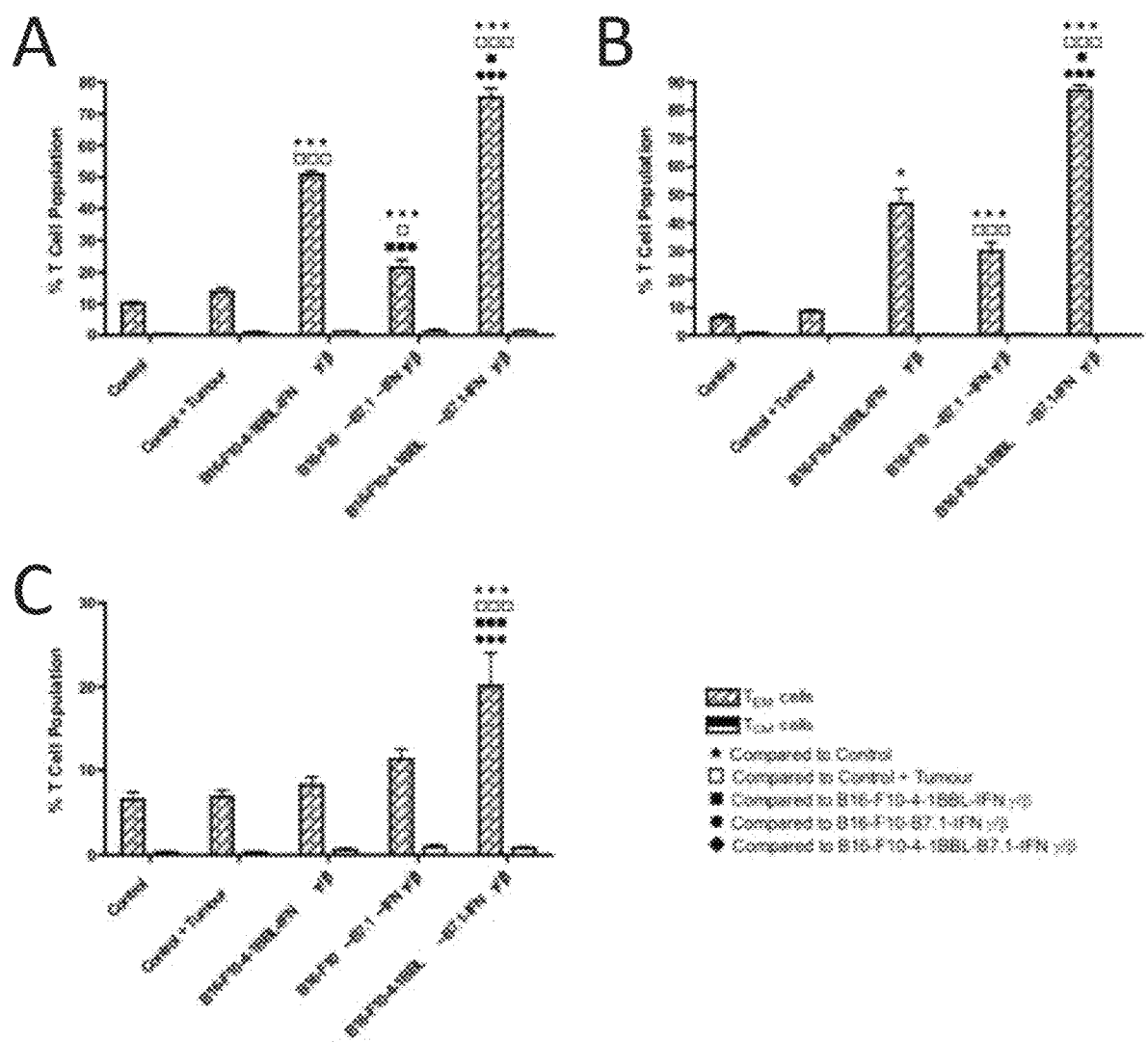

FIG. 25. T$_{EM}$ cells in vaccinated mice that remained tumor free for an extended period of time after challenge with live tumor cells. The lymphocytes of the spleens (A), blood (B) and lymph nodes (C) described in the previous Figure were further purified and CD8$^+$ T cell populations identified and simultaneously analysed for the presence of T$_{EM}$ and T$_{CM}$ CD8$^+$ T cell subpopulations by flow cytometry.

Figure 26:
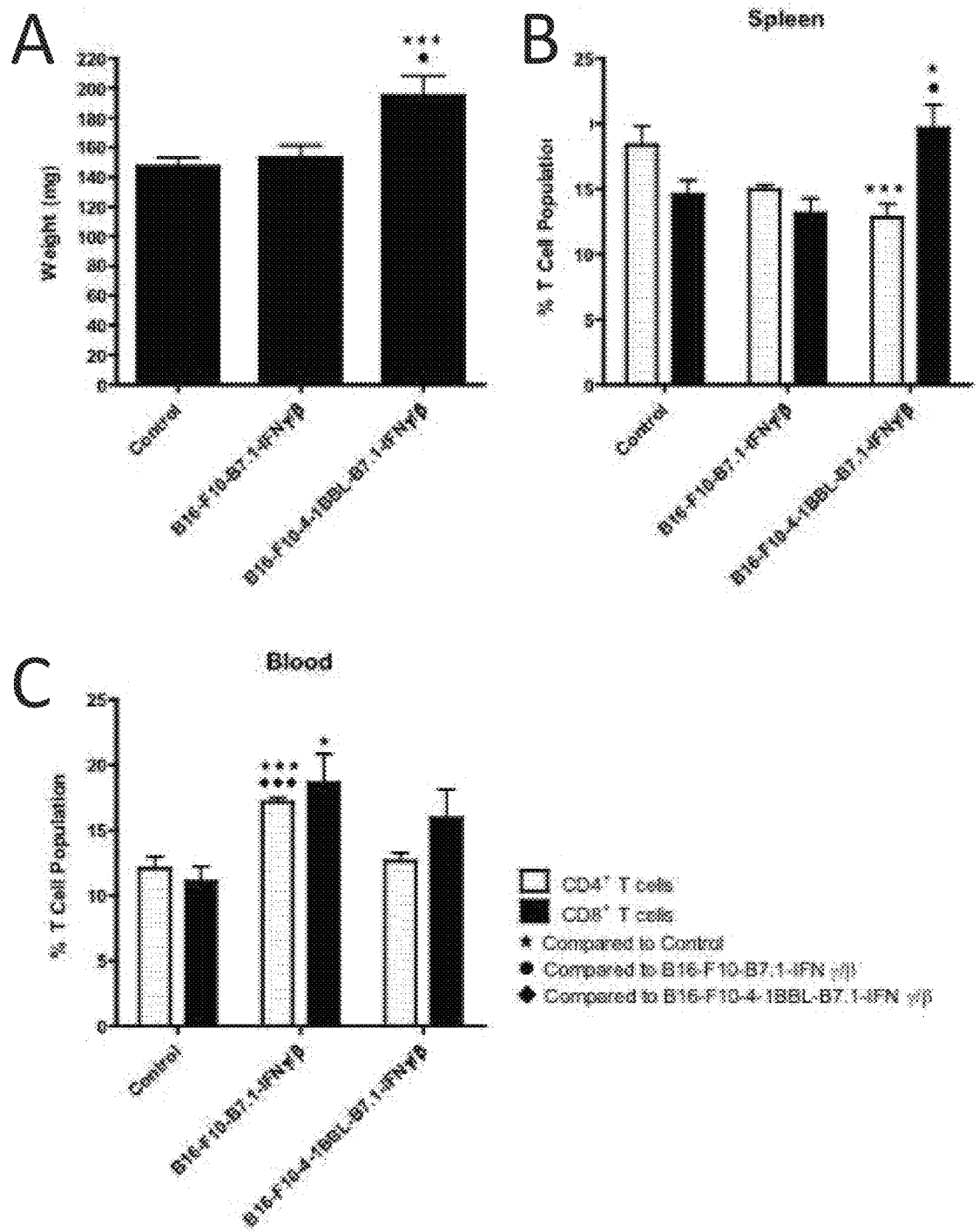

FIG. 26. LTα$^{-/-}$ mice produced elevated splenic CD8$^+$ T cell populations following injection with the B16-F10/4-1BBL/B7.1/IFNγ/β cell vaccine. LTα$^{-/-}$ mice were injected with either the B16-F10/B7.1/IFNγ/β (n=4) or B16-F10/4-1BBL/B7.1/IFNγ/β (n=8) anti-cancer vaccine or remained unvaccinated as controls (n=8). Four days following the final vaccination, spleens were collected and (A) weighed and then (B) spleens and (C) peripheral blood were analysed for differences in CD4$^+$ and CD8$^+$ T cell populations. This data is representative of two independent experiments and the mean±SE is shown.

Figure 27:
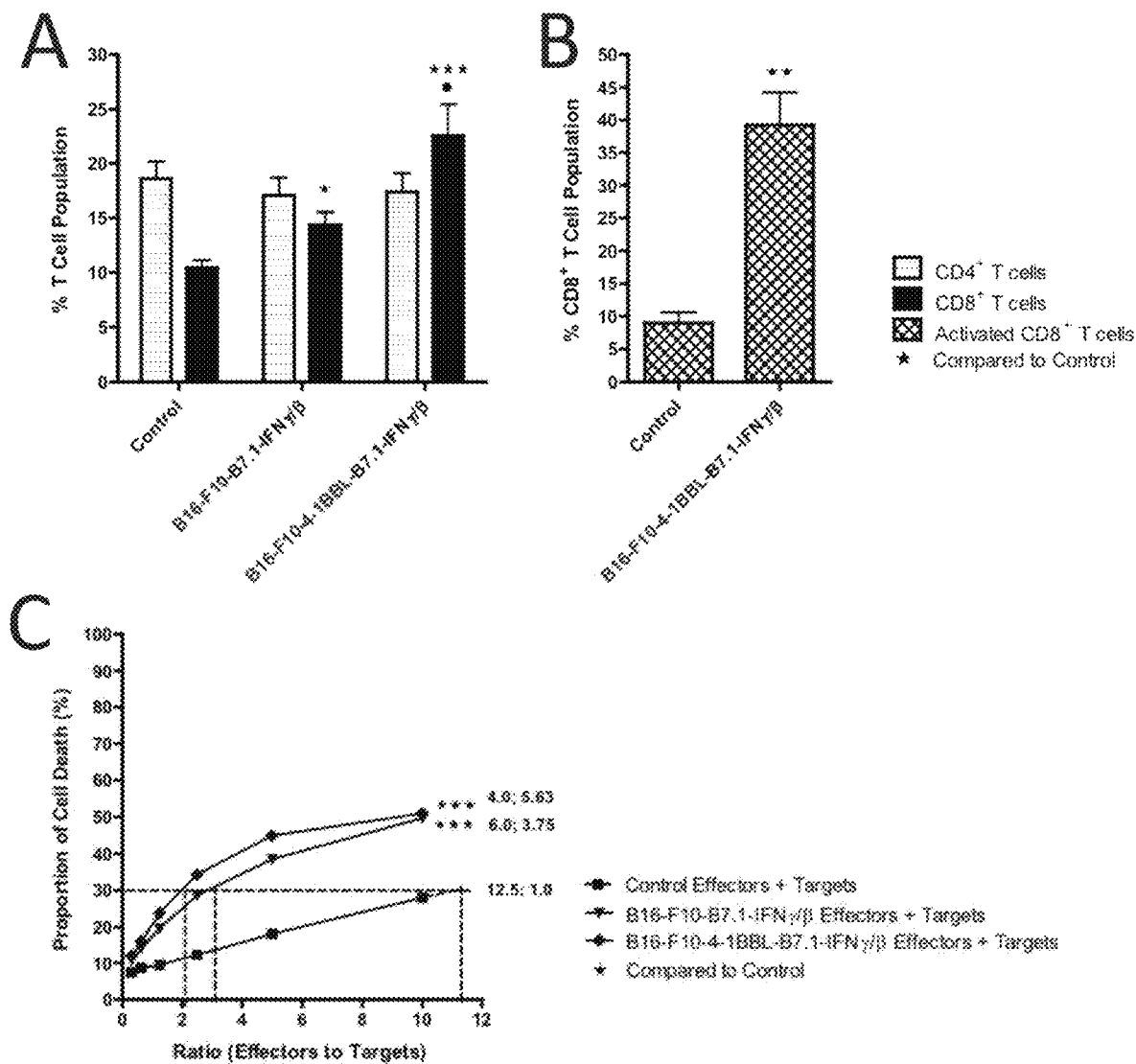

FIG. 27. % CD8$^+$ T cells and % activated CD8$^+$ T cells derived from B16-F10/4-1BBL/B7.1/IFNγ/β vaccinated LTα$^{-/-}$ mice were enhanced following culture in MLC and were most effective at killing target melanoma cells in CTL assays. LTα$^{-/-}$ mice were used as controls (n=8) or injected with either B16-F10/B7.1/IFNγ/β (n=4) or B16-F10/4-1BBL/B7.1/IFNγ/β (n=8) vaccines. Splenic derived lymphocytes were grown in MLC for three to five days then analysed for (A) changes in CD4$^+$ and CD8$^+$ T cell populations and (B) activated CD8$^+$ T cell populations. This data was collected from four independent experiments. (C) The lymphocytes were assessed for their ability to kill target melanoma cells in CTL assays. The ratios of the effector (E) to live cancer target cells (T) ranged from 0.3:1 up to 10:1 and the mean±SE of the proportion of cell death for each ratio of E:T are plotted. The values on the graph indicate the number of effector cells ($\times 10^4$) able to produce 30% target cell lysis and the relative fold increase in lytic units per effector cell population relative to the CTL response from unvaccinated mice.

Figure 28:
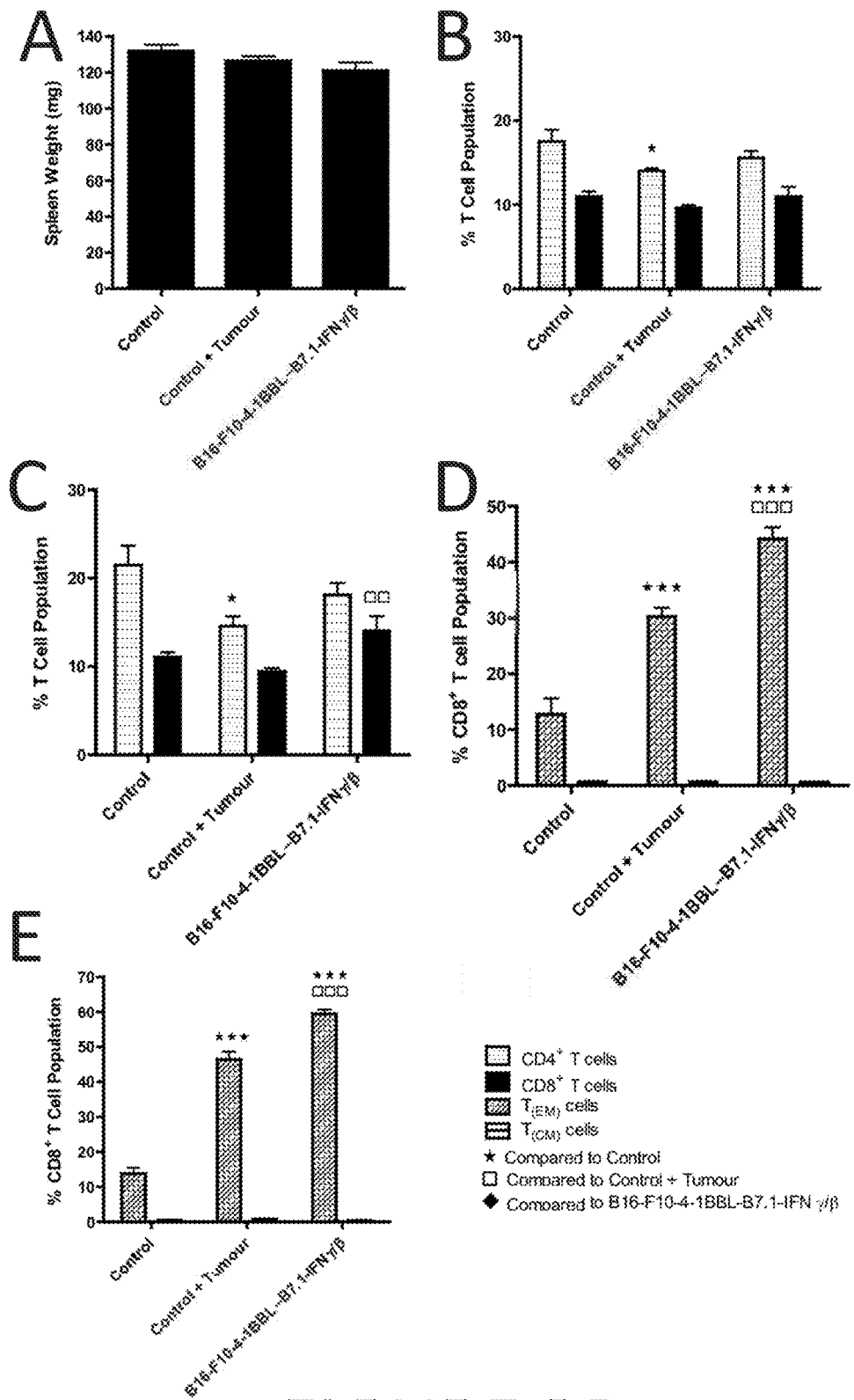

FIG. 28. The anti-cancer vaccine has a protective effect on the majority of LTα$^{-/-}$ mice challenged with $5 \times 10^5$ live B16-F10/B7.1 cells and subsequently increased the % T$_{EM}$ cell population produced by these mice. Vaccinated LTα$^{-/-}$ mice that remained tumour free after the initial tumour challenge were boosted twice with the B16-F10/4-1BBL/B7.1/IFNγ/β (n=3) cell vaccine and re-challenged with $5 \times 10^5$ live B16-F10/B7.1 cells. Vaccinated and control, unvaccinated (n=3) mice were challenged with $5 \times 10^5$ B16-F10/B7.1 cells, four days following the final booster vaccination. A group of control, unvaccinated mice remained untreated (n=4). Spleens were collected and (A) weighed and then lymphocytes from (B) spleens and (C) peripheral blood were analysed for CD4+ and CD8+ T cell populations. CD8+ T cell populations in (D) spleens and (E) peripheral blood were further analysed for the presence of $T_{EM}$ and $T_{CM}$ CD8+ T cell subpopulations.

Figure 29:
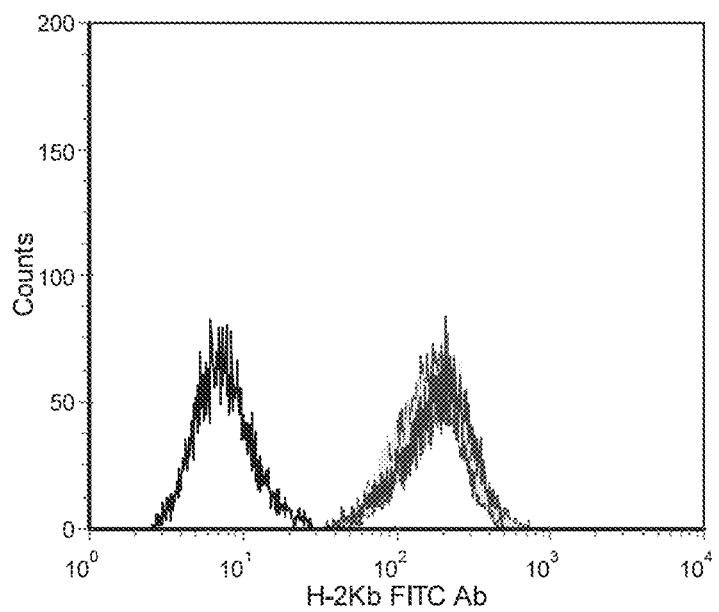

FIG. 29. No change in H-2K$^b$ expression on B16-F10-4-1BBL sort 1 cells after treatment with higher concentrations of IFNγ/β. The B16-F10-4-1BBL sort 1 cells were treated with various concentrations of IFNγ/β and then stained with FITC-conjugated anti-mouse H-2K$^b$ Ab. Detection of H-2K$^b$ expression on the cells was performed using the FACSCalibur. The black histogram represents the isotype stained sample of B16-F10/4-1BBL cells treated with 1000 IU/mL of IFNγ and 1000 IU/ml of IFNβ. The red histogram shows the B16-F10/4-1BBL cells treated with 1000 IU/ml of IFNγ and IFNβ and stained with the H-2K$^b$ Ab. The H-2K$^b$ expression on the cells after treatment with 2000 IU/mL IFNγ/1000 IU/mL IFNβ and 3000 IU/mL IFNγ/1000 IU/mL IFNβ is shown by the blue and green histograms respectively. The yellow and purple histograms displays the expression of H-2K$^b$ on the same cells after treatment with 1000 IU/mL IFNγ/2000 IU/mL IFNβ and 2000 IU/mL IFNγ/2000 IU/mL IFNβ respectively.

DETAILED DESCRIPTION OF THE INVENTION

1. Abbreviations

The following abbreviations are used throughout the application:
aa=Amino acid(s)
h=hours
IFN=Interferon
Ig=Immunoglobulin
IFN=Interferon
IL=Interleukin
MHC=Major Histocompatability Complex
min=minutes
MLC=Mixed lymphocyte cultures
nts=nucleotides
s=seconds
STAT=Signal transducers and activators of transcription

2. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "a cell" means one cell or more than one cell.

The term "about", as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about".

The terms "administration simultaneously" or "administering simultaneously" refer to the administration of a single composition containing both an immunostimulatory molecule and interferon treated animal cell, or the administration of each active as separate compositions and/or delivered by separate routes within a short enough period of time that the effective result is equivalent to that obtained when both such actives are administered as a single composition.

As used herein, "and/or" refers to and encompasses any and all possible combinations of one or more of the associated listed items, as well as the lack of combinations when interpreted in the alternative (or).

The term "agent" or "modulatory agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

The term "4-1BB agonist" as used herein refers to any agent which directly or indirectly agonizes or antagonizes a component so as to agonize or otherwise activate or increase the function of 4-1BB. In some embodiments, the 4-1BB agonist directly agonizes 4-1BB function. Suitably, the 4-1BB agonist directly agonizes 4-1BB function by binding with 4-1BB and activating the receptor. In some other embodiments, the 4-1BB agonist indirectly agonizes 4-1BB function. Suitably, the 4-1BB agonist of indirectly agonizes 4-1BB function by directly or indirectly increasing the level of one or more components, for example 4-1BB ligand (4-1BBL).

The term "allogeneic" as used herein refers to a cell or tissue that is derived from a donor or source that is genetically different although belonging to the same species as the subject.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

By "artificial antigen presenting cell" means a professional antigen presenting cell that is not naturally occurring in vivo. Antigen presenting cells can be generated in vivo from heterologous cell samples, as described in the present application. Prior to being artificially generated, the heterologous sample may not be or include any antigen presenting cell (e.g., an animal cell). Alternatively, the artificial antigen presenting cell could be derived from an antigen presenting cell (e.g., a macrophage) that is genetically modified to overexpress a polypeptide of interest.

By "autologous" is meant something (e.g., cells, tissues etc.) derived from the same organism.

By "biologically active fragment" is meant a fragment of a full-length parent polypeptide which fragment retains the activity of the parent polypeptide. A biologically active fragment will, therefore, inter alia have a biological activity of a parent polypeptide selected from an interferon alpha, an interferon beta, an interferon gamma, a B7-1 molecule and a B7-2 molecule. As used herein, the term "biologically active fragment" includes deletion mutants and small peptides, for example of at least 8, preferably at least 10, more preferably at least 15, even more preferably at least 20 and even more preferably at least 30 contiguous amino acids, which comprise the above activities. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and *staphylococcus* V8-protease. The digested fragments can be purified by, for example, high performance liquid chromatographic (HPLC) techniques.

As used herein, a "cellular composition", "cellular vaccine" or "cellular immunogen" refers to a composition comprising at least one cell population, which is optionally inactivated, as an active ingredient.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

As used herein, the term "culturing" or "cultured" refers to the in vitro steps necessary to incubate a population of cells under conditions that support the growth, viability, maintenance and/or differentiation of the cells. In the art, it is widely recognized that a number of formats, medias, temperature ranges, gas concentrations, culture additives, will support the growth, viability, maintenance and/or differentiation of cells, and that specific parameters need to be defined in the culture system of interest. The parameters of the culture will vary depending on the format selected and the specific goals of the culture (e.g., the production of artificial antigen-presenting cells as disclosed herein). It is recognized that the determination of adequate culture parameters is routine in the art.

By "effective amount", in the context of treating a condition, is meant the administration of an amount of agent (e.g., an artificial antigen-presenting cell of the present invention or composition comprising such a cell) that elicits an immune response in an individual in need of such treatment, either in a single dose or as part of a series, that is effective for treatment of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

To enhance immune response ("immunoenhancement"), as is well-known in the art, means to increase the animal's capacity to respond to foreign or disease-specific antigens (e.g., cancer antigens) i.e., those cells primed to attack such antigens are increased in number, activity, and ability to detect and destroy the those antigens. Strength of immune response is measured by standard tests including: direct measurement of peripheral blood lymphocytes by means known to the art; natural killer cell cytotoxicity assays (see, e.g., Provinciali M. et al (1992, 3. Immunol. Meth. 155: 19-24), cell proliferation assays (see, e.g., Vollenweider, I. And Groseurth, P. 3. (1992, 3. Immunol. Meth. 149: 133-135), immunoassays of immune cells and subsets (see, e.g., Loeffler, D. A., et al. (1992, Cytom. 13: 169-174); Rivoltini, L., et al. (1992, Can. Immunol. Immunother. 34: 241-251); or skin tests for cell-mediated immunity (see, e.g., Chang, A. E. et al (1993, Cancer Res. 53: 1043-1050). Any statistically significant increase in strength of immune response as measured by the foregoing tests is considered "enhanced immune response" "immunoenhancement" or "immunopotentiation" as used herein. Enhanced immune response is also indicated by physical manifestations such as fever and inflammation, as well as healing of systemic and local infections, and reduction of symptoms in disease, i.e., decrease in tumor size, alleviation of symptoms of a disease or condition including a cancer or tumor. Such physical manifestations also define "enhanced immune response" "immunoenhancement" or "immunopotentiation" as used herein. In some embodiments, the terms "enhanced immune response" "immunoenhancement" or "immunopotentiation" include stimulation or augmentation of a cellular and/or humoral immune response (e.g., to a target antigen).

As used herein, the term "exogenous" refers to any material introduced from or produced outside an organism, cell, tissue or system.

As used herein, the term "expression" and its grammatic equivalents include production of polynucleotides and polypeptides, in particular, the production of RNA (e.g., mRNA) from a gene or portion of a gene, and includes the production of a polypeptide encoded by an RNA or gene or portion of a gene, and the appearance of a detectable material associated with expression. For example, the presence of a polypeptide on the surface of a cell is included within the scope of the term "expression", which is often described as "surface expression". Another example is the binding of a binding ligand, such as a hybridization probe or antibody, to a gene or other polynucleotide or oligonucleotide, a polypeptide or a protein fragment, and the visualization of the binding ligand. Thus, increased intensity of a spot on a microarray, on a hybridization blot such as a Northern blot, or on an immunoblot such as a Western blot, or on a bead array, or by PCR analysis, is included within the term "expression" of the underlying biological molecule.

By "expression construct" is meant a genetic construct that includes the necessary elements that permit transcribing an inserted polynucleotide, and, optionally, translating the transcript into a polypeptide. An expression construct typically comprises in operable connection and in a 5' to 3' direction: a promoter, functional in the host cell into which the construct will be introduced, the polynucleotide to be expressed, and a terminator functional in the host cell into which the construct will be introduced. Expression constructs contemplated herein may be inserted into a replicable vector for cloning or for expression (also known as "expression vectors"), or may be incorporated into the host genome.

As used herein, the term "function" refers to a biological, enzymatic, or therapeutic function.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The term "heterogeneous cell population" generally refers to a mixture of two or more cells of the same type expressing different levels of cell surface markers, and/or two or more cell types. Examples of heterogeneous cell populations can include: bodily fluids, biological specimens, dissociated tumor specimens, cultured cells, and any combination thereof.

By "high levels" or "increased levels" in the context of molecular expression is meant a level that is greater than normal, greater than a standard such as a predetermined measure or a subgroup measure or that is relatively greater than another subgroup measure. For example, high or increased B7 level refers to a level of B7 that is greater than a normal B7 level. A normal B7 level may be determined according to any method available to one skilled in the art. A high or increased level of B7 may also refer to a level that is equal to or greater than a predetermined level, such as a predetermined cutoff. A high or increased level of B7 may also refer to a level of B7 wherein a high or increased level of B7 subgroup has relatively greater levels of B7 than another subgroup. In some embodiments, a high or increased level of B7 is based on having higher than the median levels of B7 at baseline, representative examples of which include 2-fold, 5-fold, 10-fold, 50-fold, 100-fold or 200-fold above a baseline level. For example, B16High cells as used herein, express high levels of a B7 molecule on their surface, which levels are 10-fold, 50-fold, 100-fold and 200-fold above the level of B7 expressed by wild-type B16 cells.

Reference herein to "immuno-interactive" includes reference to any interaction, reaction, or other form of association between molecules and in particular where one of the molecules is, or mimics, a component of the immune system.

A composition is "immunogenic" if it is capable of either: a) generating an immune response against an antigen (e.g., a tumor antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

The term "inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilized and are incapable of division are also examples of inactivated cells.

By "isolated" is meant material that is substantially or essentially free from components that normally accompany it in its native state.

By "modulating" is meant increasing or decreasing, either directly or indirectly, the level and/or functional activity of a target molecule. For example, an agent may indirectly modulate the said level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

By "obtained from" is meant that a sample such as, for example, a nucleic acid extract or polypeptide extract is isolated from, or derived from, a particular source of the host. For example, the extract may be obtained from a tissue or a biological fluid isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The term "operably connected" or "operably linked" as used herein means placing a structural gene under the regulatory control of a regulatory element including but not limited to a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards etc.), and fish. In specific embodiments, the subject is a primate such as a human. However, it will be understood that the aforementioned terms do not imply that symptoms are present.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally occurring allelic variants.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogs of an amino acid including, for example, unnatural amino acids or polypeptides with substituted linkages.

The term "polypeptide variant" refers to polypeptides which vary from a reference polypeptide by the addition, deletion or substitution of at least one amino acid. It is well understood in the art that some amino acids may be changed to others with broadly similar properties without changing the nature of the activity of the polypeptide. Accordingly, polypeptide variants as used herein encompass polypeptides that have similar activities to a parent polypeptide selected from an interferon alpha, an interferon beta, an interferon gamma, a B7-1 molecule and a B7-2 molecule. Preferred variant polypeptides comprise conservative amino acid substitutions. Exemplary conservative substitutions in a polypeptide may be made according to the following table:

TABLE 1

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE 1. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Asn) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a smaller side chain (e.g., Ala, Ser) or no side chain (e.g., Gly) is substituted for, or by, one having a bulky side chain (e.g., Phe or Trp).

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridize and serve as a site for the initiation of synthesis. By "substantially complementary", it is meant that the primer is sufficiently complementary to hybridize with a target nucleotide sequence. Preferably, the primer contains no mismatches with the template to which it is designed to hybridize but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridize therewith and thereby form a template for synthesis of the extension product of the primer.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

As used herein "stimulating" an immune or immunological response refers to administration of a composition that initiates, boosts, or maintains the capacity for the host's immune system to react to a target substance, such as a foreign molecule, or a tumor cell, at a level higher than would otherwise occur. Stimulating a "primary" immune response refers herein to eliciting specific immune reactivity in a subject in which previous reactivity was not detected; for example, due to lack of exposure to the target antigen, refractoriness to the target, or immune suppression. Stimulating a "secondary" response refers to the reinitiation, boosting, or maintenance of reactivity in a subject in which previous reactivity was detected; for example, due to natural immunity, spontaneous immunisation, or treatment using one or several compositions or procedures.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing 0.5 M sodium phosphate, 7% SDS at 65° C., followed by one or more washes at 0.2×SSC, 1% SDS at 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS IN MOLECULAR BIOLOGY (supra) at pages 2.10.1 to 2.10.16 and MOLECULAR CLONING. A LABORATORY MANUAL (Sambrook, et al., eds.) (Cold Spring Harbor Press 1989) at sections 1.101 to 1.104.

As used herein, the term "syngeneic" refers to a cell or tissue that is derived from a donor or source that is genetically identical to the subject.

As used herein, the terms "treatment," "treating," and the like, refer to obtaining a desired pharmacologic and/or physiologic effect. The effect may be therapeutic in terms of a partial or complete cure for a disease or condition (e.g., a hematologic malignancy) and/or adverse affect attributable to the disease or condition. These terms also cover any treatment of a condition or disease in a mammal, particularly in a human, and include: (a) inhibiting the disease or condition, i.e., arresting its development; or (b) relieving the disease or condition, i.e., causing regression of the disease or condition.

As used herein, the term "xenogeneic" refers to a cell or tissue that is derived from a donor or source that is of a different species than the subject.

3. Artificial Antigen Presenting Cells

The present invention stems at least in part from the discovery that there is a synergistic enhancement in immunopotentiation of animal cells by culturing the animal cells in the presence of at least one interferon, wherein the animal cells express on their surface a B7 molecule and a 4-1BB agonist.

Accordingly, the present invention provides in one aspect an artificial antigen-presenting cell comprising a B7 molecule and a 4-1BB agonist on its cell surface, wherein the antigen-presenting function of the cell is enhanced by exposure to at least one IFN, wherein the antigen-presenting cell is typically derived from an animal cell. Preferred cells are those with a defined MHC genomic region or equivalent and with the capability of increasing or enhancing class I MHC presentation of antigenic molecules to cell surfaces.

The cells of the present invention may be isolated from the intended host, treated and then re-introduced or reinfused into that host. It is particularly convenient to use cells obtained from the host to be treated, either by surgical resection, biopsy, blood sampling, or other suitable technique. Such cells are referred to herein as "autologous" cells. Alternatively, cells or cell lines (e.g., tumor cell lines) may be prepared and/or cultured from one source and introduced into a different host. Such cells include "syngeneic cells, "allogeneic" cells and "xenogeneic cells". One particular form of allogeneic cells comprises a generic cell line with shared major and/or minor histocompatibility antigens to potential recipients.

Suitably, the generic cell line naturally expresses the B7 molecule at levels sufficient to trigger an immune response, including one or both of a cellular immune response and a humoral immune response. In preferred embodiments, the immune response includes a T cell immune response, and more preferably a cytotoxic T lymphocyte immune response, in the intended host.

It is preferred the generic cell line comprises major histocompatibility (MHC) class I antigens compatible with a high percentage of the population that is susceptible or predisposed to a particular condition. Suitably, the condition being treated or prevented by administration of the artificial antigen-presenting cell is a cancer or tumor. Preferably, the generic cell line expresses high levels of an endogenous B7 molecule. It is also preferred that the generic cell line is highly susceptible to treatment with at least one IFN as described herein (i.e., implied high level expression of class I HLA).

In one embodiment, treated cells (e.g., cancer cells) or cell lines are suitably rendered inactive to prevent further proliferation once administered to the subject (e.g., to prevent the introduction of a cancer or tumor into a subject). Any physical, chemical, or biological means of inactivation may be used, including but not limited to irradiation (preferably with at least about 5,000 cGy, more preferably at least about 10,000 cGy, more preferably at least about 20,000 cGy); or treatment with mitomycin-C (preferably at least 10 µg/mL; more preferably at least about 50 µg/mL).

The present invention extends to animal cells from, for example, avian species, reptiles and mammals. Mammals are preferred and include humans, livestock animals (e.g., sheep, cows, horses, pigs), laboratory test animals (e.g., mice, rats, rabbits, guinea pigs), companion animals (e.g., cats, dogs) and captive wild animals (e.g., kangaroos, deer, foxes). Humans are the most preferred animals and both autologous, syngeneic and allogeneic cells may be employed in human subjects.

The animal cells are preferably cancer or tumor cells. The compositions in accordance with the present invention would be derived from the tumor or cancer cells. For example, in the treatment of lung cancer in accordance with the practices of this invention, the lung cancer cells would be treated as described hereinabove to produce a lung cancer immune-potentiating composition or vaccine. Similarly, breast tumor or cancer cells, prostate cancer cells, colon cancer cells, pancreas cancer cells, stomach cancer cells, bladder cancer cells, kidney cancer cells and the like would be produced and employed as immunotherapeutic agents in accordance with the practices for the prevention and/or treatment of the tumor or cancer cell from which the composition according to the invention was produced. In a preferred embodiment, the animal cells are melanoma cells.

3.1 The B7 Molecule

The B7 molecule is the ligand of the co-stimulatory molecule CD28, which has been shown to enhance IL-2 secretion and to prevent the induction of anergy in both T cell clones and primary T cells. The interaction between the B7 molecule and CD28 stimulates T-cell proliferation by increasing the transcription of the mRNA stability of IL-2, as well as by upregulating the anti-apoptotic protein Bcl-$X_L$.

In a preferred embodiment, the method further comprises isolating cells expressing the B7 molecule from a heterogeneous population of animal cells. Any method of isolation is contemplated by the present invention. Suitable methods for isolating particular cells are known to those of skill in the art. For example, one can take advantage of one or more particular characteristics of a cell to specifically isolate that cell from a heterogeneous population. Such characteristics include, but are not limited to, anatomical location of a cell, cell density, cell size, cell morphology, cellular metabolic activity, cell uptake of ions such as $Ca^{2+}$, $K^+$, and $H^+$ ions, cell uptake of compounds such as stains, markers expressed on the cell surface, protein fluorescence, and membrane potential. Suitable methods that can be used in this regard include surgical removal of tissue, flow cytometry techniques such as fluorescence-activated cell sorting (FACS), immunoaffinity separation (e.g., magnetic bead separation such as DYNABEAD™ separation), density separation (e.g., metrizamide, PERCOLL™, or FICOLL™ gradient centrifugation), and cell-type specific density separation.

In the present case, the cells are suitably isolated by flow cytometry or by immunoaffinity separation using an antigen-binding molecule that is immuno-interactive with the B7 molecule.

According to an alternate embodiment, the method further comprises modifying the animal cells to express on their surface the B7 molecule. Thus, the B7 molecule is a B7 membrane molecule, wherein at least a portion of said molecule is exposed to the extracellular environment (i.e., the exterior of a respective cell). The B7 molecule includes, but is not restricted to, B7.1 and B7.2. Preferably, the B7 molecule is B7.1. Suitable polypeptide sequences for B7.1 and B7.2 include, but are not restricted to, those set forth respectively in SEQ ID NO: 1 (Uniprot Accession No. P33681) and SEQ ID NO: 2, including biologically-active fragments thereof, and variants or derivatives of these.

[SEQ ID NO: 1]
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVSQDPETELYAV

SSKLDFNMTTNHSFMCLIKYGHLRVNQTFNWNTTKQEHFPDNLLPSWAIT

LISVNGIFVICCLTYCFAPRCRERRRNERLRRESVRPV;
and,

```
                                                    [SEQ ID NO: 2]
MDPQCTMGLSNILFVMAFLLSGAAPLKIQAYFNETADLPCQFANSQNQSL

SELVVFWQDQENLVLNEVYLGKEKFDSVHSKYMGRTSFDSDSWTLRLHNL

QIKDKGLYQCIIHHKKPTGMIRIHQMNSELSVLANFSQPEIVPISNITEN

VYINLTCSSIHGYPEPKKMSVLLRTKNSTIEYDGVMQKSQDNVTELYDVS

ISLSVSFPDVTSNMTIFCILETDKTRLLSSPFSIELEDPQPPPDHIPWIT

AVLPTVIICVMVFCLILWKWKKKKRPRNSYKCGTNTMEREESEQTKKREK

IHIPERSDEAQRVFKSSKTSSCDKSDTCF.
```

In some embodiments, the step of modification comprises introducing into the animal cells a polynucleotide from which the B7 molecule is expressible. Suitably, the polynucleotide is operably linked to a regulatory polynucleotide preferably in the form of an expression vector. Regulatory polynucleotides which can be utilised to regulate expression of the polynucleotide include, but are not limited to, a promoter, an enhancer, and a transcription terminator. Such regulatory polynucleotides are known to those of skill in the art. The expression vector preferably comprises at least one promoter. Suitable promoters that can be utilised to induce expression of the polynucleotide include constitutive promoters and inducible promoters.

Any suitable polynucleotide encoding the B7 molecule can be employed. Polynucleotides encoding B7.1 molecules which can be utilised in accordance with the invention are described, for example, in Freeman et al. (1989, *J. Immunol.* 143: 2714-2722), Freeman et al. (1992, *Blood* 79: 489-494), and in the GenBank database under locus designations HUMIGB7 (Accession number M27533) and NM_005191 (Accession number NM_005191). Suitable polynucleotides encoding B7.2 molecules are described, for example, in Azuma et al. (1993, *Nature* 336: 76-79), Chen et al. (1994, *J. Immunol.* 152: 4929-4963), and in the GenBank database under locus designation NM_006889 (Accession number NM_006889).

An exemplary expression vector for expression of the B7 protein includes the herpes simplex amplicons described for example by Fong et al. in U.S. Pat. No. 6,051,428.

It will be understood by persons of skill in the art that the techniques for assembling and expressing DNA encoding the B7 molecule, e.g., synthesis of oligonucleotides, nucleic acid amplification techniques, transforming cells, constructing vectors, expression systems, and the like and transducing or otherwise introducing such DNA into animal cells are well-established in the art, and most practitioners are familiar with the standard resource materials for specific conditions and procedures.

3.2 The 4-1BB Agonist 4-1BB is a member of the tumor necrosis factor (TNF) receptor superfamily, and is a co-stimulatory receptor molecule (Vinay and Kwon, 1998; and Kwon et al 2000). 4-1BB is primarily expressed on activated T cells (Pollok et al. (1993) *J. Immunol.* 150:771-781) and NK cells (Melero et al. 1998). The natural ligand for 4-1BB is 4-1BB ligand (4-1BBL), which has been detected on activated B and T cells, macrophages, and dendritic cells (Goodwin et al 1993; Pollok et al. 1994; and Alderson et al. 1994). As described herein, 4-1BB agonists such as 4-1BBL and anti-4-1BB antibodies can be used to stimulate AICD of T cells and autoreactive B cells.

The method therefore further comprises modifying the animal cells to express on their surface the 4-1BB agonist. Thus, the 4-1BB agonist is a membrane molecule, wherein at least a portion of said molecule is exposed to the extracellular environment (i.e., the exterior of a respective cell). The 4-1-BB agonist includes, but is not restricted to, 4-1BBL or a biologically active fragment thereof. A suitable polypeptide sequence for 4-1BBL includes, but is not restricted the following polypeptide sequence of human 4-1BB (UniProtKB accession number P41273,1):

```
                                                    [SEQ ID NO: 3]
MEYASDASLDPEAPWPPAPRARACRVLPWALVAGLLLLLLLAAACAVFLA

CPWAVSGARASPGSAASPRLREGPELSPDDPAGLLDLRQGMFAQLVAQNV

LLIDGPLSWYSDPGLAGVSLTGGLSYKEDTKELVVAKAGVYYVFFQLELR

RVVAGEGSGSVSLALHLQPLRSAAGAAALALTVDLPPASSEARNSAFGFQ

GRLLHLSAGQRLGVHLHTEARARHAWQLTQGATVLGLFRVTPEIPAGLPS

PRSE.
``` including biologically active fragments thereof, and variants of this sequence.

This wild-type polynucleotide sequence that encodes for the sequence set forth in SEQ ID NO: 4 is as follows:

```
                                                    [SEQ ID NO: 4]
AAAAAGCGGCGCGCTGTGTCTTCCCGCAGTCTCTCGTCATGGAATACGCC

TCTGACGCTTCACTGGACCCCGAAGCCCCGTGGCCTCCCGCGCCCCGCGC

TCGCGCCTGCCGCGTACTGCCTTGGGCCCTGGTCGCGGGGCTGCTGCTGC

TGCTGCTGCTCGCTGCCGCCTGCGCCGTCTTCCTCGCCTGCCCCTGGGCC

GTGTCCGGGGCTCGCGCCTCGCCCGGCTCCGCGGCCAGCCCGAGACTCCG

CGAGGGTCCCGAGCTTTCGCCCGACGATCCCGCCGGCCTCTTGGACCTGC

GGCAGGGCATGTTTGCGCAGCTGGTGGCCCAAAATGTTCTGCTGATCGAT

GGGCCCCTGAGCTGGTACAGTGACCCAGGCCTGGCAGGCGTGTCCCTGAC

GGGGGGCCTGAGCTACAAAGAGGACACGAAGGAGCTGGTGGTGGCCAAGG

CTGGAGTCTACTATGTCTTCTTTCAACTAGAGCTGCGGCGCGTGGTGGCC

GGCGAGGGCTCAGGCTCCGTTTCACTTGCGCTGCACCTGCAGCCACTGCG

CTCTGCTGCTGGGGCCGCCGCCCTGGCTTTGACCGTGGACCTGCCACCCG

CCTCCTCCGAGGCTCGGAACTCGGCCTTCGGTTTCCAGGGCCGCTTGCTG

CACCTGAGTGCCGGCCAGCGCCTGGGCGTCCATCTTCACACTGAGGCCAG

GGCACGCCATGCCTGGCAGCTTACCCAGGGCGCCACAGTCTTGGGACTCT

TCCGGGTGACCCCCGAAATCCCAGCCGGACTCCCTTCACCGAGGTCGGAA

TAACGTCCAGCCTGGGTGCAGCCCACCTGGACAGAGTCCGAATCCTACTC

CATCCTTCATGGAGACCCCTGGTGCTGGGTCCCTGCTGCTTTCTCTACCT

CAAGGGGCTTGGCAGGGGTCCCTGCTGCTGACCTCCCCTTGAGGACCCTC

CTCACCCACTCCTTCCCCAAGTTGGACCTTGATATTTATTCTGAGCCTGA

GCTCAGATAATATATTATATATATTATATATATATATATATTTCTATTTA

AAGAGGATCCTGAGTTTGTGAATGGACTTTTTTAGAGGAGTTGTTTTGGG

GGGGGGGGGGTCTTCGACATTGCCGAGGCTGGTCTTGAACTCCTGGACTT

AGACGATCCTCCTGCCTCAGCCTCCCAAGCAACTGGGATTCATCCTTTCT

ATTAATTCATTGTACTTATTTGCTTATTTGTGTGTATTGAGCATCTGTAA
```

-continued

```
TGTGCCAGCATTGTGCCCAGGCTAGGGGGCTATAGAAACATCTAGAAATA

GACTGAAAGAAAATCTGAGTTATGGTAATACGTGAGGAATTTAAAGACTC

ATCCCCAGCCTCCACCTCCTGTGTGATACTTGGGGGCTAGCTTTTTCTT

TCTTTCTTTTTTTTGAGATGGTCTTGTTCTGTCAACCAGGCTAGAATGCA

GCGGTGCAATCATGAGTCAATGCAGCCTCCAGCCTCGACCTCCCGAGGCT

CAGGTGATCCTCCCATCTCAGCCTCTCGAGTAGCTGGGACCACAGTTGTG

TGCCACCACACTTGGCTAACTTTTTAATTTTTTTGCGGAGACGGTATTGC

TATGTTGCCAAGGTTGTTTACATGCCAGTACAATTTATAATAAACACTCA

TTTTTCCTCCCTCTGAAAAAAAAAAAAAA.
```

Accordingly, the artificial antigen presenting cells of the present invention express on their cell surface molecules that bind to 4-1BB. Suitably, therefore, the molecules provided herein are generally polypeptides. In some preferred embodiments, the 4-1BB agonist useful in the methods provided herein can be 4-1BBL or a functions' fragment of 4-1BBL (i.e., a fragment of 4-1BBL that binds to 4-1BB with at least 20% (e.g., at least 20%, 30%, 40%, 50%, 60%, 70%, 80%, 90%, 95%, 98%, 99%, 99.5%, 100% or even more) of the avidity with which full-length 4-1BBL binds to 4-1BB, and functions to activate the receptor and potentiate an immune response.

In alternative embodiments, the 4-1BB agonist can be an antibody that has specific binding activity for 4-1BB. The terms "antibody" and "antibodies" encompass intact molecules as well as fragments thereof that are capable of binding to and activating 4-1BB. An antibody can be of any immunoglobulin (Ig) class, including IgM, IgA, IgD, IgE, and IgG, and any subclass thereof. Antibodies of the IgM class typically are pentavalent and may be particularly useful because one antibody molecule can cross-link a plurality of 4-1BB polypeptides. Immune complexes containing Ig molecules that are cross-linked (e.g., cross-linked IgG) and are thus multivalent also could be capable of cross-linking a plurality of 4-1BB molecules, and may be particularly useful.

Recombinant antibodies specific for 4-1BB, such as chimeric and humanized monoclonal antibodies comprising both human and non-human portions, are within the scope of the invention. Such chimeric and humanized monoclonal antibodies can be produced by recombinant DNA techniques known in the art, for example, using methods described in International Patent Application No. PCT/US86/02269, European Patent Application Nos. EP184187, EP171496, EP125023, EP173494; International Patent Application Publication No. WO86/01533, U.S. Pat. Nos. 4,816,567, and 5,225,539, and the following journal articles: Better et al. (1988) *Science* 240: 1041-43, Liu et al (1987) *J. Immunol.* 139: 3521-26, Sun et al. (1987) *PNAS* 84:214-18 Nishimura et al. (1987) *Canc. Res.* 47: 999-1005, Wood et al (1985) *Nature* 314: 446-49, Shaw et al. (1988) *J. Natl. Cancer Inst.* 80: 1553-59, Morrison, (1985) *Science* 229: 1202-07, Oi et al. (1986) *BioTechniques* 4: 214, Jones et al. (1986) *Nature* 321: 552-25, Veroeyan et al. (1988) *Science* 239: 1534; and Beidler et al. (1988) *J. Immunol.* 141: 4053-60.

Also included within the scope of the invention are antibody fragments and derivatives which contain at least the functional portion of the antigen binding domain of an antibody that binds specifically to 4-1BB. Antibody fragments that contain the binding domain of the molecule can be generated by known techniques. For example, such fragments include, but are not limited to: F(ab')$_2$ fragments that can be produced by pepsin digestion of antibody molecules; Fab fragments that can be generated by reducing the disulfide bridges of F(ab')$_2$ fragments; and Fab fragments that can be generated by treating antibody molecules with papain and a reducing agent (see, e.g., National Institutes of Health, *Current Protocols In Immunology*, Coligan et al. ed. 2.8, 2.10 (Wiley Interscience, 1991). Antibody fragments also include Fv (e.g., single chain Fv (scFv)) fragments, i.e., antibody products in which there are few or no constant region amino acid residues. An scFv fragment is a single polypeptide chain that includes both the heavy and light chain variable regions of the antibody from which the ScFv is derived. Such fragments can be produced, for example, as described in U.S. Pat. No. 4,642,334.

3.3 The Cells

Preferred cells are those with a defined major histocompatibility complex (MHC) genomic region or equivalent and with the capability of increasing or enhancing class I MHC presentation of antigenic molecules to cell surfaces.

The cells of the present invention may be derived from the intended host, treated and then re-introduced or reinfused into that host. It is particularly convenient to use cells derived from the host to be treated, either by surgical resection, biopsy, blood sampling, or other suitable technique. Such cells are referred to herein as "autologous" cells. Alternatively, cells or cell lines (e.g., tumor cell lines) may be prepared and/or cultured from one source and introduced into a different host. Such cells include "syngeneic" and "allogeneic" cells. One particular form of allogeneic cells comprises a generic cell line with shared major and/or minor histocompatibility antigens to potential recipients.

Suitably, the generic cell line naturally expresses the B7 molecule, preferably a B7 membrane molecule, at levels sufficient to trigger an immune response, preferably a T cell immune response, and more preferably a cytotoxic T lymphocyte immune response, in the intended host.

It is preferred the generic cell line comprises MHC class I antigens compatible with a high percentage of the population that is susceptible or predisposed to a particular condition. Suitably, the condition being treated or prevented by vaccination is a cancer or tumor. Preferably, the generic cell line expresses high levels of an endogenous B7 molecule. It is also preferred that the generic cell line is highly susceptible to treatment with at least one IFN as described herein (i.e., implied high level expression of class I HLA).

In one embodiment, the artificial antigen presenting cells (e.g., cancer cells) or cell lines are suitably rendered inactive to prevent further proliferation once administered to the subject. Any physical, chemical, or biological means of inactivation may be used, including but not limited to irradiation (preferably with at least about 5,000 cGy, more preferably at least about 10,000 cGy, more preferably at least about 20,000 cGy); or treatment with mitomycin-C (preferably at least 10 μg/mL; more preferably at least about 50 μg/mL).

The present invention extends to animal cells derived from, for example, avian species, reptiles and mammals. Mammals are preferred and include humans, livestock animals (e.g., sheep, cows, horses, pigs), laboratory test animals (e.g., mice, rats, rabbits, guinea pigs), companion animals (e.g., cats, dogs) and captive wild animals (e.g., kangaroos, deer, foxes). Humans are the most preferred animals and both autologous and allogeneic cells may be employed in human subjects.

The animal cells are preferably derived from animal cells. Preferably, the artificial antigen presenting cells, or compositions in accordance with the present invention are derived from tumor or cancer cells. For example, in the treatment of melanoma in accordance with the practices of this invention, the melanoma cells would be treated as described hereinabove to produce a melanoma antigen presenting cell or composition. Similarly, breast tumor or cancer cells, prostate cancer cells, colon cancer cells, lung cancer, pancreas cancer cells, stomach cancer cells, bladder cancer cells, kidney cancer cells and the like would be produced and employed as immunotherapeutic agents in accordance with the practices for the prevention and/or treatment of the tumor or cancer cell from which the cells or composition according to the invention was produced. In a preferred embodiment, the animal cells are selected from melanoma cells.

3.4 IFN Pretreatment

The step of generating the artificial antigen presenting cells includes culturing said cells with at least one type I interferon and/or a type II interferon. The at least one type I interferon is preferably selected from IFN-alpha, an IFN-beta or biologically active fragments thereof. Preferably, the type II interferon is selected from IFN-gamma or biologically active fragments thereof.

Suitably, the IFN-gamma comprises the amino acid sequence (UniProt Accession No. P01579):

[SEQ ID NO: 5]
MKYTSYILAFQLCIVLGSLGCYCQDPYVKEAENLKKYFNAGHSDVADNGT

LFLGILKNWKEESDRKIMQSQIVSFYFKLFKNFKDDQSIQKSVETIKEDM

NVKFFNSNKKKRDDFEKLTNYSVTDLNVQRKAIHELIQVMAELSPAAKTG

KRKRSQMLFRGRRASQ.

In one embodiment, the IFN-beta is an IFN-beta 1, which suitably comprises the amino acid sequence set forth in SEQ ID NO: 6 (UniProt Accession No. P01574). In an alternate embodiment, the IFN-beta is an IFN-beta 2, which preferably comprises the amino acid sequence set forth in SEQ ID NO: 7, presented below:

[SEQ ID NO: 6]
MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRN;
and,

[SEQ ID NO: 7]
MNSFSTSAFGPVAFSLGLLLVLPAAFPAPVPPGEDSKDVAAPHRQPLTSS

ERIDKQIRYILDGISALRKETCNKSNMCESSKEALAENNLNLPKMAEKDG

CFQSGFNEETCLVKIITGLLEFEVYLEYLQNRFESSEEQARAVQMSTKVL

IQFLQKKAKNLDAITTPDPTTNASLLTKLQAQNQWLQDMTTHLILRSFKE

FLQSSLRALRQM.

For example, IFN-alpha and/or IFN-beta may be used directly on the cells or the cells may first be cultured in the presence of IFN-gamma prior to treatment with IFN-alpha and/or IFN-beta. Although not intending to limit the present invention to any one theory or particular mode of action, it is proposed this IFN-gamma restores or enhances levels of transcriptional factors required for transcriptional activation of genes regulated by IFN-alpha and IFN-beta.

Accordingly, the step of culturing preferably comprises contacting said cells with a type II IFN for a time and under conditions sufficient to permit cellular responsiveness to at least one type I interferon and then contacting said cultured cells with the at least one type I IFN for a time and under conditions to enhance the antigen presenting function of said cells.

In one embodiment, the cells cultured in the presence of the type II IFN are contacted with a type I IFN selected from an IFN-beta or a biologically active fragment thereof.

In another embodiment, the cells cultured in the presence of the type II IFN are contacted with a type I IFN selected from an IFN-alpha or a biologically active fragment thereof.

In yet another embodiment, the cells cultured in the presence of the type II IFN are contacted with a first type I IFN selected from an IFN-beta or a biologically active fragment thereof, and a second type I interferon selected from an IFN-alpha or a biologically active fragment thereof.

Suitably, the cells are cultured with a type II IFN (e.g., IFN-gamma), from about 16 to about 96 hours and subsequently with one or more type I interferons (e.g., IFN-alpha and/or IFN-beta) from about 16 to about 72 hours. Preferably, the cells are cultured with a type II IFN (e.g., IFN-gamma) from about 48 to about 96 hours and subsequently with one or more type I interferons (e.g., IFN-alpha and/or IFN-beta) from about 24 to about 72 hours.

The cells may be treated with IFN-gamma at a concentration of about 100 to about 2000 international units/mL and subsequently with IFN-alpha and/or IFN-beta at a concentration of about 100 to about 2000 international units/mL. Preferably, the cells are cultured with IFN-gamma at a concentration of about 1000 international units/mL and subsequently with IFN-alpha and/or IFN-beta at a concentration of about 1000 international units/mL.

It will be appreciated that the animal cells are, therefore, subjected to at least one IFN in concentrated form unattainable in a recipient host. Not wishing to be bound by any one particular theory or mode of action, the culturing in the presence of the at least one IFN potentiates both the ability of the animal cells to process antigens via antigen processing pathways and to present the processed antigens on the cell surface. The presence of the B7 molecule on the surface of the animal cells provides the means to effect T cell activation through, for example, the CD28 or CTLA4 receptors present on T cells.

In some embodiments, the step of culturing further comprises expanding the population of isolated cells in culture. Such expansion techniques are known to those of skill in the art. For example, the expanded population of cells as described infra is prepared from isolated cells grown in flasks. The production of the expanded population can, if desired, be scaled up by culturing the cells in bioreactors or fermenters or other such vessels or devices suitable for the growing of cells in bulk. The isolated population is preferably expanded in the presence of suitable complete growth media (for example, RPMI OR DMEM containing 10% foetal calf sera or serum free media) in the presence of one or more cytokines/growth factors including, but not restricted to, fibroblast growth factor, at 37° C., 5-7% carbon dioxide.

4. Immunopotentiating Compositions

The invention provides in another aspect a composition for enhancing an immune response, including a cellular (e.g., a T cell including a CD8$^+$ T cell) response and/or humoral immune to a target antigen, comprising the artificial antigen presenting cells described above and elsewhere herein and one or more of a pharmaceutically acceptable carrier, diluent and/or adjuvant. Specifically, the cells included in the composition comprise culturing animal cells with at least one interferon for a time and under conditions sufficient to enhance the antigen presenting function of the cells, wherein the cells express on their surface, or are otherwise provided in combination, a B7 molecule and a 4-1BB agonist. Typically, the cells are washed to remove any one or more of culture medium and IFN(s).

In some embodiments, the B7 molecule is expressed by the animal cell, to be presented on the cell surface. In alternate embodiments, the B7 molecule is suitably in soluble form. In a preferred embodiment of this type, the B7 protein is a B7 molecule that lacks a functional transmembrane domain. Preferably, the soluble B7 molecule comprises a B7 extracellular domain. Soluble B7.1 molecules of this type are disclosed, for example, by McHugh et al. (1998, *Clin. Immunol. Immunopathol.* 87(1): 50-59), Faas et al. (2000, *J. Immunol.* 164(12): 6340-6348) and Jeannin et al. (2000, *Immunity* 13(3): 303-312). In another preferred embodiment of this type, the B7 protein is a B7 fusion protein. The B7 fusion protein suitably comprises a B7 molecule, or biologically active fragment thereof, linked together with an antigen-binding molecule which is preferably an antibody or antibody fragment.

In some of the same and different embodiments, the 4-1BB agonist is expressed by the animal cell, to be presented on the cell surface. In alternate embodiments of this type, the 4-1BB agonist is suitably in soluble form. In a preferred embodiment of this type (i.e. soluble protein), the 4-1BB agonist is a proteinaceous molecule that lacks a functional transmembrane domain. Soluble 4-1BB agonists, for example, the soluble 4-1BBL polypeptide published by Won et al., J Biol Chem. 2010 Mar. 19; 285(12):9202-10. In some embodiments, the 4-1BB agonist is a fusion protein comprising a 4-1BB agonist, or biologically active fragment thereof, linked together with an antigen-binding molecule, which is preferably an antibody or antibody fragment.

Preferred fusion proteins (also commonly known as "chimeric proteins" or "chimeric molecules") in accordance with the present invention comprise a polypeptide corresponding to a biologically active fragment of a B7 molecule, or a 4-1BB agonist. For example, a B7 chimeric molecule useful in the present invention is a B7Ig fusion protein that comprises a polypeptide corresponding to the extracellular domain of the B7 molecule and an immunoglobulin constant region that alters the solubility, affinity and/or valency of the B7 molecule.

In preferred embodiments, a polynucleotide encoding the amino acid sequence corresponding to the extracellular domain of the B7.1 molecule, containing amino acids from about position 1 to about position 215, is joined to a polynucleotide encoding the amino acid sequences corresponding to the hinge, CH2 and CH3 regions of human Ig Cγ1, using PCR, to form a construct that is expressed as a B7Ig fusion protein. DNA encoding the amino acid sequence corresponding to a B7Ig fusion protein has been deposited with the American Type culture Collection (ATCC) in Rockville, Md., under the Budapest Treaty on May 31, 1991 and accorded accession number 68627. Techniques for making and assembling such B7 derivatives are disclosed for example by Linsley et al. (U.S. Pat. No. 5,580,756). Reference also may be made to Sturmhoefel et al. (1999, *Cancer Res.* 59: 4964-4972) who disclose fusion proteins comprising the extracellular region of B7.1 or B7.2 fused in frame to the Fc portion of IgG2a.

In preferred embodiments, the soluble 4-1BB agonist is a 4-1BBL construct.

The half-life of a soluble proteins may be prolonged by any suitable procedure if desired. Preferably, such molecules are chemically modified with polyethylene glycol (PEG), including monomethoxy-polyethylene glycol, as for example disclosed by Chapman et al (1999, *Nature Biotechnology* 17: 780-783).

One particular advantage of the present invention is that no predetermined selection of the types of antigens presented on the cells occurs since the cells are used as a source of immunogen. Accordingly, a large array of the antigens normally processed by the cells will be available to activate immune cell processes, resulting in a wide variation in the populations of responding immune cells to the range of different antigenic targets. By way of example, a cancer cell will expresses multiple tumor-associated antigens shared by the tumor of a patient to be treated.

Furthermore, antigens are presented in the configuration evolved through natural selection, which is used by antigen presenting cells and, hence, provides for strong immune cell activation. Alternatively, treated cells may be loaded with particular antigenic peptides, which are preferably tumor antigens, to yield specific targeted vaccines. For example, reference may be made to Van Pel et al (1995, *Immunol Rev* 145: 229-50) who describe various genes encoding tumor antigens recognised by CTL. Reference also may be made to Itoh et al (1994, *J. Immunol.* 153: 1202-1215) and Cole et al (1995, *Cancer Res.* 55: 748-752) who describe the use of loading peptides on tumor cells as targets for CTL killing.

The compositions according to the invention can also be prepared to treat various infectious diseases that affect humans and animals by loading antigens of a pathogenic organism (e.g., viral, bacterial, fungal, protozoan) onto the treated cells. As there is heterogeneity in the type of immunogenic and protective antigens expressed by different varieties of organisms causing the same disease, polyvalent compositions and vaccines could be prepared by preparing the composition or vaccine from a pool of organisms expressing the different antigens of importance. The invention, therefore, also encompasses a method for stimulating a patient's immune system, and preferably for modulating the T cell response of the patient to one or more antigens by administering to the patient animal cells cultured in the presence of at least one interferon (IFN) for a time and under conditions sufficient to enhance the antigen presenting functions of said cells, together with the or each antigen. Even more preferably, the T cell response is a CD8$^+$ T cell response. Accordingly, the immunogenicity of an antigen can be enhanced or otherwise improved in vitro, by isolating animal cells from a subject, "pulsing" or contacting them with the antigen, then using the pulsed cells to stimulate autologous T cells in vitro or in vivo.

The compositions according to the invention can be prepared to treat immunocompromised animals that may be suffering or have a propensity to suffer from bacterial, viral or yeast infection, protozoan or other parasite infection or have a cancer such as melanoma or other sarcoma or tumor.

The animal cells in combination with the B7 molecule and 4-1BB agonist described above can be used as actives for the treatment or prophylaxis of various conditions as, for example, a tumor or cancer. These therapeutic agents can be administered to a patient either by themselves or in immune-potentiating compositions where they are mixed with one or more pharmaceutically acceptable carriers, adjuvants and/or diluents.

The immune-potentiating compositions of the present invention. can be prepared using routine methods known to persons skilled in the art. Typically, such compositions are prepared as injectables, either as liquid solutions or suspensions; solid forms suitable for solution in, or suspension in, liquid prior to injection may also be prepared. The preparation may also be emulsified. The active immunogenic ingredients are often mixed with excipients that are pharmaceutically acceptable and compatible with the active ingredient. Suitable excipients are, for example, water, saline, dextrose, glycerol, ethanol, or the like and combinations thereof. In addition, if desired, the compositions may contain minor amounts of auxiliary substances such as wetting or emulsifying agents, pH buffering agents, and/or adjuvants that enhance the effectiveness of the compositions. Examples of adjuvants which may be effective include but are not limited to: aluminium hydroxide, N-acetyl-muramyl-L-threonyl-D-isoglutamine (thur-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 1983A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Preferably, the adjuvant is selected from the group comprising galectin inhibitors, monoclonal antibodies against immunosuppressive inhibitors such as CTLA4, PD1, PD-L1, indole dioxygenase (IDO), and TGF-beta inhibitors. For example, the effectiveness of an adjuvant may be determined by measuring the amount of antibodies resulting from the administration of the composition, wherein those antibodies are directed against one or more antigens presented by the treated cells of the composition.

The cells are typically administered in a pharmaceutically acceptable carrier, which is non-toxic to the cells and the individual. Such carrier may be the growth medium in which the cells were grown. Compatible excipients include isotonic saline, with or without a physiologically compatible buffer like phosphate or Hepes and nutrients such as dextrose, physiologically compatible ions, or amino acids, and various culture media suitable for use with cell populations, particularly those devoid of other immunogenic components. Carrying reagents, such as albumin and blood plasma fractions and nonactive thickening agents, may also be used. Non-active biological components, to the extent that they are present in the vaccine, are preferably derived from a syngeneic animal or human as that to be treated, and are even more preferably obtained previously from the subject. The injection site may be subcutaneous, intraperitoneal, intramuscular, intradermal, or intravenous.

If a soluble immunostimulatory molecule is employed as an active in the composition, the immunostimulatory molecule can be formulated into the composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

If desired, devices or compositions containing the animal cells of the present invention are suitable for sustained or intermittent release and could be, in effect, implanted in the body or topically applied thereto for the relatively slow release of such materials into the body.

It will be appreciated that the soluble immunostimulatory molecule may be administered to a patient separately to the administration of the cell-containing composition. Depending on the specific conditions being treated, the immunostimulatory molecule may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The number of IFN-treated cells and optionally the quantity of the immunostimulatory molecule to be administered may depend on the subject to be treated inclusive of the age, sex, weight and general health condition thereof. In this regard, precise amounts of the agent(s) for administration will depend on the judgment of the practitioner. In determining the effective amount of the agent(s) to be administered in the treatment of a disease or condition, the physician may evaluate the progression of the disease or condition over time. In any event, those of skill in the art may readily determine suitable dosages of the agents of the invention without undue experimentation. Cell-containing compositions and vaccines are suitably administered to a patient in the range of between about $10^4$ and $10^{10}$, and more preferably between about $10^6$ and $10^8$ treated cells/administration. The dosage of the immunostimulatory molecule administered to a patient should be sufficient in combination with the cellular component of the vaccine to effect a beneficial response in the patient over time such as a reduction in the symptoms associated with the cancer or tumor. Dosage amount and interval may be adjusted individually to provide plasma levels of the immunostimulatory molecule which are sufficient to maintain immunostimulatory effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day.

5. Methods of Treatment and Prophylaxis

Also encapsulated by the present invention is a method for treatment and/or prophylaxis of a disease or condition, comprising administering to a patient in need of such treatment an effective amount of a cell or composition as broadly described above and elsewhere herein.

In one embodiment, the cell or composition of the invention could also be used for generating large numbers of CD8$^+$ or CD4$^+$ CTL, for adoptive transfer to immunosuppressed individuals who are unable to mount normal immune responses. For example, antigen-specific CD8$^+$ CTL can be adoptively transferred for therapeutic purposes in individuals afflicted with HIV infection (Koup et al. 1991, J. Exp. Med. 174: 1593-1600; Carmichael et al. 1993, J. Exp. Med. 177: 249-256; and Johnson et al. 1992, J. Exp. Med.

175: 961-971), malaria (Hill et al. 1992, *Nature* 360: 434-439) and malignant tumors such as melanoma (Van der Brogen et al. 1991, *Science* 254: 1643-1647; and Young and Steinman 1990, *J. Exp. Med.,* 171: 1315-1332).

5.1 Treatment and Prophylaxis of a Cancer or Tumor

In accordance with the present invention, it is proposed that cells and compositions that include a B7 molecule and that agonize 4-1BB find utility in the treatment or prophylaxis of a tumor or cancer. The cells and compositions of the present invention may be used therapeutically after a cancer or tumor is diagnosed, or may be used prophylactically before the a subject develops a cancer or tumor. Cancers or tumors which could be suitably treated in accordance with the practices of this invention include cancers or tumors of the lung such as small and large cell adenocarcinomas, squamous cell carcinoma, and brionchoalveolar carcinoma; breast tumors, such as ductal and lobular adenocarcinoma; gynecologic tumors, such as squamous and adenocarcinoma of the uterine cervix, and uterine and ovarian epithelial adenocarcinomaovary; colon tumors, such as epithelial adenocarcinoma and their metastases; pancreatic tumors such as pancreatic ductal adenocarcinomas; prostate tumors, such as prostatic adenocarcinoma; stomach; bladder tumors, such as transitional squamous cell carcinoma; kidney, bone, liver tumors, such as hepatoma and cholangiocarcinoma; tumors of the reticuloendothelial (RES) system, such as nodular or diffuse B or T cell lymphoma; plasmacytoma, and acute or chronic leukemia; oesophageal cancer; brain tumors, such as astrocytoma, oligodendroglioma, ependymoma, medulloblastomas, primitive neural ectodermal tumor, gliomas, glioblastomas, and gliosarcomas; testicular tumors; skin tumors, such as malignant melanoma; soft tissue tumors, such as soft tissue sarcoma and leiomyosarcoma; and the various leukemias and lymphomas. In a preferred embodiment, the cancer is melanoma or breast cancer.

The cells and compositions described above and elsewhere herein are particularly suitable for using in prophylactic methods against cancers and/or tumors. Such methods are suitably prime-boost vaccinations against cancers or tumors that induce long-lasting humoral, cell-mediated and mucosal immune responses against the cancer or tumor.

In some embodiments the cells and compositions of the present invention are administered in multiple doses in a prime-boost regimen, with the goal of inducing long-lived potent immunity against a target antigen. Such strategies use a second dose of a of the cell, composition or vaccine to bolster immunity elicited by the priming dose.

Some embodiments of the present invention are based on the realisation that an optimal strategy for eliciting protective immunity against a target antigen involves the generation of both a cellular and a humoral immune response to the target antigen. The invention thus provides a multi-component administration strategy in which a first dose of the cell, composition or vaccine of the present invention primes the immune system by eliciting or inducing a first immune response, and a second dose of the cell, composition or vaccine of the present invention is used to boost or elicit a second immune response, wherein the cell, composition or vaccine administered in the first dose is the same as that administered second cell. In illustrative examples of this type, the first dose is administered to induce largely a cellular immune response to the target antigen, whereas the second dose is administered largely to elicit a humoral immune response to the target antigen. Upon completion of the administration steps of the strategy, both cellular and humoral immune responses develop to the target antigen. The two responses together thus provide effective or enhanced protection against a disease or condition that is associated with the presence of a target antigen, e.g, a cancer or tumor antigen.

In order to maximize the direct stimulation and activation of those $CD8^+$ CTLs that target the relevant antigens, the cell, composition or vaccine used for the prime and boost administrations are, preferentially, the same.

5.2 Treatment Regimens

It is well known that chemotherapy and radiation therapy target rapidly dividing cells and/or disrupt the cell cycle or cell division. These treatments are offered as part of the treating several forms of cancer and autoimmune disease, aiming either at slowing their progression or reversing the symptoms of disease by means of a curative treatment. In some embodiments, therefore, the combination therapy will employ a cell, composition or vaccine that is administered together with a chemotherapeutic agent, which is suitable selected from cytostatic agents and cytotoxic agents. Non-limiting examples of cytostatic agents are selected from: (1) microtubule-stabilizing agents such as but not limited to taxanes, paclitaxel, docetaxel, epothilones and laulimalides; (2) kinase inhibitors, illustrative examples of which include Iressa®, Gleevec, Tarceva™, (Erlotinib HCl), BAY-43-9006, inhibitors of the split kinase domain receptor tyrosine kinase subgroup (e.g., PTK787/ZK 222584 and SU11248); (3) receptor kinase targeted antibodies, which include, but are not limited to, Trastuzumab (Herceptin®), Cetuximab (Erbitux®), Bevacizumab (Avastin™), Rituximab (Ritusan®), Pertuzumab (Omnitarg™); (4) mTOR pathway inhibitors, illustrative examples of which include rapamycin and CCI-778; (5) Apo2L/Trail, anti-angiogenic agents such as but not limited to endostatin, combrestatin, angiostatin, thrombospondin and vascular endothelial growth inhibitor (VEGI); (6) antineoplastic immunotherapy vaccines, representative examples of which include activated T-cells, non-specific immune boosting agents (i.e., interferons, interleukins); (7) antibiotic cytotoxic agents such as but not limited to doxorubicin, bleomycin, dactinomycin, daunorubicin, epirubicin, mitomycin and mitozantrone; (8) alkylating agents, illustrative examples of which include Melphalan, Carmustine, Lomustine, Cyclophosphamide, Ifosfamide, Chlorambucil, Fotemustine, Busulfan, Temozolomide and Thiotepa; (9) hormonal antineoplastic agents, non-limiting examples of which include Nilutamide, Cyproterone acetate, Anastrozole, Exemestane, Tamoxifen, Raloxifene, Bicalutamide, Aminoglutethimide, Leuprorelin acetate, Toremifene citrate, Letrozole, Flutamide, Megestrol acetate and Goserelin acetate; (10) gonadal hormones such as but not limited to Cyproterone acetate and Medoxyprogesterone acetate; (11) antimetabolites, illustrative examples of which include Cytarabine, Fluorouracil, Gemcitabine, Topotecan, Hydroxyurea, Thioguanine, Methotrexate, Colaspase, Raltitrexed and Capicitabine; (12) anabolic agents, such as but not limited to, Nandrolone; (13) adrenal steroid hormones, illustrative examples of which include Methylprednisolone acetate, Dexamethasone, Hydrocortisone, Prednisolone and Prednisone; (14) neoplastic agents such as but not limited to Irinotecan, Carboplatin, Cisplatin, Oxaliplatin, Etoposide and Dacarbazine; and (15) topoisomerase inhibitors, illustrative examples of which include topotecan and irinotecan.

Illustrative cytotoxic agents can be selected from sertenef, cachectin, ifosfamide, tasonermin, lonidamine, carboplatin, altretamine, prednimustine, dibromodulcitol, ranimustine, fotemustine, nedaplatin, oxaliplatin, temozolomide (TEMODAR™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycarminomycin, annamycin, galarubicin, elinafide, MEN10755, 4-demethoxy-3-deamino-3-aziridinyl-4-methylsulphonyl-daunombicin (see International Publication WO 00/50032), methoxtrexate, gemcitabine, and mixture thereof.

Radiotherapies include radiation and waves that induce DNA damage for example, γ-irradiation, X-rays, UV irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

Chemotherapeutic agents may be selected from any one or more of the following categories:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyridines like 5-fluorouracil and tegafur, raltitrexed, methotrexate, cytosine arabinoside and hydroxyurea; anti-tumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and docetaxel; and topoisomerase inhibitors (for example epipodophyllotoxins like etoposide and teniposide, amsacrine, topotecan and camptothecin);

(ii) cytostatic agents such as antiestrogens (for example tamoxifen, toremifene, raloxifene, droloxifene and idoxifene), oestrogen receptor down regulators (for example fulvestrant), antiandrogens (for example bicalutamide, flutamide, nilutamide and cyproterone acetate), UH antagonists or LHRH agonists (for example goserelin, leuprorelin and buserelin), progestogens (for example megestrol acetate), aromatase inhibitors (for example as anastrozole, letrozole, vorozole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

Immunotherapy approaches, include for example ex vivo and in vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

Typically, therapeutic agents as described for example above will be administered in pharmaceutical compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner. In determining the effective amount of the active compound(s) to be administered in the treatment or prevention of a cancer or tumor, the medical practitioner may evaluate severity of any symptom associated with the presence of the cancer or tumor including the presence of lumps, sores that do not heal, sore throats that do not go away, difficulty in swallowing, a change or hoarseness in voice, inflammation, etc. In any event, those of skill in the art may readily determine suitable dosages of the therapeutic agents and suitable treatment regimens without undue experimentation.

The effectiveness of the immunization may be assessed using any suitable technique. For example, CTL lysis assays may be employed using stimulated splenocytes or peripheral blood mononuclear cells (PBMC) on peptide coated or recombinant virus infected cells using $^{51}Cr$ or Alamar Blue™ labeled target cells. Such assays can be performed using for example primate, mouse or human cells (Allen et al., 2000, *J. Immunol.* 164(9): 4968-4978 also Woodberry et al., infra). Alternatively, the efficacy of the immunization may be monitored using one or more techniques including, but not limited to, HLA class I tetramer staining—of both fresh and stimulated PBMCs (see for example Allen et al., supra), proliferation assays (Allen et al., supra), ELISPOT assays and intracellular IFN-gamma staining (Allen et al., supra), ELISA Assays—for linear B cell responses; and Western blots of cell sample expressing the synthetic polynucleotides.

In some embodiments, the therapy or combination therapy described above, also includes other adjuvants to overcome the immune evading mechanisms of cancers. In some embodiments suitable adjuvants for this purpose are selected from the group consisting of: galectin inhibitors, monoclonal antibodies against immunosuppressive inhibitors such as CTLA4, PD1, PD-L1, indole dioxygenase (IDO), TGF-beta inhibitors, and other immune response evasion methods (see, for example, JP Allison's reviews and papers).

5.3 Pathogenic Infection Vaccine

In yet another embodiment, the cell, composition or vaccine is suitable for treatment or prophylaxis of a viral, bacterial or parasitic infection. Viral infections contemplated by the present invention include, but are not restricted to, infections caused by HIV, Hepatitis, Influenza, Japanese encephalitis virus, Epstein-Barr virus and respiratory syncytial virus. Bacterial infections include, but are not restricted to, those caused by *Neisseria* species, *Meningococcal* species, *Haemophilus* species *Salmonella* species, *Streptococcal* species, *Legionella* species and *Mycobacterium* species. Parasitic infections encompassed by the invention include, but are not restricted to, those caused by *Plasmodium* species, *Schistosoma* species, *Leishmania* species, *Trypanosoma* species, *Toxoplasma* species and *Giardia* species.

It is known that infection with a virus can cause depletion of antigen presenting cells (including dendritic cells) in individuals. For example, HIV seropositive individuals have been observed to possess a depleted number of DC in peripheral blood, and surviving DC are dysregulated as a result of infection with the HIV genome (see, Macatonia et al, 1990). Particularly, infection of the DC with HIV blocks the capacity of these cells to induce responses to other antigens (see, Macatonia et al., 1989).

Accordingly, in some embodiments of the invention, the immunomodulatory compositions as described above and elsewhere herein are used to replace the need for a healthy population of dendritic cells (DC) in a subject. As such, the immunomodulatory compositions and methods of the present invention are particularly suitable for treatment and/or prophylaxis of the many virus infections (such as HIV), that result in DC depletion, and the immunomodulatory compositions of the present invention are particularly useful for the treatment of such virus infections.

Furthermore, the present invention is also applicable to the treatment and/or prophylaxis of ancillary indications that are associated with a virus infection. By way of an illustrative example, subjects suffering from an HIV infection are observed to have a significantly weakened immune system, resulting in an increased risk of developing certain cancers. In this regard, individuals suffering from acquired immunodeficiency syndrome (AIDS; a later stage of HIV infection) Kaposi's sarcoma (KS) often develops. Accordingly, in some embodiments the immunomodulatory compositions of the present invention are for use in treating or preventing the development of a HIV-associated disease and/or condition (e.g., Kaposi's sarcoma).

6. Methods for Assessing Cytotoxic T Lymphocyte Activity

The cytotoxic activity of T lymphocytes may be assessed by any suitable technique known to those of skill in the art. For example, a sample comprising T lymphocytes to be assayed for cytotoxic activity is obtained and the T lymphocytes are then exposed to IFN-treated target cells (i.e., a according to the invention. After an appropriate period of time, which may be determined by assessing the cytotoxic activity of a control population of T lymphocytes which are known to be capable of being induced to become cytotoxic cells, the T lymphocytes to be assessed are tested for cytotoxic activity in a standard cytotoxic assay. Such assays may include, but are not limited to, the chromium release CTL assay and the ALAMAR BLUE™ fluorescence assay known in the art.

The method of assessing CTL activity is particularly useful for evaluating an individual's capacity to generate a cytotoxic response against cells expressing tumor or antigens of a pathogenic organism (e.g., viral antigens). Accordingly, this method is useful for evaluating an individual's ability to mount an immune response against a cancer or a pathogenic organism.

The invention also contemplates the use of IFN treatment in accordance with the teachings of the present invention to enhance the sensitivity of detecting cytolytic T lymphocyte (CTL) mediated lysis of a target cell. Accordingly, IFN treatment of a target cell can be used advantageously to develop assays with improved sensitivity for detecting an immune response, particularly a CTL response, and more particularly a CD8+ CTL response, against that target cell.

7. Kits

Any of the compositions or components described herein may be comprised in a kit. In non-limiting examples, materials and reagents required for detecting and determining the levels of one or more glycospecies biomarker described herein may be assembled together in a kit. The kits may also optionally include appropriate reagents for detection of labels, positive and negative controls, washing solutions, blotting membranes, microtiter plates, dilution buffers and the like.

The kits will thus comprise, in suitable container means, a lectin-binding immunosorbent assay may include a lectin specific for the glycospecies biomarker to be detected, an antibody specific for the glycospecies biomarker (i.e., specific for the polypeptide backbone of the glycosylation), and optionally a glycospecies biomarker, which may be used as a positive control. Also included may be buffers, wash solutions or blocking reagents, and enzymes and/or substrates for detection of labels. The kit can also feature various devices and reagents for performing one of the assays described herein, and/or printed instructions for using the kit to determine the level of a glycospecies biomarker.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

A kit will generally also include instructions for employing the kit components as well the use of any other reagent not included in the kit. Instructions may include variations that can be implemented.

The kit may comprise additional components to assist in performing the methods of the present invention such as, for example, administration device(s), buffer(s), and/or diluent(s). The kits may include containers for housing the various components and instructions for using the kit components in the methods of the present invention.

In order that the invention may be readily understood and put into practical effect, particular preferred embodiments will now be described by way of the following non-limiting examples.

EXAMPLES

Example 1

Development of Three Highly Immunogenic Vaccine Cell Lines

Generation of B16-F10/4-1BBL Cells

After developing pEFIRES-Puro/4-1BBL vector and pEF-MC1neoN9/B7.1 expression constructs they were transfected into the B16-F10 cells. Although the transfection efficiency and resistance during antibiotic selection were observed to be very effective, the transfected cells were sorted using the BD FACSAria to further increase the level of expression and to eliminate the more weakly expressing cells. After cell sorting, the top 2% of highly expressing cells were collected and cultured in the presence of puromycin. Antibody staining of the transfected cells with the PE-conjugated anti-mouse 4-1BBL antibody (Ab) demonstrated that the pEFIRES-Puro/4-1BBL construct upregulated intact 4-1BBL molecules on the cell surface detectable by Ab binding. The AB was also used to stain untransfected B16-F10 cells, which revealed that the wild-type cells already expressed low levels of this molecule compared to background. From the mean fluorescence intensities (MFI) of each of the histograms, the fold increase from each histogram was calculated (see, Table 2).

TABLE 2

| Sample | Fold increase compared to isotype control |
|---|---|
| B16-F10 | 3 |
| B16-F10/4-1BBL pre-sort | 477 |
| B16-F10/4-1BBL sort 1 | 1104 |

To further test that the 4-1BBL expressed on the B16-F10/4-1BBL cells was intact and functional, an additional assay was performed for the binding of 4-1BBL on the cells to its receptor, 4-1BB. This was performed by incubating both the transfected or wild type B16-F10 cells with or without a 4-1BB/TNFRSF9/Fc Chimera and then using a PE-conjugated IgG Fcγ Ab for detection of the chimeric 4-1BB using flow cytometry. The results of the assay are shown in FIG. 2.

Figure 2:
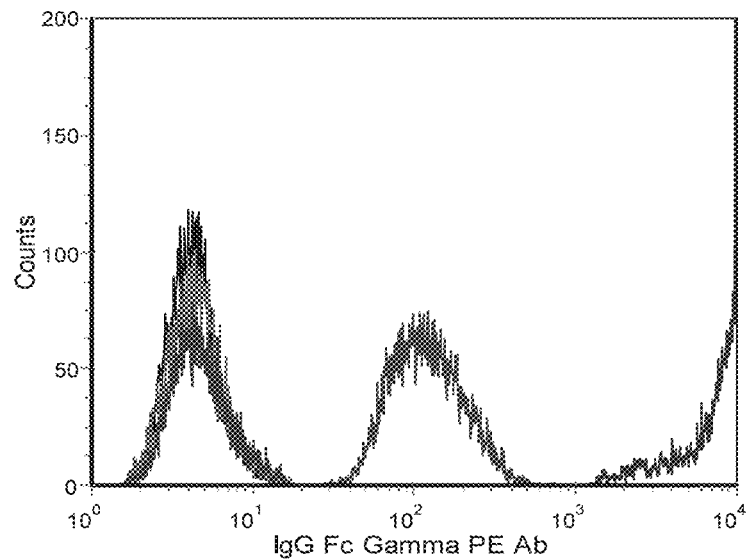
FIG. 2. B16-F10-4-1BBL cells express functional 4-1BBL binding to 4-1BB. Cells were incubated with 41BB/TNFRSF9/Fc chimera and stained using a PE-conjugated IgG Fcγ Ab to detect binding to 4-1BBL, measured using the FACSCalibur flow cytometer. The black and the green histograms represent the unstained control samples of B16-F10 and B16-F10-4/1BBL sorted cells respectively. The red and the purple histograms show the B16-F10 and B16-F10/4-1BBL cells respectively stained only with the IgG Fcγ PE secondary Ab. The blue histogram represents the B16-F10 cells incubated with the 4-1BB/TNFRSF9/Fc Chimera and stained with the IgG Fcγ PE secondary Ab. The maroon histogram depicts populations of cells further subjected to sorting for 4-1BBL, re-expanded in culture before immunostaining with the 41BB/TNFRSF9/Fc chimera and the IgG Fcγ PE secondary Ab FIG. 3. (A) Enhanced expression of B7.1 on B16-F10/B7.1 cells following repeated rounds of cell sorting and selection. Flow cytometric analysis was performed to determine the levels of B7.1 expression on wild type B16-F10 cells compared to cells transfected with the pEF-MC1neoN9/B7.1 vector. All cells from the various sublines were stained with the PE-conjugated rat anti-mouse CD80 Ab and analysed using the BD FACSCalibur. The samples were gated to represent the majority of the positively stained cell populations. The black histogram represents the first group of B16-F10/B7.1 (sort 1) cells stained with a PE isotype control. The red histogram shows the expression profile of B7.1 on wild type B16-F10 cells. The blue histogram shows the level of B7.1 expressed on the cells following transfection. The green, purple and maroon coloured histograms show the level of B7.1 expressed after the cells had been repetitively sorted on the BD FACSAria after one, two and three rounds respectively. (B) High expression of B7.1 on B16-F10/B7.1 cells developed and maintained after clonal selection. The black histogram represents isotype stained B16-F10/B7.1 sort 3 cells. The green histogram shows the B7.1 expression on B16-F10/B7.1 sort 3 cells. The dark blue, yellow and maroon histograms show the level of B7.1 expressed on B16-F10/B7.1 sort 3 cells, clone 1, clone 2 and clone 3 respectively. B7.1 expression was detected by staining the cells with a PE-conjugated rat anti-mouse CD80 Ab and analysed on the FACSCalibur flow cytometer.

The red and purple histograms in FIG. 2 indicate that the IgG Fcγ PE secondary Ab staining does not display any background binding or cross-react with other molecules on the cells. This conclusion can be made because there was no difference in the histogram profile between the secondary Ab control samples and the two unstained control samples (FIG. 2). However, the B16-F10 wild-type cells incubated with the 4-1BB/TNFRSF9/Fc chimera and stained with the IgG Fcγ PE secondary Ab detected the presence of low levels of 4-1BBL expression indicating that these cells already express some functional 4-1BBL before transfection, consistent with the results in Table 2. The results from the PE-conjugated anti-mouse 4-1BBL Ab together with 4-1BB/TNFRSF9/Fc chimera/IgG Fcγ PE secondary Ab binding of 4-1BB to 4-1BBL, provide evidential support that the cells transfected with the vector encoding the murine 4-1BBL cDNA effectively expressed functional cell surface 4-1BBL molecules.

Generation of B16-F10/4-1BBL Cells

In contrast to the pEFIRES-Puro/4-1BBL vector, the pEF-MC1neoN9/B7.1 vector proved difficult to transfect into the B16-F10 cells. The most effective reagent for transfecting the B16-F10 and B16-F10/4-1BBL cells was Lipofectamine LTX that was used in combination with Plus reagent. The transfection efficiency was much lower than with the pEFIRES-Puro/4-1BBL vector, such that additional rounds of cell sorting were required to select for a stable, highly expressing B7.1 cell line. The B16-F10 cells transfected with the pEF-MC1neoN9/B7.1 vector was renamed as B16-F10/B7.1 and the transfected B16-F10/4-1BBL cells was renamed as B16-F10/4-1BBL-B7.1. The B16-F10/B7.1 cells were subjected to three rounds of sorting and selection on the BD FACSAria and the B16-F10/4-1BBL/B7.1 cells were sorted similarly through five rounds of repetition to ensure uniform, highly stable expressing cell lines. The top 1-5% of expressing cells were collected for both cell lines in every round of sorting and subsequently expanded by culturing with the required antibiotics. The B16-F10/B7.1 cell sorting results are shown in FIG. 3A and Table 3. After each sort, the cells were cultured and expanded until there were sufficient cells that could be analysed on the BD FACSCalibur to assess the efficiency and stability of B7.1 expression using the PE-conjugated anti-mouse CD80 Ab.

TABLE 3

| Sample | Fold increase compared to isotype control |
| --- | --- |
| B16-F10 | 1 |
| B16-F10/B7.1 pre-sort | 4 |
| B16-F10/B7.1 sort 1 | 13 |
| B16-F10/B7.1 sort 2 | 11 |
| B16-F10/B7.1 sort 3 | 24 |

Sorting the B16-F10/B7.1 cells increased the overall B7.1 expression after the first sort to 13-fold greater than the untransfected, parental cells and three-fold greater than the B7.1 expression on transfected, but not sorted, cells. After the third round of sorting, the level of B7.1 expression was increased to 24-fold that of the isotype control or untransfected cell populations. Despite the expression of B7.1 on the cells being much greater than that of the wild-type cells, the population was still not stably expressing the gene even after exposure to high concentration antibiotic selection. The next stage in developing a more stable cell line involved clonal derivation of individual B16-F10/B7.1 cells. Three clones collected from the third round of sorting survived and underwent single cell cloning and were expanded such that their levels of B7.1 expression could be analysed on the BD FACSCalibur (FIG. 3B).

Figure 3:
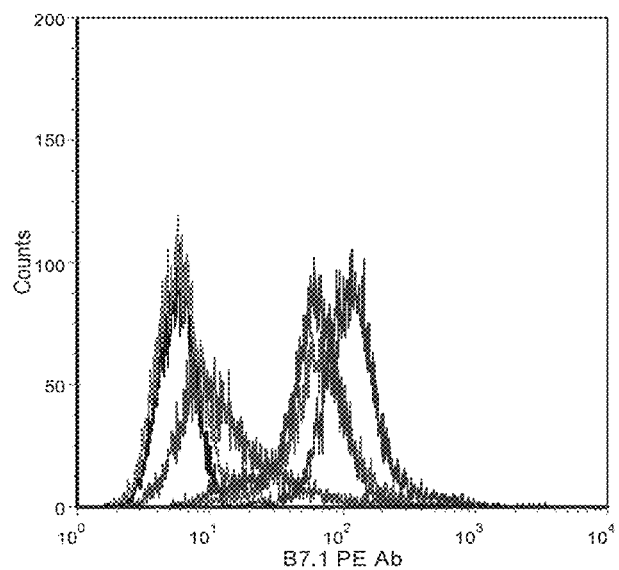
Figure 3:
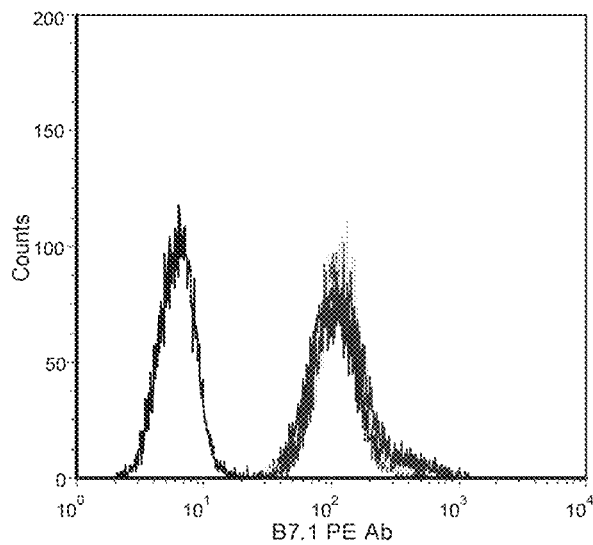

Clonally selecting the B16-F10-B7.1 cells did not further increase the level of B7.1 expression as shown by the histograms in FIG. 3.8. However, after subculturing and passaging these cloned cells over several weeks, it was determined that the level of B7.1 showed much less variation compared to non-clonally sorted parental cell populations. Therefore, clonally sorting the B16-F10-B7.1 cells produced a more stable expressing population. Hence, the same sorting procedures were also applied to the B16-F10-4-1BBL-B7.1 cells. The B16-F10-4-1BBL-B7.1 cells before sorting and after expansion following five rounds of sorting are shown in FIG. 3.9.

Summary of Example

In summary, three vaccine cell lines stably expressing 4-1BBL, B7.1 or both 4-1BBL and B7.1 were successfully generated. An appropriate cell line was derived and chosen for use in challenge experiments and a new CTL assay protocol was developed using the fluorescent dye SYTOX Green. After optimization of the cells and procedures, the three vaccine cell lines were suitably prepared for administration to C57BL/6 mice.

Materials and Methods

Generation of the 4-1BBL Construct

To develop high expressing, stably transfected cell lines, a vector construct encoding 4-1BBL together with a puromycin resistance gene was first generated. A vector containing murine 4-1BBL cDNA cloned into the pcDNA3 vector was used as the starting point. However, in order to be compatible with the experimental 154 design, unique resistance genes for selecting each of the 4-1BBL (puromycin) and B7.1 (neomycin) expression vectors are required.

Two primers were developed that flanked either end of the 4-1BBL cDNA. The forward primer (5'-CTC GAATTCGGTAATGGACCAGCACA-3') was engineered to contain an EcoRI restriction enzyme site (underlined) and the reverse primer (5'-GACAACCCATGGGAATGATGTA-CAGG-3') already contained a XbaI restriction enzyme. A high-fidelity PCR reaction was performed on the pcDNA3 construct containing the full length murine 4-1BBL cDNA using the two newly designed primers and the products were resolved via agarose gel electrophoresis. Upon inspection of the agarose gel, the resolved products were observed to be approximately 1 kb in size, which closely corresponded to the 950 bp length of the 4-1BBL mRNA as determined from the NCBI published gene sequence (Accession Number NM_009404). Following the PCR reaction, the DNA was extracted using kits and then ligated into pGEM-T Easy Vector.

Figure 1:
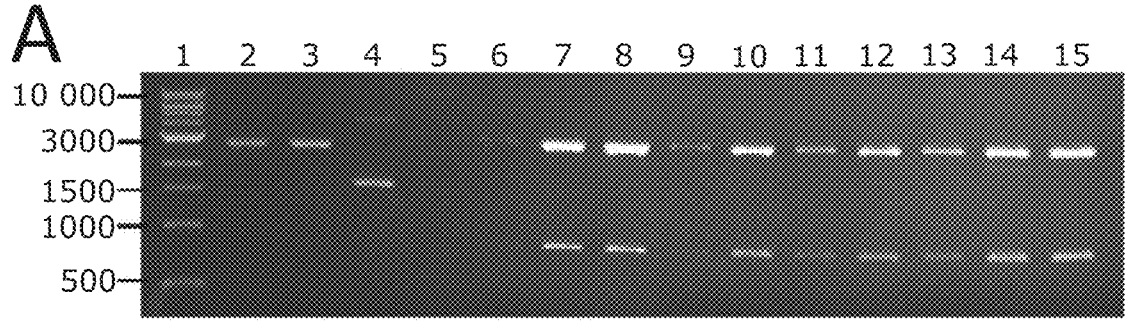
FIG. 1. (A) Screening for bacterial clones containing the 4-1BBL cDNA inserted into the pGEM-T vector. Plasmid DNA was extracted from ten bacterial clones that were expected to contain the appropriately ligated plasmid containing the 4-1BBL transgene. The DNA was double digested using XbaI and EcoRI and electrophoresed on a 1% agarose gel containing 0.5 μg/mL of ethidium bromide. A 1 kb DNA ladder was loaded in lane 1. The pUC18 vector cut with XbaI only, EcoRI only and uncut pUC18 DNA were loaded in lanes 2-4 respectively. A sample of uncut DNA from clone 1 was loaded in lane 5. Lanes 6-15 contained double digested DNA samples from clones 1-10. (B) Screening for bacterial clones containing the 4-1BBL cDNA inserted into the pGEM-T vector. Plasmid DNA was extracted from ten bacterial clones that were expected to contain the appropriately ligated plasmid containing the 4-1BBL transgene. The DNA was double digested using XbaI and EcoRI and electrophoresed on a 1% agarose gel containing 0.5 μg/mL of ethidium bromide. A 1 kb DNA ladder was loaded in lane 1. The pUC18 vector cut with XbaI only, EcoRI only and uncut pUC18 DNA were loaded in lanes 2-4 respectively. A sample of uncut DNA from clone 1 was loaded in lane 5. Lanes 6-15 contained double digested DNA samples from clones 1-10.
Figure 1:
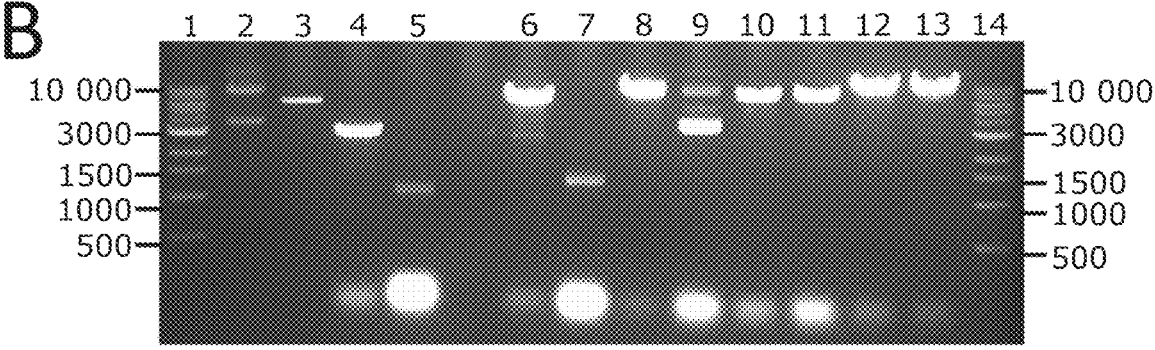
Figure 1:
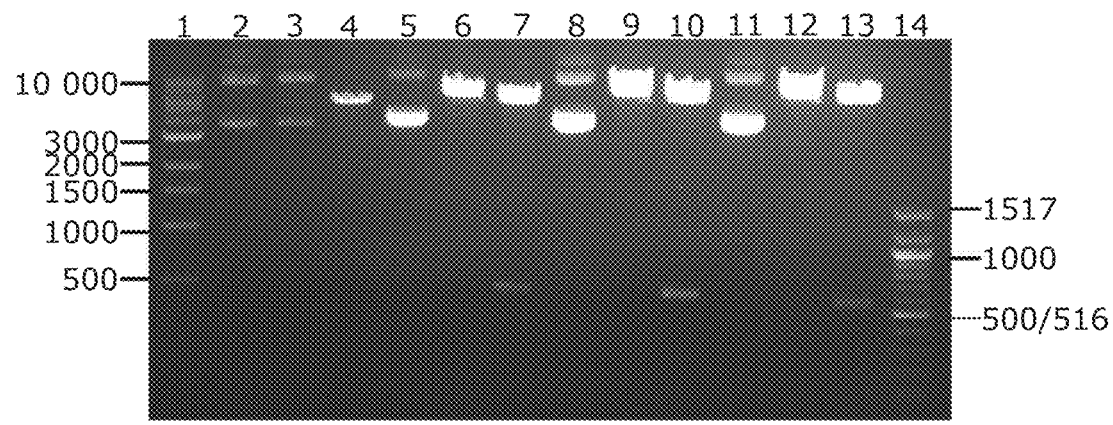

Once the 4-1BBL PCR product was purified and A-tailed using DyNAzyme II DNA polymerase, a ligation reaction of the products with the pGEM-T vector was performed followed by transformation of the ligation reaction into competent DH5α bacteria. In order to confirm the successful ligation of 4-1BBL into pGEM-T, ten white colonies were selected from the Ampicillin agar plates, expanded in culture and the plasmid DNA extracted using Mini-Prep kits. Double digests were then performed on all ten DNA samples using EcoRI and XbaI. Several controls were used to determine that firstly, both 155 enzymes were working when the DNA was cut with each single enzyme alone and multiple cuts when used together and secondly, to determine whether the two enzymes would release the correct sized 4-1BBL fragment of 950 bp in length. The pUC18 vector contains both EcoRI and XbaI restriction enzyme sites and was used as a control vector for digestion. The double digested pGEM-T vector suspected of containing the ligated 4-1BBL fragment and the digested pUC18 vector were electrophoresed on an agarose gel (FIG. 1A). All ten of the double digested clones released a DNA fragment of approximately 1 kb in size. This indicated that the ligation reaction was successful in ligating 4-1BBL into the pGEM-T vector. The double digested DNA of clone 9 that was loaded in lane 14, appeared to have another faint band present between the 3 kb and 2 kb bands, so for precautionary measures clone 9 was not used for further experiments.

The pGEM-T vector containing 4-1BBL cDNA and pEFIRES-Puro vector were digested with XbaI and EcoRI. The digests produced the predicted 950 kb 4-1BBL fragment and a 5689 kb pEFIRES-Puro vector fragment. The 4-1BBL and pEFIRES-Puro fragments were extracted from the agarose gel using kits, purified and ligated together. The products of the ligation reaction were then transformed into competent DH5a. The colonies that grew on the Ampicillin agar plates were picked and the DNA extracted using Mini-Prep kits. DNA from each of the clones was cut with EcoRI to linearize the DNA and loaded onto an agarose gel (FIG. 1B). The bands in lanes 6, 10 and 11 that correspond to clones 3, 7 and 8 all appeared to be of similar size to the backbone vector produced from the double digested pEFIRES-Puro loaded into lane 3. The bands produced from clones 5, 9 and 10 (lanes 8, 12 and 13) migrated slower than the 5689 bp band produced by the double digested pEFIRES-Puro sample in lane 3, suggesting that they each contained a possible insert.

To further test for clones with pEFIRES-Puro vector containing the 4-1BBL insert, another restriction analysis was performed on clones 5, 9 and 10 identified in FIG. 1B to be potential candidates. However, this time the restriction enzymes EcoRI and SacI were selected because according to the vector map, these two sites were only present within the 4-1BBL sequence where they were approximately 500 bp apart. Therefore, if both of the enzymes were able to cut any of the DNA samples to only release a 500 bp fragment, this would help confirm the presence of the 4-1BBL insert within the pEFIRES-Puro vector. The double digest was performed and the samples loaded on an agarose gel (FIG. 1C). Clones 5, 9 and 10 (from lanes 8, 12 and 13 in FIG. 1B) all showed a fragment of approximately 500 bp in length as detected in lanes 7, 10 and 13 in FIG. 1C. Therefore it was highly likely that all three clones contained 4-1BBL cDNA correctly inserted within the pEFIRES-Puro vector.

Example 2

T Cell Immune Responses Induced by Whole Cell Vaccines Differing in B7.1 and 4-1BBL Co-Stimulator Expression The effectiveness of three different whole cell melanoma vaccines engineered to express the key immune co-stimulatory molecules 4-1BBL, B7.1, or a combination of both was investigated. Mice were vaccinated with one of the three irradiated cell vaccine lines and along with control, unvaccinated mice, numerous experiments were performed to evaluate the effectiveness of the different vaccines.

Increased CD8$^+$ T Cell Responses Produced in Mice Receiving Two Doses of the B16-F10/4-1BBL/B7.1-IFNγ/β Whole Cell Vaccine C57BL/6 mice were vaccinated with one of three different irradiated whole cell melanoma vaccines described in the previous Example (B16-F10/4-1BBL/IFNγ/β; B16-F10/B7.1/IFNγ/β; or B16-F10/4-1BBL/B7.1/IFNγ/β). The purpose of comparing the three vaccines was first to establish which particular one of the three vaccines would generate the strongest anti-cancer immune response. Secondly, the aim was to determine whether stronger T cell responses were produced in response to the presence of 4-1BBL alone or 4-1BBL in combination with B7.1 presented on the cell surfaces of the cells formulated in the vaccine, when compared to the B16-F10/B7.1 vaccine first described in the International Patent Application Publication No WO2005/037293.

Initial studies used a prime/boost vaccination protocol involving vaccinating naïve mice twice over a seven day interval before sacrificing the mice four days after the booster injection for subsequent immune analysis. A timeline detailing when the vaccinations were delivered is presented in FIG. 4A. On the day 11 the mice were harvested. The spleen, blood and lymph nodes were collected separately from all of the mice. Spleens were weighed and compared as a basic indicator of whether an immune reaction was occurring (FIG. 4B). Next, cell preparations were analysed and T cell numbers determined by flow cytometry (FIG. 5).

Analysis of the spleen weights showed that the variation between groups was not significant ($p=0.1$). However, a significant difference existed between the control spleens and mice injected with the B16-F10/4-1BBL/B7.1/IFNγ/β vaccine, whose spleen weights were significantly increased ($p<0.05$). Although not significant for the other vaccines tested, there was an increasing trend in the mean weight of spleens compared with control mice.

Analysis of the % T cell subsets showed no change in the CD4$^+$ splenic population, whereas % CD8$^+$ T cells was increased in spleens from mice given the B16-F10/4-1BBL/B7.1/IFNγ/β vaccine compared to control mice or spleens from all other vaccinated groups ($p<0.005$ by post hoc testing; FIG. 5A). Analysis of the % CD8$^+$ T cells within the blood also showed similar significant increases, as well as revealing significantly increased % CD8$^+$ T cells in B16-F10/B7.1/IFNγ/β vaccinated mice compared to the B16-F10/4-1BBL/IFNγ/β vaccinated mice ($p=0.036$), as shown in FIG. 5B. When post hoc tests were performed it was found that the % CD8$^+$ T cells in the blood of mice treated with the B16-F10/4-1BBL/B7.1/IFNγ/β vaccine was significantly greater than for control mice or those treated with the B16-F10/4-1BBL/IFNγ/β vaccine ($p=0.007$ and $p=0.0008$ respectively, FIG. 5B). A decrease in the levels of both CD4$^+$ and CD8$^+$ T cells was detected in the peripheral blood lymphocytes (PBL) from the B16-F10-4-1BBL-IFNγ/β vaccine treated mice compared to all other groups (FIG. 5B). However, only the PBL CD4$^+$ T cell levels were significantly lower in the B16-F10/4-1BBL/IFNγ/β vaccine treated mice compared to control mice or B16-F10/B7.1/IFNγ/β vaccine treated mice ($p<0.05$; FIG. 5B). FIG. 5C showed only minor differences in % CD4$^+$ and CD8$^+$ T cells between all of the treatment groups.

Enhanced CD8+ T Cell Populations in Splenic MLC Antigenically Stimulated with Cancer Vaccine Cells The previous experiment determined that splenic derived CD8+ T cells from B16-F10/4-1BBL/B7.1/IFNγ/β vaccinated mice were greatly increased compared to all other groups. Thus, it was envisaged that these lymphocyte populations could be expanded in mixed lymphocyte culture (MLC) for 3 to 5 days and then analysed for changes in antigenically stimulated CD4+ and CD8+ T cell numbers (FIG. 6).

Figure 5:
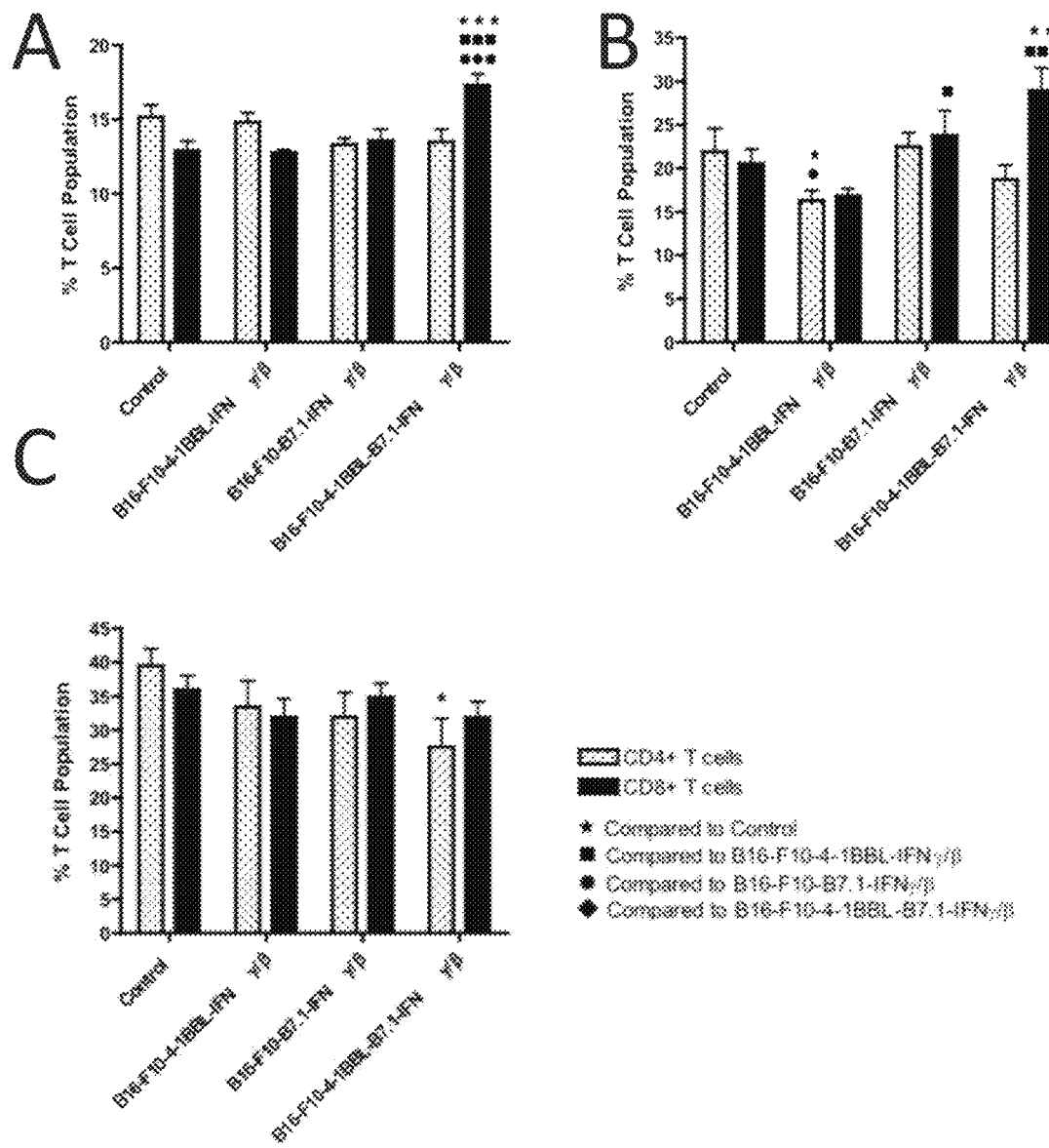
FIG. 5. Increased % $CD8^+$ T cells in spleen and blood but not lymph nodes from mice receiving two doses of the B16-F10/4-1BBL/B7.1/IFNγ/β vaccine. C57BL/6 mice were either used as controls (n=9) or injected as shown using vaccination protocol 1 with either B16-F10/4-1BBL/IFNγ/β (n=6), B16-F10/B7.1/IFNγ/β (n=6) or B16-F10/4-1BBL/B7.1/IFNγ/β (n=7) vaccines. On day 11, the spleens (A), blood (B) and lymph nodes (C) were assessed for differences in $CD4^+$ and $CD8^+$ T cell populations by flow cytometry. This data is representative of two independent experiments and the mean and standard error is shown.
Figure 6:
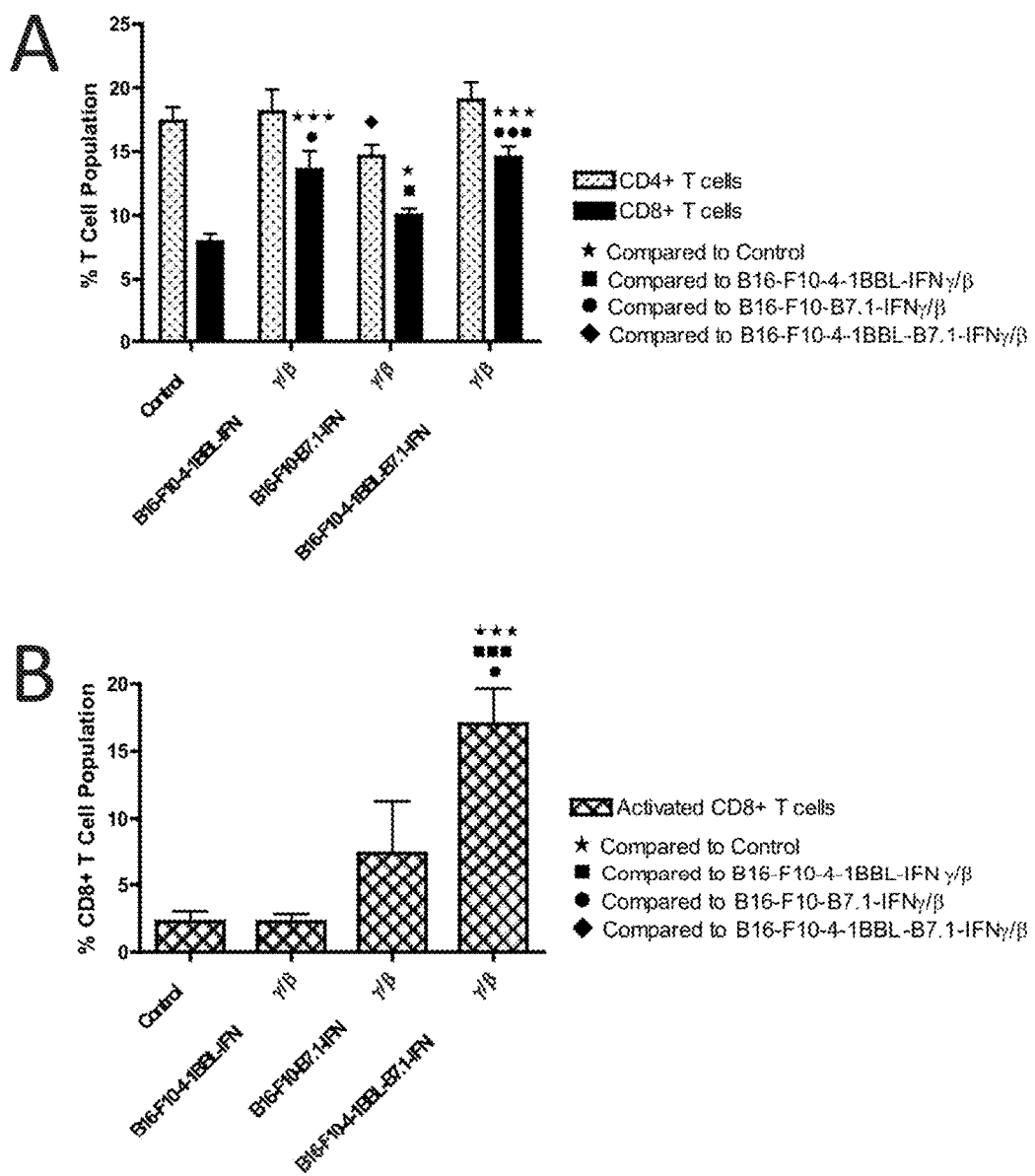
FIG. 6. (A) Increased % $CD8^+$ T cells in the splenic lymphocyte populations of mice given two vaccine doses and expanded in MLC. C57BL/6 mice were either used as controls (n=9) or injected as shown using vaccination protocol 1 with either B16-F10/4-1BBL/IFNγ/β (n=6), B16-F10/B7.1/IFNγ/β (n=6) or B16-F10/4-1BBL/B7.1/IFNγ/β (n=7) vaccines. Spleens from vaccinated and unvaccinated, control mice were harvested and lymphocytes were isolated and expanded in MLCs that contained a monolayer of inactivated IFNγ/β treated B16-F10/B7.1 cells. After three to five days in the MLC, lymphocytes were collected and analysed for changes in the $CD4^+$ and $CD8^+$ T cell populations by flow cytometry. The data shown was collected from four independent experiments. (B) Highly elevated activated $CD8^+$ T cell population from splenic derived lymphocytes expanded in MLC in response to the B16-F10/4-1BBL/B7.1/IFNγ/β vaccine. Lymphocytes from control mice or mice vaccinated with two doses of either B16-F10/4-1BBL/IFNγ/β, B16-F10/B7.1/IFNγ/β or B16-F10/4-1BBL/B7.1/IFNγ/β cells were cultured for 5 days in MLC using the appropriate cancer vaccine cells as antigenic stimulators. Lymphocytes expressing CD8 were selected using flow cytometry and then further analysed for the co-expression of the activation markers CD107a and IFNγ. The mean and SE are displayed.

Significant differences were noted in particular in the CD8+ T cell population expanded in three to five day MLC with cancer cells as stimulators, as shown in FIG. 6 (p<0.0001). Differences in % CD4+ T cells were also observed although these were not as marked as the increase detected in the CD8+ T cell numbers. The enhanced CD8+ T cell populations in MLC were consistent with the previous results (FIG. 5) in which the splenic and PBL populations were directly analysed for their T cell levels. The % CD8+ T cells from MLC of all vaccinated mice were significantly greater than those obtained from the control mice. Specifically, lymphocytes from the B16-F10/4-1BBL/B7.1/IFNγ/β vaccinated mice produced significantly greater % CD8+ T cells than controls or B16-F10/B7.1/IFNγ/β vaccinated mice after culture in MLC (p<0.0001 and 0.001, respectively). These results demonstrate that significant activated effector CD8+ CTLs could be produced in the spleens of mice immunized with suitable cancer vaccines.

Figure 7:
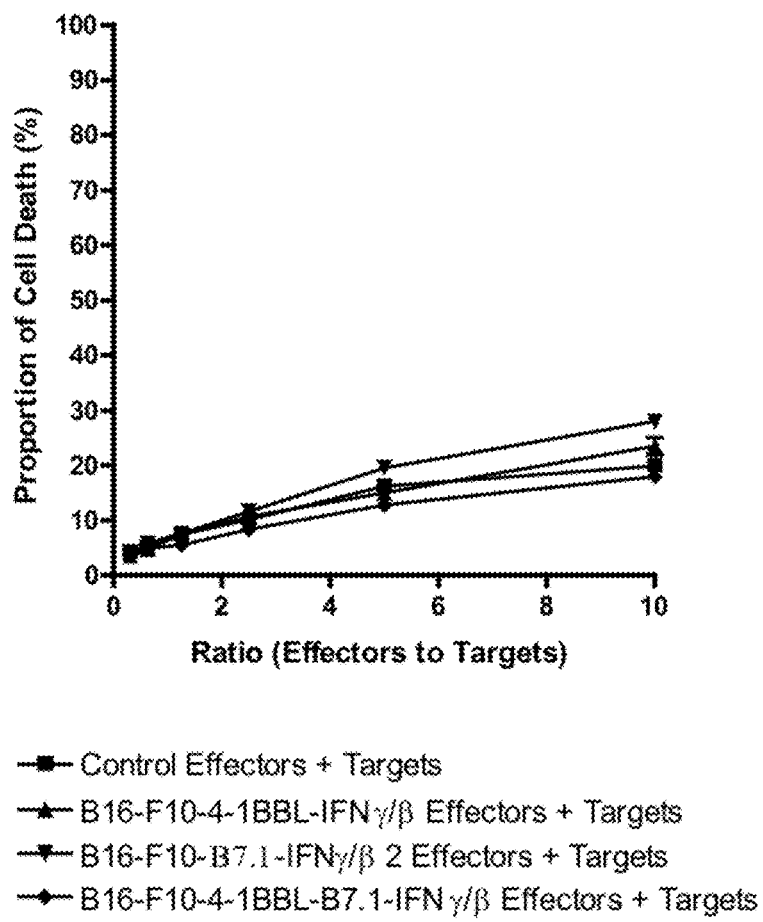
FIG. 7. No significant difference in cytotoxicity of lymph node derived lymphocytes from control or vaccinated mice, as determined in CTL assays. Lymph nodes from control C57BL/6 mice or mice vaccinated with two doses of either B16-F10/4-1BBL/IFNγ/β, B16-F10/B7.1/IFNγ/β or B16-F10/4-1BBL/B7.1/IFNγ/β vaccine cells were removed, the lymphocytes purified and analysed in a cytotoxicity assay using B16-F10/B7.1/IFNγ/β live cells as targets. SYTOX Green uptake was used to determine proportion of cell death as detected using excitation and emission wavelengths of 485 nm and 525 nm on a spectrophotometer. The mean and standard error are shown and the proportion of cell death was displayed as % of total. The differences between the groups were determined using the general linear model (n=4 per group).

Characterization of the Activation Status of the MLC Derived CD8+ T Cells Induced in Response to Anticancer Vaccines Activated, antigen specific CD8+ T cells are known to express IFNγ and CD107a as described by Betts et al. (2003). Therefore, splenic derived lymphocytes grown for five days in MLC were analysed to determine their % activated, CD8+ effector T cells using flow cytometry (FIG. 7). This required further gating the lymphocytes according to the expression of CD8 and then determining the % CD8+ T cells that also expressed the surface marker CD107a and the intracellular cytokine, IFNγ.

The ANOVA comparing the % activated T cells was found to be highly significant (p<0.005). FIG. 6B shows that the lymphocytes from mice vaccinated with the B16-F10/4-1BBL/B7.1/IFNγ/β cells produced significantly higher % activated CD8+ T cells after being grown in MLC for five days when compared to all other groups (p<0.05). Furthermore, B16-F10/4-1BBL/B7.1/IFNγ/β vaccinated mice produced more than seven fold greater % activated CD8+ T cells in the MLC compared to control (p=0.0009) and B16-F10/4-1BBL/IFNγ/β vaccinated mice (p=0.0008) and more than twice the number of activated CD8+ T cells than from the B16-F10/B7.1/IFNγ/β vaccinated mice (p=0.014). Having analysed the T cell populations from the various immune organs from all groups of mice, the next stage was to assess the cytotoxic activity of the lymphocytes.

Low Cytotoxic Activity of Lymphocytes Isolated from Lymph Nodes of Mice Receiving Two Vaccine Doses of Anticancer Vaccine After evaluating the different % T cell populations found within samples taken from control and vaccinated mice, it was important to determine whether differences in the T cell populations between treatment groups would translate into killing of melanoma cells in cytotoxic T cell assays. CTL assays were performed using lymphocytes isolated from lymph nodes on the day of harvest (FIG. 7).

The analysis determined that no significant difference existed in the proportion of cell death produced by lymph node derived lymphocytes from any of the four treatment groups (p=0.488; FIG. 7). This analysis confirmed the results presented in FIG. 5C, which determined that there was no significant difference in the relative % of the CD8+ T cells found within the lymph nodes of control mice compared with any of the vaccinated groups.

Figure 8:
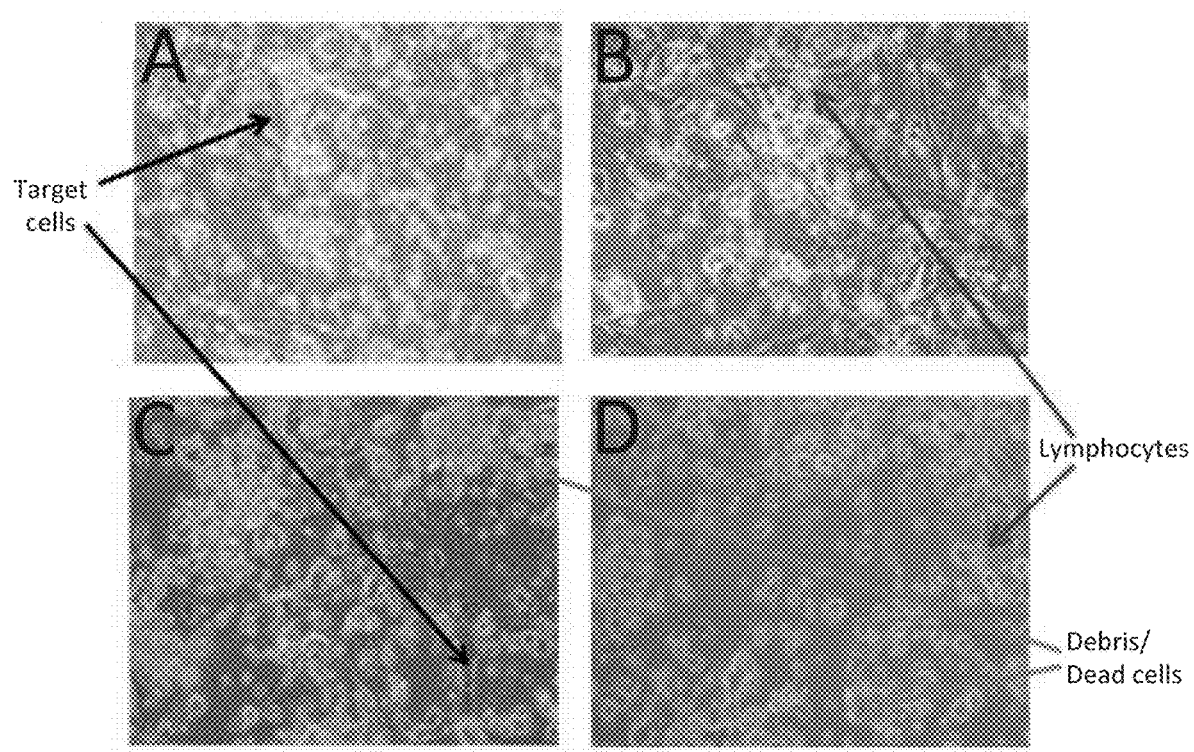
FIG. 8. High levels of cancer cell death observed in MLC wells containing lymphocytes from B16-F10/4-1BBL/B7.1/IFNγ/β vaccinated mice cultured for 5 days. MLC containing monolayers of mitomycin C growth inactivated, IFNγ/β treated B16-F10/B7.1 cells as antigenic stimulators with splenic lymphocytes derived from either: (A) unvaccinated mice or (B) mice vaccinated with B16-F10/4-1BBL-IFNγ/β cells; (C) B16-F10/B7.1/IFNγ/β cells or (D) B16-F10/4-1BBL/B7.1/IFNγ/β cells were visualized under an inverted microscope. The black arrows indicate the target cells, the red arrows show the splenic lymphocytes and the green arrows highlight what is believed to be debris, clumped dying cells and cell death present within the MLC wells after initial visual inspection.

Increased CTL Killing by Splenic Derived Lymphocytes Expanded in MLCs from Mice Receiving Two Doses of B16-F10/4-1BBL/B7.1/IFNγ/β Anticancer Vaccine After assessing the cytotoxic ability of lymphocytes from lymph nodes, next the splenic lymphocyte populations were expanded in MLC for five days and then assessed for their cytotoxic activity (FIG. 8). Given the previous results (FIGS. 5B and 6) showing an increased % CD8+ T cells only in MLC from the vaccinated mice, particularly those given the B16-F10/4-1BBL/B7.1/IFNγ/β vaccine, it was expected greater CTL activity might also have been induced.

Those MLC containing lymphocytes from the control or B16-F10/4-1BBL/IFNγ/β cell vaccinated mice contained media with an orange coloured tint (data not shown), indicating a high level of metabolic activity of the cells thereby reducing the pH of the media (Gerweck 1977, Welshons et al. 1988). By comparison, MLC containing lymphocytes from the B16-F10/B7.1/IFNγ/β or B16-F10/4-1BBL/B7.1/IFNγ/β cell vaccinated mice contained media with a more reddish pigment, indicating higher pH and lower levels of metabolic activity was occurring within the culture (data not shown). These results revealed that colour change could be used as an early indicator of events occurring in the MLC, because upon further investigation by inverted microscopy, it was found that the majority of the antigenic stimulators (melanoma cells) in the MLC containing lymphocytes from the B16-F10/B7.1/IFNγ/β or B16-F10/4-1BBL/B7.1/IFNγ/β vaccinated mice were detached from the plate surface and appeared to have died, as highlighted in FIGS. 8C and D. All 6 well plates contained the B16-F10/B7.1 antigenic stimulator cells (mitomycin C treated to inhibit cell proliferation) in addition to live lymphocytes. Both types of cells metabolise medium even though the tumor cells are not actively growing or dividing. These observations suggest that the tumor cells in the MLC wells were probably the main cell components utilizing the media for their metabolism. This finding indicated that the lymphocytes from B16-F10/B7.1/IFNγ/β and B16-F10/4-1BBL/B7.1/IFNγ/β vaccinated mice were most likely highly active CTLs capable of actively killing the antigenic stimulator cells over the five days in culture, so that the number of live tumor cells in these wells metabolising the culture medium was greatly reduced with less noticeable colour change to the medium in these MLC (data not shown).

Figure 9:
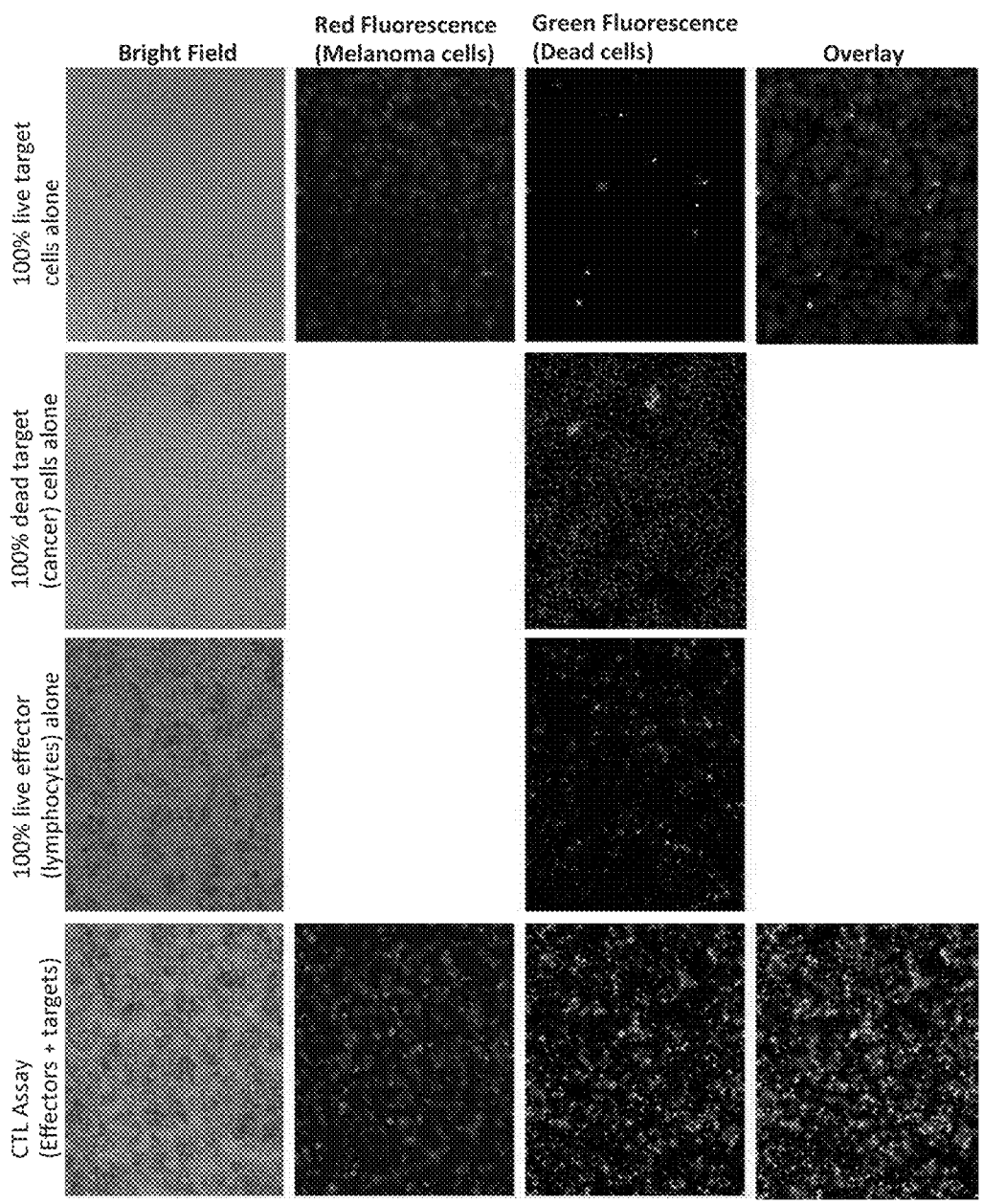
FIG. 9. Representative example of elevated cell death visualized via fluorescence microscopy in CTL assays of lymphocytes from B16-F10/4-1BBL/IFNγ/β vaccinated mice grown in MLC. Splenic lymphocytes from B16-F10/4-1BBL/IFNγ/β vaccinated mice were grown in MLC for 5 days and then used for CTL assays. The target B16-F10/B7.1 melanoma cells were stained with DiI (red) and SYTOX Green was used to stain for % dead cells. Bright field, green and red fluorescence images were recorded for the different wells within the CTL assays, which contained either 100% live target cells alone (IFNγ/β treated B16-F10/B7.1 cells), 100% dead target cells alone (IFNγ/β treated B16-F10/B7.1 cells treated with 0.4% NP9 detergent), 100% live effector cells alone (lymphocytes) or effectors plus targets combined in a 10:1 ratio. Overlaid images are also shown.
Figure 10:
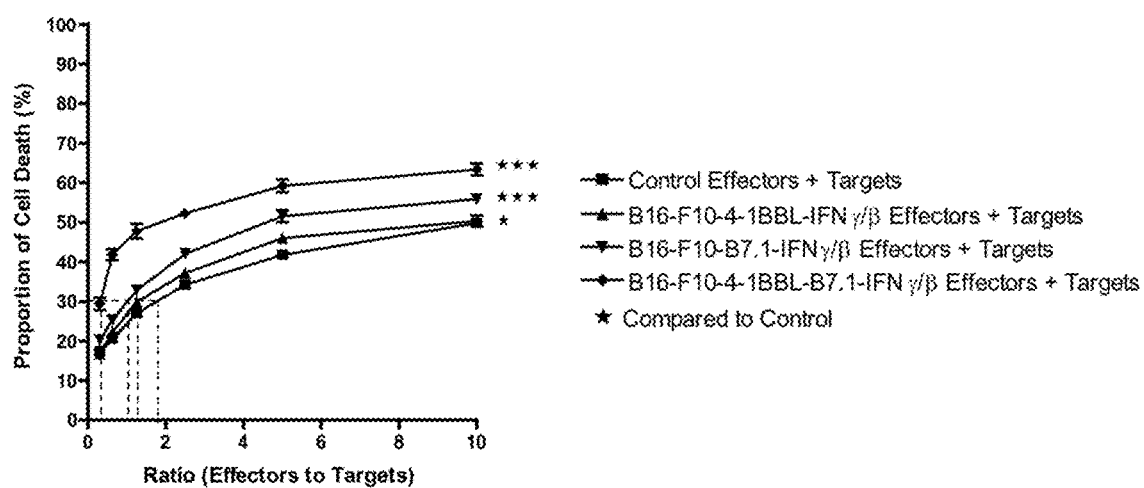
FIG. 10. Increased cell death in CTL assays with splenic derived lymphocytes from B16-F10-4-1BBL-B7.1-IFNγ/β vaccinated mice grown in MLCs. Splenic lymphocytes from naïve, unvaccinated C57BL/6 mice or mice vaccinated with either B16-F10-4-1BBL-IFNγ/β, B16-F10-B7.1-IFNγ/β or B16-F10-4-1BBL-B7.1-IFNγ/β cells according to vaccination protocol 1 were prepared, purified and cultured in MLCs with B16-F10-B7.1-IFNγ/β antigenic stimulators for five days. SYTOX Green nuclear uptake and immunofluorescence was used to detect cell death using a spectrophotometer set on an excitation wavelength of 485 nm and an emission wavelength of 525 nm. The ratios of the effector to live cancer target cells ranged from 0.3:1 up to 10:1 and the mean fluorescence and standard error for each ratio are plotted. The proportion of cell death was calculated and the data analysed using the general linear model.

After noting these initial observations, the lymphocytes were then removed from the MLC and prepared for use in CTL assays and representative green (dead cells) and red (pre-stained melanoma cells) fluorescence images were recorded from the wells in the CTL assay plates (FIGS. 9 and 10).

During the analysis of the CTL assays, bright field, red fluorescence (DiI) and green fluorescence images (SYTOX Green) were taken for specific wells within the CTL assay (FIG. 9). The bright field and red fluorescence images of the 100% live target cells alone stained with DiI from all 4 CTL assays showed that although the target cancer cells established as near confluent monolayers, very few dead cells in this population were detected by the green fluorescence images of SYTOX dye uptake into the nucleus. This result indicates that the target cells alone were mostly healthy live populations and thus, would not contribute significantly to the background signal produced as a result of compromised or dying target cells. However, the target cells were effectively killed by the MLC derived lymphocytes, as shown in the bottom row of the images (labeled "Effectors+Targets in CTL assays", FIG. 9). The control wells for 100% dead target cells (induced by adding 0.4% NP9 detergent) showed the maximum fluorescence possible when the entire population of target cells were killed.

The green fluorescence detected in the "100% live effector cells" alone population was used as the base level of cell death, which was subtracted from the green fluorescence values for the lymphocytes combined with the target cells (labeled "effectors+targets in the CTL assay") when the images were quantitated using a spectrophotometer. The small proportion of cell death detectable in wells containing the 100% live effector lymphocytes alone indicated that they contained predominantly healthy cells and only a small number of lymphocytes were dying during the processing and preparation of the MLC. Moreover, it was highly likely that the cell death observed in wells containing 100% live effector lymphocytes alone was probably the result of antigenic stimulator target cell debris carried over from the MLC, where it was observed that antigenic stimulator target cells were undergoing apoptosis; particularly in MLC containing the more potent vaccines (FIG. 8).

The debris of the dead cell material described above was of similar size to that of the lymphocytes, which made its separation and removal very difficult even when using FICOLL-PAQUE™ PLUS or other separation techniques. Nevertheless, even with this baseline level of dead cells, significantly increased green fluorescence levels were detected in those wells containing the combination of effector and target cells for all four CTL assays. Again, varying levels of cell death were detected in these wells and the control effector and target reactions showed the lowest level of green fluorescence compared to the other test reactions incorporating effectors from the B16-F10/4-1BBL/B7.1/IFNγ/β vaccinated mice (FIG. 9). The photographic results from cell media of the MLCs supported the CTL data quantified by spectrophotometry as shown in FIG. 10.

Analysis of the data shown in FIG. 10 revealed that there was a highly significant effect of vaccination increasing CTL activity (p<0.0001). Post hoc tests were then used to determine the proportion of cell death in the CTL assay and showed that the lymphocytes derived from the B16-F10/4-1BBL/B7.1/IFNγ/β vaccinated mice were significantly more active than those in all other CTL assays (p<0.005). Similarly, the proportion of cell death from the CTL assay using lymphocytes from B16-F10/B7.1/IFNγ/β vaccinated mice were also significantly different to all other CTL assays (p<0.005). The analysis also determined that the highest rate of change in cell death with respect to ratio was found in the CTL assay with lymphocytes derived from B16-F10/4-1BBL/IFNγ/β vaccinated mice followed by those from the B16-F10/B7.1/IFNγ/β, B16-F10/4-1BBL/IFNγ/β vaccinated mice and least active were the lymphocytes derived from control mice. This statistical analysis confirms the results shown in FIG. 10. Furthermore, the relative fold increase in proportion of cell death in the CTL assay using lymphocytes derived from the B16-F10/4-1BBL/B7.1/IFNγ/β vaccinated mice was 5.7 compared to lymphocytes from control, unvaccinated mice as shown in Table 4. In addition, approximately a twofold synergistic increase in the cancer (target) cell killing induced by lymphocytes derived from B16-F10/4-1BBL/B7.1/IFNγ/β vaccinated mice was shown above the combined results using lymphocytes from B16-F10/4-1BBL/IFNγ/β and B16-F10/B7.1/IFNγ/β vaccinated mice (Table 4).

TABLE 4

| Vaccine | Number of effector cells ($\times 10^4$) per lytic unit[1] | Relative fold increase in lytic units per effector cell population[2] |
|---|---|---|
| Control, unvaccinated | 3.4 | 1 |
| B16-F10-4/1BBL/IFNγ/β | 2.5 | 1.4 |
| B16-F10/B7.1/IFNγ/β | 2.0 | 1.7 |
| B16-F10/4-1BBL/B7.1/IFNγ/β | 0.6 | 5.7 |

Figure 4:
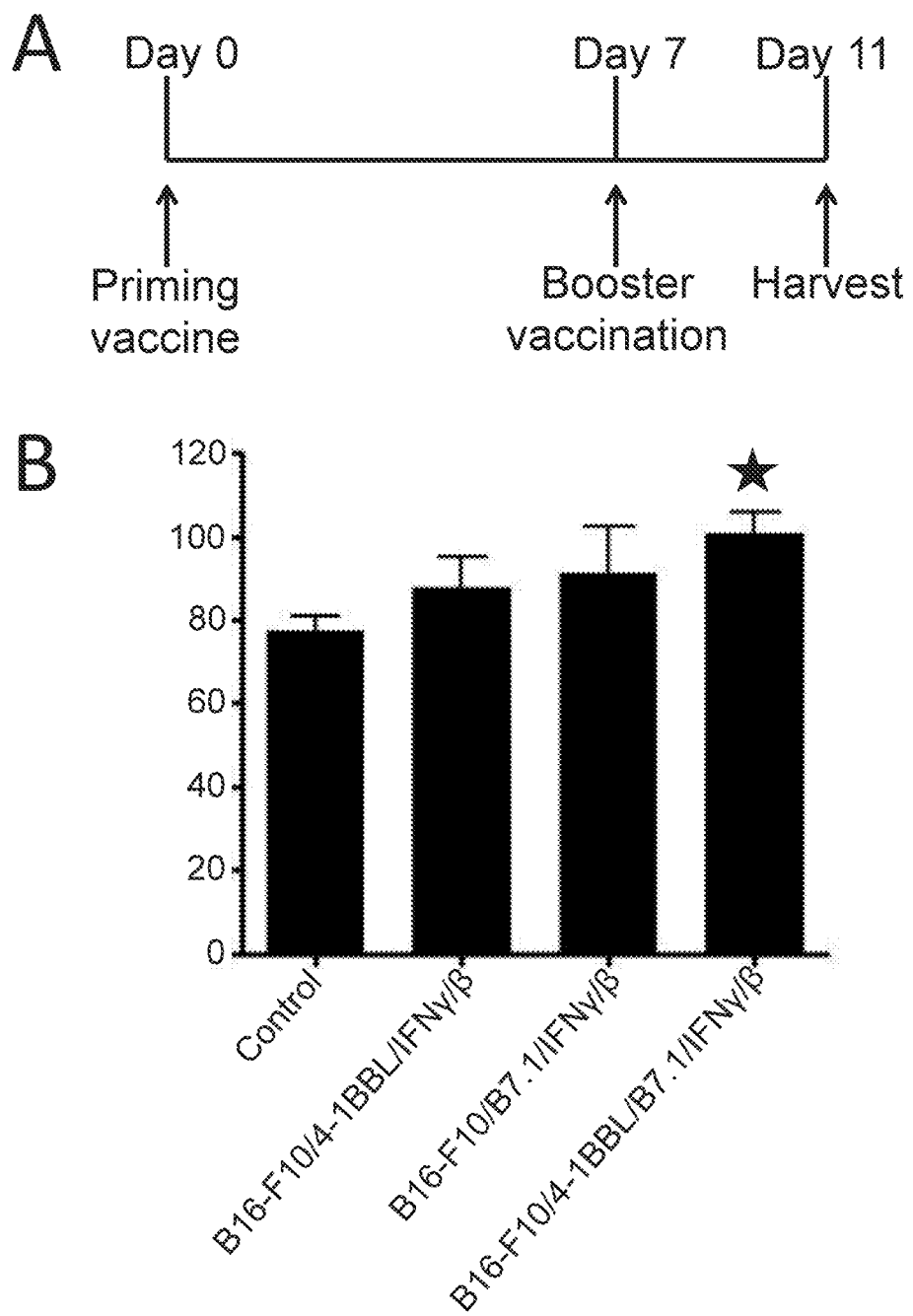
FIG. 4. Timeline of vaccination and harvesting according to "Protocol 1" for the comparison of the splenic weights from control versus mice treated with two doses of vaccine. C57BL/6 controls (n=9) or mice injected intraperitoneally with two doses of vaccine comprising $1\times10^7$ irradiated B16-F10/4-1BBL/IFNγ/β (n=6), B16-F10/B7.1/IFNγ/β (n=6) or B16-F10/4-1BBL/B7.1/IFNγ/β (n=7) cells were vaccinated according to the timeline shown in A). Spleens were removed and weights recorded as the mean±SE and are representative of two independent experiments as shown in B). Significance levels were determined using one-way ANOVA. *p<0.05, p<0.01, *p<0.005 (as in all other figures presented herein, unless stated otherwise).

[1]The values are derived from FIG. 4.9 from the points where the graphs intercept the line for 1 Lytic Unit = Number of Effector cells ($\times 10^4$) producing 30% Target cell lysis.
[2]The results are determined relative to CTL responses of the control, non-vaccinated mice assigned a value of 1.

Figure 11:
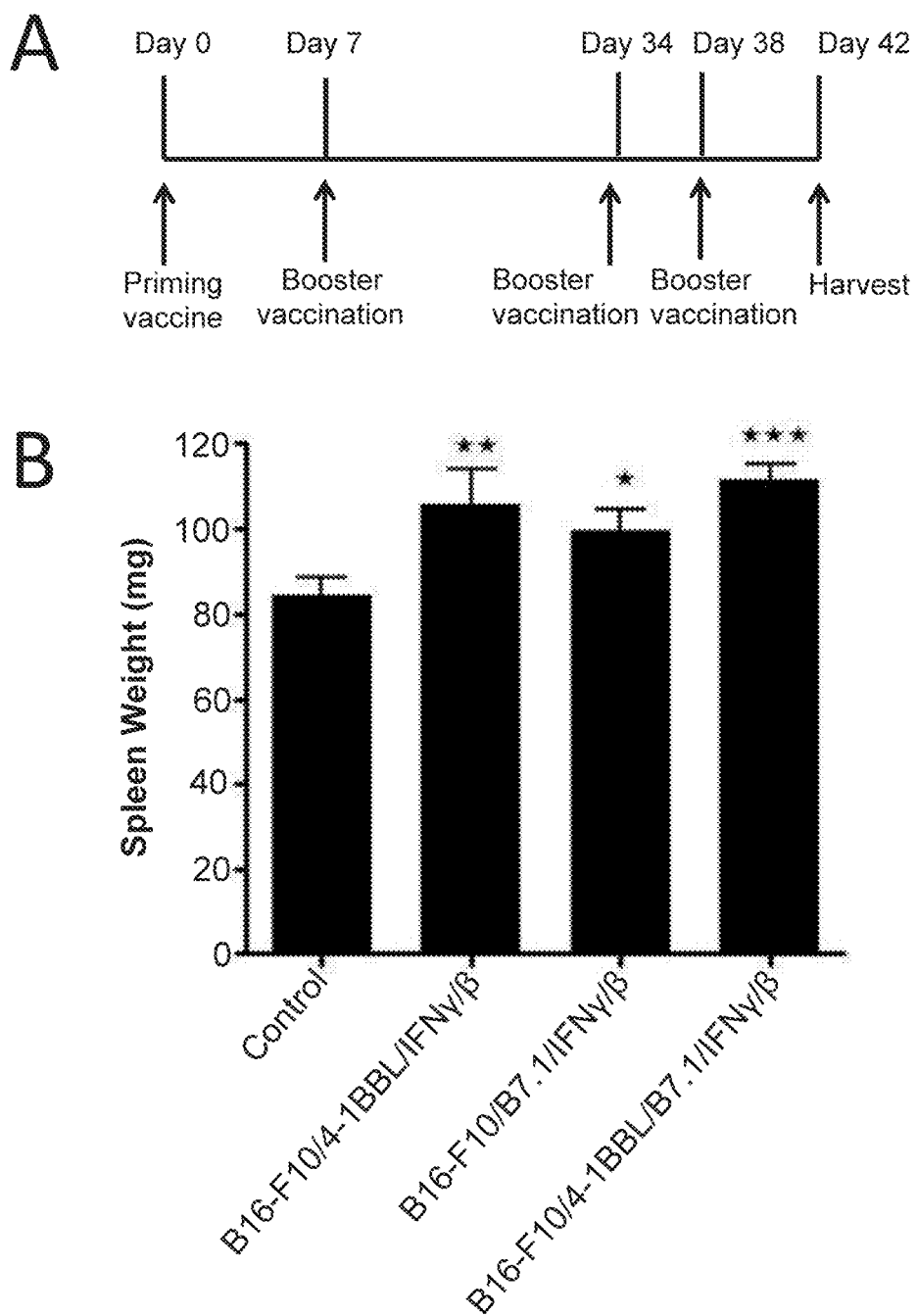
FIG. 11. Timeline of vaccination and harvesting according to "Protocol 2" to compare the splenic weights from control versus mice treated with four vaccine doses. C57BL/6 controls (n=12) or mice injected intraperitoneally with four doses of vaccine comprising $1 \times 10^7$ irradiated B16-F10/4-1BBL/IFNγ/β (n=9), B16-F10/B7.1/IFNγ/β (n=10) or B16-F10/4-1BBL/B7.1/IFNγ/β (n=11) cells were vaccinated according to the timeline shown in (A). Spleens were removed and weights recorded as the mean±SE and are representative of two independent experiments as shown in (B).
Figure 12:
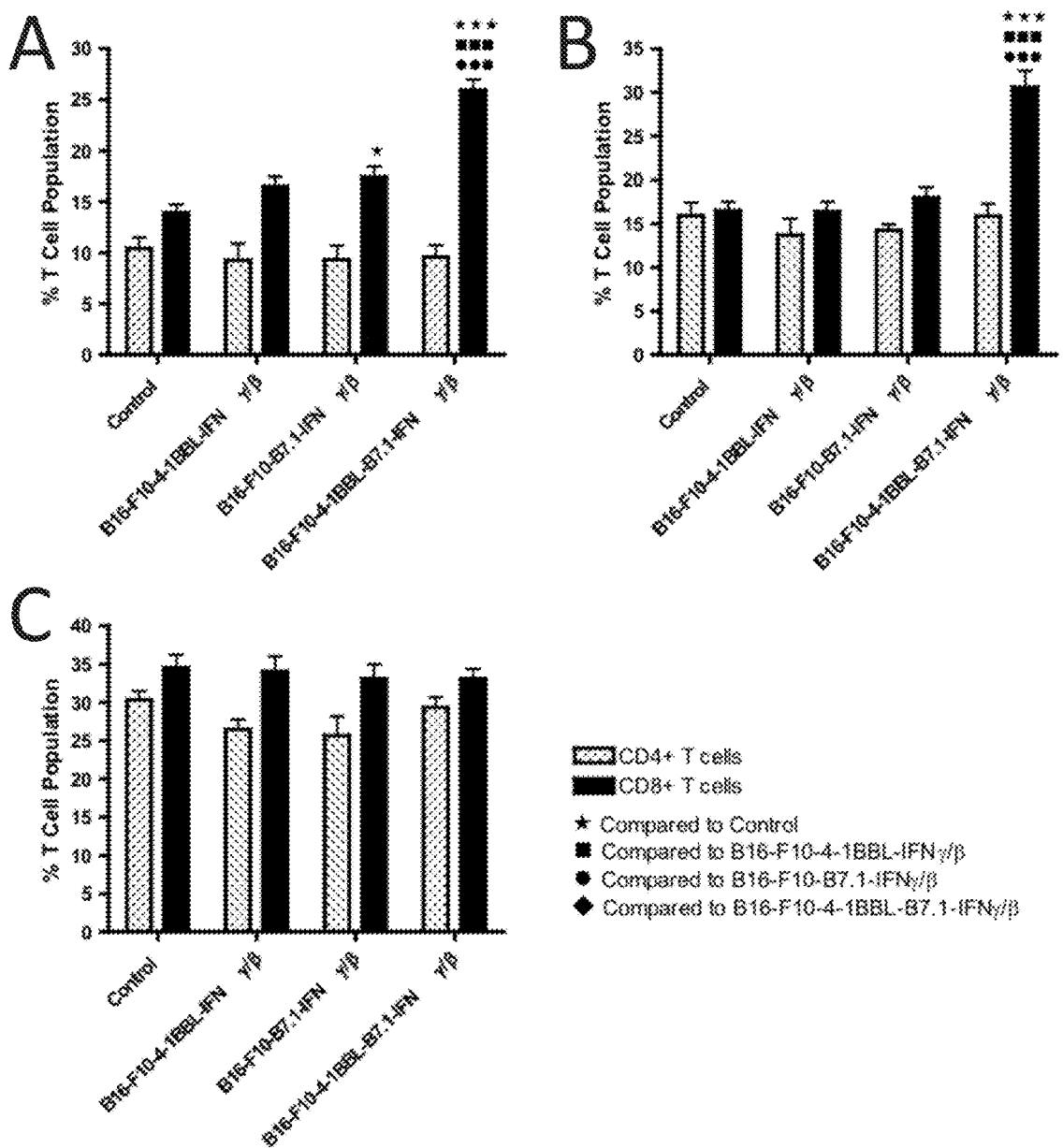
FIG. 12. Highly elevated % CD8$^+$ T cells in the spleen and blood but not in lymph nodes from mice given four doses of the B16-F10/4-1BBL/B7.1/IFNγ/β vaccine. C57BL/6 mice were injected as shown in the timeline of vaccination protocol 2 with either B16-F10/4-1BBL/IFNγ/β (n=9), B16-F10/B7.1/IFNγ/β (n=10) or B16-F10/4-1BBL/IFNγ/β (n=11) vaccine cells or remained untreated as controls (n=12). On Day 42, the spleens (A), blood (B) and lymph nodes (C) were assessed for differences in CD4$^+$ and CD8$^+$ T cell populations by flow cytometry. This data is representative of two independent experiments and the mean and standard error is shown.

Highly Elevated CD8+ T Cell Responses Produced in Mice Receiving 4 Doses of the B16-F10/4-1BBL/B7.1/IFNγ/β Whole Cell Anticancer Vaccine As described above, the initial vaccination protocol utilised in this study involved a prime/boost strategy. A alternative vaccination protocol ("vaccination protocol 2") with the addition of two more booster injections was performed with the aim of further enhancing the anticancer immune response. Thus, for vaccination protocol 2 naïve mice received two doses of vaccine (using the prime/boost strategy) separated by a seven day interval between doses, followed by a twenty-seven day period where the mice were rested prior to administering a further two booster injections separated by an interval of four days. The mice were then sacrificed four days after the final injection. On the day of harvest (day 42), spleen, blood and lymph nodes were collected separately from all the mice and assayed for immune responses. A timeline showing the days that the mice were vaccinated according to protocol 2 is illustrated in FIG. 11A. Spleens were weighed (FIG. 11B) and then cell preparations from spleens, blood and lymph nodes were analysed and T cell numbers determined by flow cytometry (FIG. 12).

A significant difference in spleen weights was observed when comparing the treatment groups (p=0.002). Further analysis via post hoc testing determined that the mean weights of spleens from all three groups of vaccinated mice were significantly heavier compared to control mice as shown in FIG. 11B. A highly significant difference in spleen weight between B16-F10/4-1BBL/B7.1/IFNγ/β vaccinated mice (mean=111.8 mg) and control mice (mean=84.3 mg) was determined (p<0.005). Furthermore, no differences were seen when comparing the spleen weights from among any of the vaccinated groups of mice.

It is evident from FIGS. 12A and B that significantly higher % CD8+ T cells were produced in the spleens and blood of the B16-F10/4-1BBL/B7.1/IFNγ/β vaccinated mice compared to all other treatment groups (p<0.005 for both). Furthermore, post hoc testing determined that spleens of B16-F10/4-1BBL/B7.1/IFNγ/β vaccinated mice had significantly higher % CD8⁺ T cells compared to controls (p<0.0001), compared to B16-F10/4-1BBL/IFNγ/β vaccinated mice (p<0.0001) and compared to B16-F10/B7.1/IFNγ/β vaccinated mice (p<0.0001). These results from analysing the spleens were very similar to the changes in % CD8⁺ T cells detected within the blood. Thus, the B16-F10/4-1BBL/B7.1/IFNγ/β vaccinated mice had significantly higher % CD8⁺ T cells in the PBL samples than all other groups (p<0.0001). No differences in % CD4⁺ T cells within the spleen, blood or lymph node samples between the treatment groups were detected. Furthermore, there were no differences in the CD8⁺ T cells produced within the lymph nodes between any of the groups tested.

Figure 13:
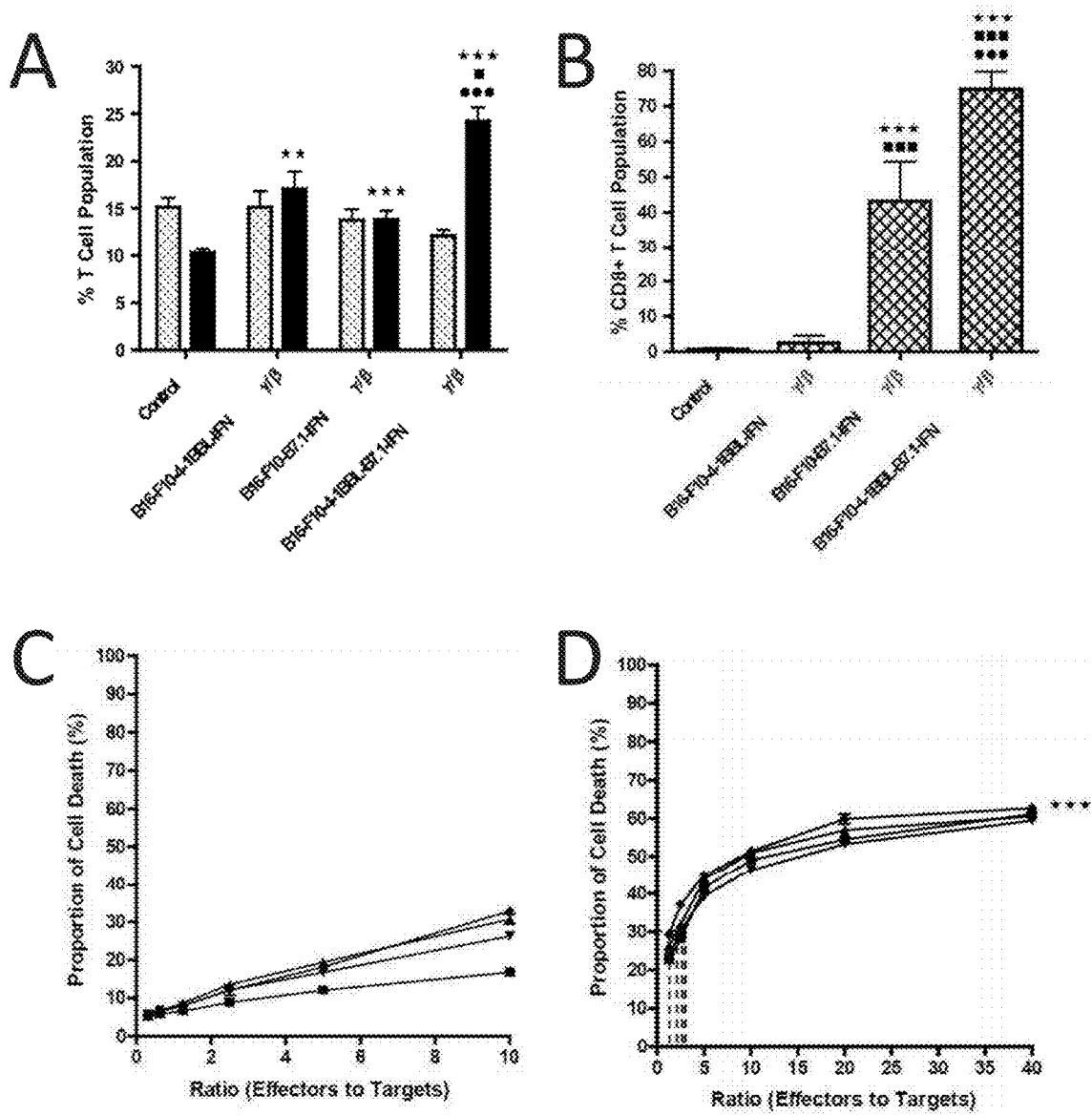
FIG. 13. CD4$^+$ and CD8$^+$ T cell responses from lymphocytes derived from the spleen and lymph nodes of mice exposed to 4 vaccine doses. (A) C57BL/6 mice were either used as controls (n=12) or vaccinated according to vaccination "protocol 2" with either B16-F10/4-1BBL/IFNγ/β (n=9), B16-F10/B7.1-IFNγ/β (n=10), or B16-F10/4-1BBL/B7.1/IFNγ/β (n=11) vaccines. Spleens were harvested and lymphocytes were grown in MLC that contained a monolayer of inactivated IFNγ/β treated B16-F10/B7.1 cells. After 3 to 5 days in the MLC, lymphocytes were collected and analysed for changes in CD4$^+$ and CD8$^+$ T cell populations by flow cytometry. This data was collected from four independent experiments. Black bars: CD8$^+$ T cells; gray bars: CD4$^+$ T cells. (B) Lymphocytes from control mice or mice administered with 4 vaccine doses of either B16-F10/4-1BBL/IFNγ/β, B16-F10/B7.1/IFNγ/β or B16-F10/4-1BBL/B7.1/IFNγ/β cells were cultured for five days in MLC using cancer vaccine cells as antigenic stimulators. Flow cytometric analysis of the lymphocytes was performed, selecting those expressing CD8 and then further assessed for the presence of the activation markers CD107a and IFNγ. Significance indicators of (A) and (B) represent: ■ Compared to control; ▲ Compared to B16-F10/4-1BBL/IFNγ/β; ▼ Compared to B16-F10/B7.1/IFNγ/β; and ◆ Compared to B16-F10/4-1BBL/B7.1/IFNγ/β. (C) Lymph nodes from control C57BL/6 mice or mice vaccinated with four doses of either B16-F10/4-1BBL/IFNγ/β, B16-F10/B7.1/IFNγ/β or B16-F10/4-1BBL/B7.1/IFNγ/β vaccine cells were removed and these lymphocytes were purified and analysed in CTL assays using B16-F10/B7.1/IFNγ/β live cells as targets. SYTOX Green uptake was used to determine proportion of cell death as detected using excitation and emission wavelengths of 485 nm and 525 nm on a spectrophotometer. Differences in proportion of cell death was determined using the general linear model (n=4 per group). (D) Splenic lymphocytes from control mice and mice vaccinated with either B16-F10/4-1BBL/IFNγ/β, B16-F10/B7.1/IFNγ/β or B16-F10/4-1BBL/B7.1/IFNγ/β cells according to "protocol 2" were purified four days following final vaccination. SYTOX Green uptake was used to determine the proportion of cell death as detected using excitation and emission wavelengths of 485 nm and 525 nm on a spectrophotometer. The proportion of cell death was calculated and the differences between the groups were determined using the general linear model (n=2 per group), and statistical significance is shown compared to the control sample. Graph traces for (C) and (D): ■Control Effectors+Targets; B16-F10/4-1BBL/IFNγ/β Effectors+Targets; ▼B16-F10/B7.1/IFNγ/β Effectors+Targets; and ◆B16-F10/4-1BBL/B7.1/IFNγ/β Effectors+Targets.

Increased CD8⁺ T Cell Populations in Splenic MLC Antigenically Stimulated with Cancer Vaccine Cells In light of these results, the next stage was to analyse the changes in the splenic derived CD4⁺ and CD8⁺ T cell populations by flow cytometry after being antigenically stimulated in MLC for 3 to 5 days as shown in FIG. 13A.

Significant differences in the splenic derived T cell populations expanded in MLC were noted, particularly in the CD8⁺ T cell population expanded in the three to five day MLC where the cancer cells were used as antigenic stimulators (p<0.0001). By comparison, no differences in % CD4⁺ T cells were recorded. The enhanced CD8⁺ T cell population in splenic derived MLC was consistent with the previous result (FIG. 12) analysing both splenic and PBL levels directly harvested from the vaccinated mice. The % CD8⁺ T cells from MLC of all vaccinated mice were significantly greater than those isolated from the control mice. Specifically, lymphocytes from B16-F10/4-1BBL/B7.1/IFNγ/β vaccinated mice produced significantly greater % CD8⁺ T cells than controls (p<0.0001), B16-F10/4-1BBL/IFNγ/β vaccinated mice (p=0.034) and B16-F10/B7.1/IFNγ/β vaccinated mice (p<0.0001). These results further support the finding in section described above that significant effector CD8⁺ CTLs were being produced and expanded in the spleens of mice immunized with the cancer vaccines.

Characterization of the Activation Status of the MLC Derived CD8⁺ T Cells Induced in Response to Cancer Vaccines Following the CD4⁺ and CD8⁺ analysis of MLC splenic derived lymphocytes after five days in culture as described in the study above, the next stage was to assess the activation status of the CD8⁺ T cells by detecting the presence of CD107a and intracellular levels of IFNγ via flow cytometry (FIG. 13B).

The intergroup analysis comparing the % activated CD8⁺ T cells was found to be highly significant (p<0.005). FIG. 13B indicates that there was no difference in % activated CD8⁺ T cells between MLC derived lymphocytes from control and B16-F10/4-1BBL/IFNγ/β vaccinated mice. By comparison, the lymphocytes from mice vaccinated with B16-F10/4-1BBL/B7.1/IFNγ/β cells produced significantly higher activated CD8⁺ T cells after growth in MLC for five days compared to control (p<0.0001), B16-F10/4-1BB/IFNγ/β vaccinated mice (p<0.0001) and from the B16-F10/B7.1/IFNγ/β vaccinated mice (p=0.004). Furthermore, approximately 75% of CD8⁺ T cells generated from MLC of B16-F10/4-1BBL/B7.1/IFNγ/β vaccinated mice were activated, which was 107-fold greater than the number obtained from control mice and 1.7-fold greater than the number of activated CD8⁺ T cells from the B16-F10/B7.1/IFNγ/β vaccinated mice.

No Difference in Cytotoxic Potential of Lymph Node Derived Lymphocytes from Mice Given Four Vaccine Doses Compared to Control Mice After analysing the T cell populations from various samples from control and vaccinated mice, the lymph node derived lymphocytes collected on the day of harvest were assayed for their cytotoxic capacity to kill melanoma cells in CTL assays, as described previously.

The general linear model analysis of the data shown in FIG. 13C indicates that there is no significant difference in the proportion of cell death produced by lymph node derived lymphocytes between any of the four groups (p=0.145). This analysis supports the results presented in FIG. 12C, which concluded that no significant differences in the relative percentages of CD8⁺ T cell populations were detected within the lymph nodes from any of the four treatment groups (FIG. 13C).

Low Levels of Cytotoxicity Detected in Splenic Derived Lymphocytes from B16-F10/4-1BBL/B7.1/IFNγ/β Vaccinated Mice Compared to Control Mice The cytotoxic activity of the splenic lymphocytes assayed on the day of harvest from the naïve control mice and mice receiving the four doses of vaccine were analysed for their ability to kill the melanoma cells as targets in CTL assays (FIG. 13D). The purpose of this experiment was to determine whether the splenic derived lymphocytes analysed directly on the day of harvest would generate stronger CTL killing than the lymph node derived lymphocytes. It was expected that the splenic derived lymphocytes, especially from B16-F10/4-1BBL/B7.1/IFNγ/β vaccinated mice, would exhibit greater CTL activity than lymph node derived lymphocytes due to the significantly higher % CD8⁺ T cells detected in the spleens of these mice on the day of harvest as shown in FIG. 12.

The global F-test analysis determined that there was a significant difference in the proportion of cell death between the treatment groups produced by splenic derived lymphocytes on the day of harvest (p<0.0001). Post hoc testing then showed that the lymphocytes derived from the B16-F10/4-1BBL/B7.1/IFNγ/β vaccinated mice were significantly more active than those in the other CTL assays (p<0.005). Furthermore, a twofold relative increase in tumor (target) cell killing was observed using lymphocytes from B16-F10/4-1BBL/B7.1/IFNγ/β vaccinated mice compared to lymphocytes from control, unvaccinated mice as shown in Table 5. The analysis also determined that the greatest increase in CTL activity based on the ratios calculated in Table 5 resulted with lymphocytes derived from the B16-F10/4-1BBL/B7.1/IFNγ/β vaccinated mice followed by those from the B16-F10/4-1BBL/IFNγ/β vaccinated mice, control mice and the least active were those from the B16-F10/B7.1/IFNγ/β vaccinated mice. These results are supported by the data present in FIG. 12A where splenic derived lymphocytes from the B16-F10/4-1BBL/B7.1/IFNγ/β vaccinated mice showed the greatest % CD8⁺ T cells. These findings indicate that a portion of these CD8⁺ T cells were already antigenically stimulated, allowing for potent and direct cancer cell killing to be detected within the CTL assays, without the need for expansion in MLC before being assayed.

TABLE 5

| Vaccine | Number of effector cells (×10⁴) per lytic unit[1] | Relative fold increase in lytic units per effector cell population[2] |
|---|---|---|
| Control, unvaccinated | 5.6 | 1 |
| B16-F10/4-1BBL/IFNγ/β | 4.1 | 1.4 |
| B16-F10/B7.1/IFNγ/β | 4.8 | 1.2 |
| B16-F10/4-1BBL/B7.1/IFNγ/β | 2.5 | 2.2 |

[1]The values are derived from FIG. 13D from the points where the graphs intercept the line for 1 Lytic Unit = Number of Effector cells (×10⁴) producing 30% Target cell lysis.
[2]The results are determined relative to CTL responses of the control, non-vaccinated mice, assigned a value of 1.

Thus, as splenic-derived lymphocytes display the greatest CTL activity on the day of harvest from B16-F10/4-1BBL/B7.1/IFNγ/β over lymphocytes from all the other groups tested (FIG. 13D). The next stage was to determine whether the cytotoxic activity of the splenic derived lymphocytes could be enhanced by antigenic stimulation on live cancer cells by expanding them for 5 days in MLC. It was expected that the MLC derived splenic lymphocytes, especially from the B16-F10/4-1BBL/B7.1/IFNγ/β vaccinated mice, might show elevated CTL activity based on the levels of detection of highly elevated and activated CD8⁺ T cell populations in the previous experiments (FIGS. 13A-B). Representative analysis of the MLC plates (data not shown) as well as the mixed cell populations were recorded before the lymphocytes were analysed in CTL assays.

Figure 14:
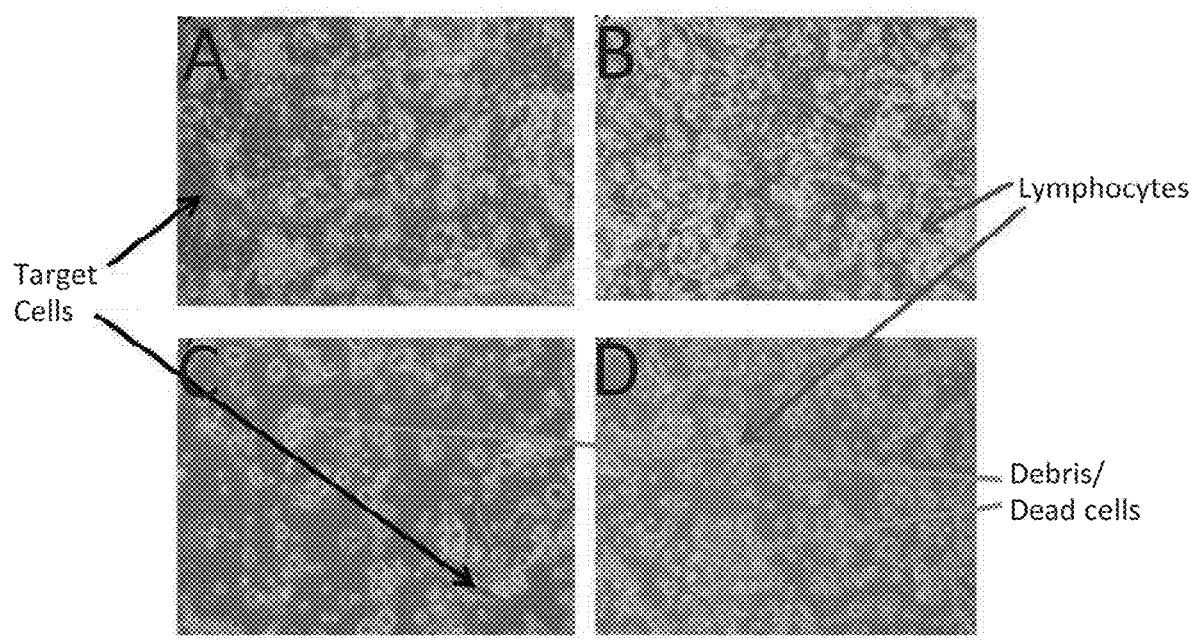
FIG. 14. High levels of cancer cell death observed in MLC wells containing lymphocytes from B16-F10/4-1BBL/B7.1/IFNγ/β vaccinated mice cultured for five days. MLC containing monolayers of mitomycin C growth inhibited, IFNγ/β treated B16-F10/B7.1 cells as antigenic stimulators with splenic derived lymphocytes from either (A) unvaccinated mice; or mice vaccinated with (B) B16-F10/4-1BBL/IFNγ/β cells, (C) B16-F10/B7.1/IFNγ/β cells, or (D) B16-F10/4-1BBL/B7.1/IFNγ/β cells were visualized under an inverted microscope.

The change in colour observed in the tissue culture medium was very similar to that described above. The media in the MLC wells containing splenic-derived lymphocytes from control or B16-F10/4-1BBL/IFNγ/β cell vaccinated mice were shown to contain media with a yellow or orange pigment, respectively. As explained previously, this colour indicates a lower pH and higher metabolic activity of the cells. By contrast, the MLC wells containing lymphocytes derived from B16-F10/4-1BBL/B7.1/IFNγ/β cell vaccinated mice were observed to contain media with a more reddish pigment, indicating higher pH and lower metabolic activity of the cells on the levels of detection of highly elevated and activated CD8⁺ T cell populations in the previous experiments. The number of living, metabolising cells present in the MLC wells shown in FIG. 14 directly corresponds to the colour of the tissue culture medium in the wells. All wells were seeded with the same number of tumor feeder cells and lymphocytes. However, it was apparent from visual inspection that lymphocytes derived from the B16-F10/B7.1/IFNα/β and B16-F10/4-1BBL/B7.1/IFNα/β vaccinated mice had killed a high percentage of the tumor antigenic stimulator cells (FIGS. 14C and D). As a result, there were less live cells present in these wells to metabolise the tissue culture medium and the medium retained a red pigment as described previously. The next stage was to quantify the cytotoxic activity of the lymphocytes from these MLC in CTL assays.

Figure 15:
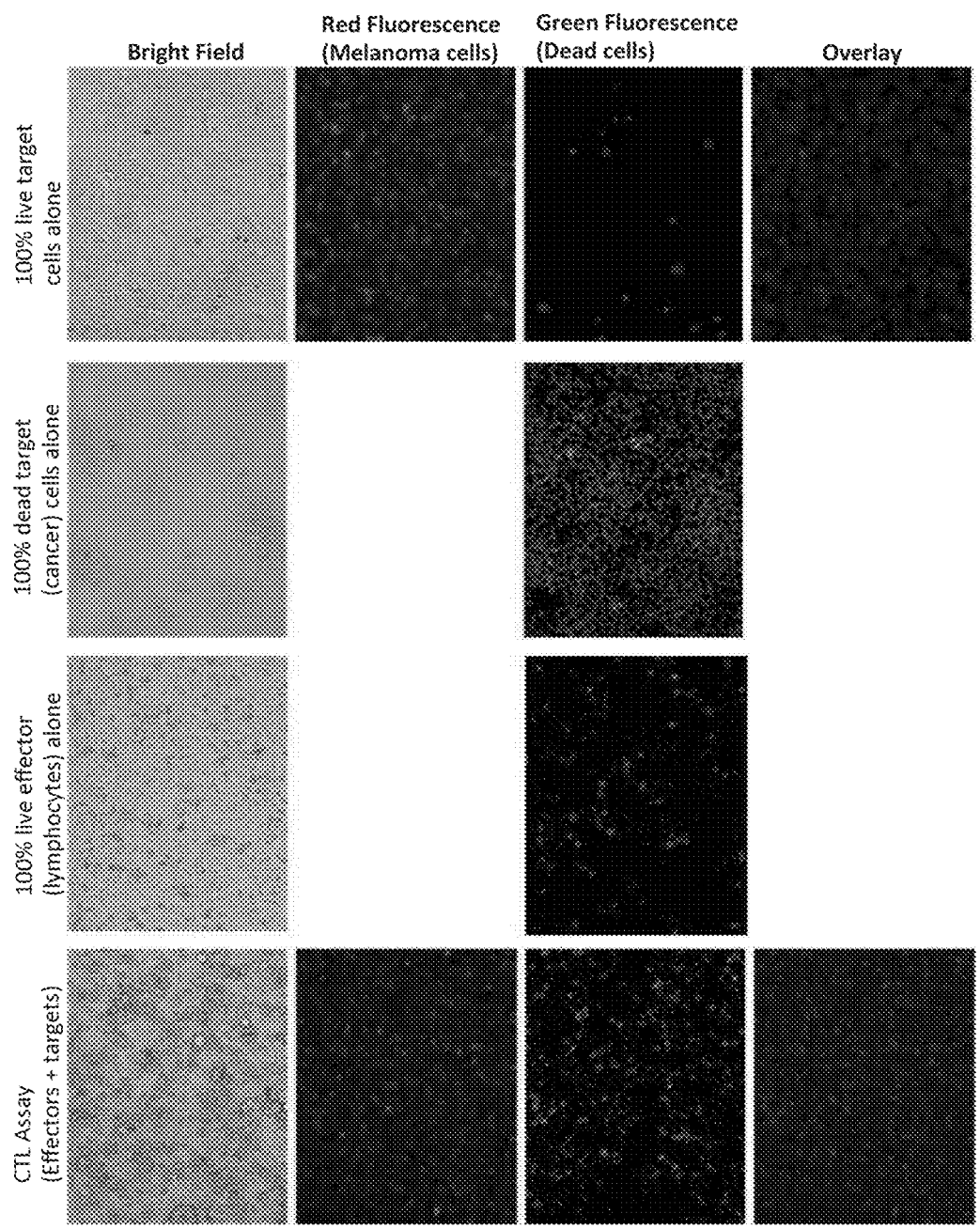
FIG. 15. Representative example of elevated cell death visualized via fluorescence microscopy in CTL assays of MLC derived lymphocytes from B16-F10/4-1BBL/IFNγ/β vaccinated mice. Splenic lymphocytes from B16-F10/4-

FIG. 15 highlights similar observations to what was recorded in FIG. 9. The bright field and red fluorescence (DiI stained) image of the 100% live target melanoma cells alone showed that the cancer cells established as a near confluent monolayer, whereas the green fluorescence (SYTOX Green stained) image indicated a low level of death within the same population. The wells containing the SYTOX Green stained effector plus target cells were shown to contain a higher number of cells that had taken up the green nuclear staining dye compared with wells containing live effector cells alone. This observation indicated that a proportion of the target cancer cells in the effector plus target wells were being directly killed by the lymphocytes during the course of the four hour CTL assay.

The general linear model analysis determined that a highly significant difference existed between all of the groups shown in FIG. 16A (p<0.0001). Post hoc testing revealed that the proportion of cell death from the CTL assay using lymphocytes derived from the B16-F10/4-1BBL/B7.1/IFNγ/β vaccinated mice was significantly increased compared to all other CTL assays tested (p<0.0001). The rank order of the rate of change in cell death with respect to ratio showed that the CTL assay with lymphocytes derived from the B16-F10/4-1BBL/B7.1/IFNγ/β vaccinated mice provided the greatest increase in cell death per unit increase in ratio. The next highest rates of change with respect to increasing ratio was displayed by B16-F10/B7.1/IFNγ/β and B16-F10/4-1BBL/IFNγ/β vaccinated mice and the control mice showed the lowest levels of cell death. Table 6 displays the relative fold increase in the proportion of cell death observed in the CTL assays using lymphocytes derived from the various vaccinated mice. Mice injected with B16-F10/4-1BBL/B7.1/IFNγ/β vaccine displayed an 11.1-fold increase in lytic units per effector cell population compared to lymphocytes from control mice. Lymphocytes derived from B16-F10/B7.1/IFNγ/β and B16-F10/4-1BBL/IFNγ/β vaccinated mice each showed approximately 4-fold increases in cytotoxic activity relative to control. Importantly, it can be concluded from these results that co-expressing 4-1BBL and B7.1 molecules on IFNγ/β treated B16-F10/4-1BBL/B7.1 cells produced a synergistic effect on cytotoxic activity with the observed 11.1-fold increase in lytic units per effector cell population relative to control being larger than the sum of the fold increases in cytotoxic potential elicited from lymphocytes derived from adding together the values of B16-F10/B7.1/IFNγ/β and B16-F10/4-1BBL/IFNγ/β vaccinated mice alone. Therefore, the most active lymphocytes were found to be the ones derived from B16-F10/4-1BBL/B7.1/IFNγ/β vaccinated mice, which confirms and supports the results shown in FIGS. 13A and B.

TABLE 6

| Vaccine | Number of effector cells (×10⁴) per lytic unit[1] | Relative fold increase in lytic units per effector cell population[2] |
|---|---|---|
| Control, unvaccinated | 16.5 | 1 |
| B16-F10/4-1BBL/IFNγ/β | 4.5 | 3.7 |
| B16-F10/B7.1/IFNγ/β | 4.0 | 4.1 |
| B16-F10/4-1BBL/B7.1/IFNγ/β | 1.5 | 11.1 |

[1]The values are derived from FIG. 16 from the points where the graphs intercept the line for 1 Lytic Unit = Number of Effector cells (×10⁴) producing 30% Target cell lysis.
[2]The results are determined relative to CTL responses of the control, non-vaccinated mice, assigned a value of 1.

Example 3

Comparison of Vaccination Regimen on CD8⁺ T Cell Response in Mice

In the previous Examples the % CD4⁺ and CD8⁺ T cell populations in naïve or anticancer vaccinated mice were compared when the mice were injected according to either vaccination Protocol 1 or 2 (described in Example 2). This Example focuses on comparing the T cell responses produced in mice injected with two (i.e., Protocol 1) or four doses (i.e., Protocol 2) of the same vaccine cells after being expanded in MLC for five days.

Significant differences were recorded in the % CD4+ T cell populations expanded in MLC comparing between vaccination Protocol 1 and Protocol 2 in mice receiving the B16-F10/4-1BBL/IFNγ/β and B16-F10/4-1BBL/B7.1/IFNγ/β anticancer vaccines (FIG. 16B). In both groups of treated mice it was observed that those vaccinated according to Protocol 2 had significantly lower % CD4+ T cells than the mice receiving the same vaccine using Protocol 1. The greatest difference was detected in the MLC lymphocytes derived from the B16-F10/4-1BBL/B7.1/IFNγ/β vaccinated mice, in that the mice injected according to Protocol 2 produced significantly lower % CD4+ T cells compared to mice injected with Protocol 1 (p<0.0001). By contrast, the MLC derived lymphocytes from mice treated with the B16-F10/4-1BBL/B7.1/IFNγ/β vaccine according to Protocol 2 produced a significantly elevated % CD8+ T cell population compared to those mice given the same vaccine following protocol 1 (p=0.001; FIG. 16C). The results also showed that the mean % CD8+ T cell populations from all of the groups of vaccinated mice treated according to Protocol 2 were higher than those from mice treated using Protocol 1. The slight increase in CD8+ CTLs observed with the B16-F10/4-1BBL/IFNγ/β vaccine using Protocol 2 was not statistically significant from that of Protocol 1 in these studies.

Increased Proportion Activated CD8+ T Cells Produced Using Protocol 2

The next aim was to compare the % activated CD8+ T cells produced from MLC derived lymphocytes expanded for five days from vaccinated mice treated with either Protocol 1 or Protocol 2.

The independent-sample T test comparing the % activated CD8+ T cells produced in MLC using splenic derived lymphocytes from the B16-F10/B7.1/IFNγ/β and B16-F10/4-1BBL/B7.1/IFNγ/β vaccinated mice were determined to be significantly different (FIG. 17). Mice vaccinated with B16-F10/B7.1-IFNγ/β cells following Protocol 2 produced more than five-fold greater % activated CD8+ T cells in the MLC compared to mice treated with the same vaccine following Protocol 1 (p=0.023). Furthermore, MLC from mice vaccinated with B16-F10/4-1BBL/B7.1/IFNγ/β cells following Protocol 2 produced an average of 74% activated CD8+ T cells compared to 17% generated in MLC from similarly vaccinated mice treated according to Protocol 1 (p<0.0001). These data clearly shows that treating mice with vaccination Protocol 2 considerably enhanced the proportion of activated CD8+ T cell populations produced in MLC compared to the Protocol 1 vaccinated mice.

Example 4

Enhanced Survival of Mice Receiving Whole Cell Vaccine Before Challenge with Live Tumor Cells The next aim of the study was to assess the ability of each of the vaccines to elicit an immune response when the vaccinated mice were subsequently challenged with live melanoma cells. The prophylactic form of treatment was tested to determine whether the elevated and activated CD8+ T cell populations, especially whether those from the B16-F10/4-1BBL/B7.1/IFNγ/β vaccinated mice (as determined in the previous Examples), were able to promote survival when the vaccinated mice were challenged with live cancer cells and whether vaccination could protect the mice from developing tumors.

Protective Immune Responses Elicited after Challenge with Live Cancer Cells

Mice were exposed to 4 vaccine doses according to Protocol 2 (described above) before assessing the immune response in terms of survival after challenge with $5 \times 10^5$ live B16-F10/B7.1 melanoma cells. From the results shown in FIG. 12, it was expected that the length of survival of mice vaccinated according to Protocol 2 before challenge with live cancer cells might be similar, if not greater than that of mice treated with vaccination Protocol 1 (FIG. 18A). This experiment was performed in duplicate to validate the results. The survival of mice in these two experiments were monitored for a period of 102 days and 98 days respectively, and the results of both experiments were combined to provide and overall percentage survival of the mice as shown in FIGS. 18B and C.

The control, unvaccinated mice had a median survival of 25 days. However, all control mice needed to be euthanized by day 31 due to the size of their tumors. 60% of mice treated with the B16-F10/4-1BBL/IFNγ/β cell vaccine succumbed to their tumor burden by day 35, with 40% remaining tumor-free. Nevertheless, this cohort lived for a significantly shorter length of time compared to the others treated with either the B16-F10/B7.1/IFNγ/β or B16-F10/4-1BBL/B7.1/IFNγ/β cell vaccines (p=0.014). Furthermore, a highly significant difference in survival was recorded when comparing control mice to those treated with either the B16-F10/B7.1/IFNγ/β or B16-F10/4-1BBL/B7.1/IFNγ/β cell vaccines (p=0.0003) with all of the latter vaccinated mice being fully protected against challenge with live tumor cells.

To further test the anti-tumor immune responses of the surviving vaccinated mice, they were boosted on days 94 and 98 following the initial tumor challenge, with an additional two doses of vaccine before being re-challenged with $5 \times 10^5$ live B16-F10/B7.1 cells on day 102. Tumor growth and survival was determined as shown in FIG. 18C. The median survival of unvaccinated, control mice was again determined to be 19 days, which was similar to the median survival of the previous cohort of unvaccinated, control mice (25 days, FIG. 18B). By comparison, all of the vaccinated and re-challenged mice remained completely immune, protected against subsequent tumor development.

Increased Survival of Mice Treated with the B16-F10-B7.1-IFNγ/β Cell Vaccine Before Challenge by Injection with $1 \times 10^6$ Live B16-F10-B7.1 Cells The previous Example determined that the B16-F10/B7.1/IFNγ/β and B16-F10/4-1BBL/B7.1/IFNγ/β vaccines were able to produce anti-tumor immune responses that resulted in tumor cell rejection. To further test the nature of the immune responses in similarly vaccinated mice, but challenged with a greater tumor burden, twice the number of live B16-F10/B7.1 cells ($1 \times 10^6$) were injected and tumor growth was monitored (FIG. 18C). These mice were treated according to Protocol 2 given that the highest % activated CD8+ T cell populations was produced in these mice, as evidenced by the results from FIGS. 12 and 13B.

Mice vaccinated with the B16-F10/4-1BBL/B7.1/IFNγ/β cells survived significantly longer than the control, unvaccinated mice (p=0.0005), with 50% of the vaccinated mice surviving the live tumor challenge (FIG. 18C). The B16-F10/B7.1/IFNγ/β vaccinated mice also showed improved survival outcomes and were completely protected against tumor development (p=0.0096). The difference in survival between the two groups of mice receiving either of the two different anticancer vaccines did not reach statistical significance in these studies.

CD8+ T Cell Responses Produced in Mice Treated with Four Doses of the B16-F10-4-1BBL-B7.1-IFNγ/β Anticancer Vaccine Before Challenge With a Live Melanoma Cell Burden Previously developed vaccines have been unable to prevent the formation of tumors when the vaccinated mice were subsequently challenged with live B16-F10 cells, as these are the most aggressive and fastest growing of all of the B16-F10 variants, as confirmed in the present study (FIG. 22). To further test the anti-tumor immune responses produced in response to either the B16-F10/B7.1/IFNγ/β or B16-F10/4-1BBL/B7.1/IFNγ/β cell vaccines, mice receiving either one of these anticancer vaccines were challenged with $5 \times 10^5$ live wild type B16-F10 cells (FIG. 19).

All mice were sacrificed 17 days after challenge by injection with the live wild type B16-F10 cells because tumor measurements had reached maximum allowable dimensions as per the animal ethics guidelines. FIG. 19A shows that all mice, irrespectively of whether they were vaccinated or not, developed tumors. The analysis determined that despite all mice developing tumors, the size of tumors on B16-F10/4-1BBL/B7.1/IFNγ/β vaccinated mice were significantly smaller than tumors on either the B16-F10/B7.1/IFNγ/β vaccinated mice (p=0.019) or the unvaccinated, control mice (p=0.002).

After initial measurements were recorded, tumors and spleens were harvested and weighed as shown in FIGS. 19B and C. Next, spleens, blood, lymph nodes and tumors were processed and analysed for their $CD4^+$ and $CD8^+$ T cell and regulatory T cell populations by flow cytometry (FIG. 20).

The results showed no difference in the weight of either tumors or spleens between mice in any of the treatment groups (FIGS. 19C and D). However, the mean weight of tumors from the B16-F10/4-1BBL/B7.1/IFNγ/β vaccinated mice was smaller than that of the other groups, consistent with the data shown in FIG. 19A comparing the differences measured in physical sizes of the tumors.

Significant differences were noted particularly in the $CD8^+$ T cell populations within the spleen and tumor samples. Thus, significantly higher % $CD8^+$ T cells were found in the spleens from the B16-F10/4-1BBL/B7.1/IFNγ/β vaccinated mice compared with either control (p=0.041) or the B16-F10/B7.1/IFNγ/β vaccinated mice (p=0.018; FIG. 20A). Similarly, the mean % $CD8^+$ T cells in the blood of B16-F10/4-1BBL/B7.1/IFNγ/β vaccinated mice was higher than both other groups, although this increase was not statistically significant (FIG. 20B). Furthermore, the B16-F10/4-1BBL/B7.1/IFNγ/β vaccinated mice were found to produce significantly higher % $CD8^+$ T cells within the tumors compared to control, unvaccinated mice (p=0.002) as shown in FIG. 20D.

Only minor changes in the % $CD4^+$ and regulatory T cell populations were observed. However, the blood of B16-F10/4-1BBL/B7.1/IFNγ/β vaccinated mice was found to produce a slightly higher % regulatory T cells than the levels in the blood of the control, unvaccinated mice (p=0.005) or the B16-F10/B7.1/IFNγ/β vaccinated mice (p=0.006) as shown in FIG. 20B.

Enhanced Survival of Mice Receiving Four Doses of the B16-F10-4-1BBL-B7.1-IFNγ/β Vaccine Before Challenge a Lower Dose of Live B16-F10 Cells Following on from the previous experiment involving challenging mice with the live wild type B16-F10 cells, the next experiment involved comparing the growth of tumors in unvaccinated mice to mice receiving four doses of the B16-F10/4-1BBL/B7.1/IFNγ/β anticancer vaccine before challenge by injecting with 10-fold less B16-F10 cells ($5 \times 10^4$ B16-F10 cells). The aim of this experiment was to determine whether using a smaller number of live tumor cells has an effect on the length of time the mice are able to survive before they were required to be euthanized (FIG. 21A).

The difference in length of survival between the unvaccinated, control mice versus the B16-F10/4-1BBL/B7.1/IFNγ/β vaccinated mice after challenge with live cancer cells was determined to be statistically significant (p=0.0058). All unvaccinated, challenged mice had to be euthanized within 21 days after the injection with the live tumor cells (FIG. 17A). As the B16-F10 cell line is an aggressive and rapidly growing cell line, these mice were only able to survive an extra four to five days compared to the day 17 euthanasia of the control mice that had been challenged with 10 times more B16-F10 cells, as shown in FIG. 19A. In addition, one out of the four mice administered with the B16-F10/4-1BBL/B7.1/IFNγ/β cell vaccine resulted in a protective anti-tumor response as it did not develop a tumor. Furthermore, the three vaccinated mice that did develop tumors survived, on average, an additional 10 days longer than the unvaccinated, challenged mice before their tumors reached maximum dimensions and required euthanizing.

Example 5

T Cell Levels Produced in Mice Receiving Differing Vaccine Doses and that Remained Tumor Free after Live Tumor Challenge This Example follows on from the experiments described above and embodied in FIG. 17B which showed that a number of mice vaccinated with two doses of any of the three different anti-cancer vaccines did not form tumors after challenge with $5 \times 10^5$ live B16-F10/B7.1 cells. The aim of this Example was to analyse $CD4^+$ and $CD8^+$ T cell populations in tissue samples from the surviving mice and identify the memory T cells as either effector memory ($T_{EM}$) or central memory ($T_{CM}$) $CD8^+$ T cells present within the samples.

The vaccinated mice that remained tumor free for at least 112 days following injection with live tumor cells were given two more booster injections of the anti-cancer cell vaccine before re-challenge with a live tumor cell burden. The unvaccinated mice were also challenged with live tumor cells or remained untreated. Spleens were collected from all mice and weighed as shown in FIG. 21B before the blood, spleen and lymph nodes were processed and analysed for changes in $CD4^+$ and $CD8^+$ T cell populations (FIG. 22). Concurrently, the $CD8^+$ T cell populations were further analysed for the presence or absence of the memory T cell molecules, CD62L and CCR7, by flow cytometry in order to identify the $T_{EM}$ and $T_{CM}$ cell subpopulations (FIG. 23).

Analysis of the spleen weight data in FIG. 21B showed that there was a significant difference between the groups (p=0.007). Further analysis determined that mice vaccinated with the B16-F10/B7.1/IFNγ/β cell vaccine had significantly heavier spleens than either the control, unvaccinated mice (p=0.004), unvaccinated mice that were challenged with live tumor cells (p=0.002) or mice treated with the B16-F10/4-1BBL/B7.1/IFNγ/β cell vaccine (p=0.004). Importantly, the unvaccinated mice that had been injected with live tumor cells were the only mice to develop tumors, as detected on the day the animals were euthanized. The average dimensions of the tumors that developed on unvaccinated and challenged mice were 6×4.5 mm. None of the mice that had previously been vaccinated before challenge with live melanoma cells proceeded to develop tumors.

A significant intergroup variation was detected when analysing the CD8$^+$ T cells produced within the spleens of mice in all the treated groups (p<0.0001; FIG. 22A). Post hoc testing showed that the % CD8$^+$ T cell population produced in the spleens from the B16-F10/4-1BBL/B7.1/IFNγ/β vaccinated mice was significantly increased when compared to all other treated groups. The same observation was made when analysing the % CD8$^+$ T cell populations in the blood of these B16-F10/4-1BBL/B7.1/IFNγ/β vaccinated mice (FIG. 22B). By comparison, lower % CD4$^+$ T cell populations were observed in the lymph nodes of all groups of vaccinated mice when compared to control, unvaccinated mice or unvaccinated mice that had been challenged with live tumor cells (FIG. 22C).

When the $T_{EM}$ populations were analysed as a subset of the CD8$^+$ T cell population, the spleen and blood from all vaccinated mice had significantly elevated populations over that of either the control, unvaccinated mice or the unvaccinated mice challenged with live tumor cells. Furthermore, the spleens of B16-F10/4-1BBL/B7.1/IFNγ/β vaccinated mice produced the highest mean % $T_{EM}$ cell population, significantly greater than that of either the control, unvaccinated mice, unvaccinated mice challenged with live tumor cells or the B16-F10-B7.1-IFNγ/β vaccinated mice (FIG. 23A). The blood of B16-F10/4-1BBL/B7.1/IFNγ/β vaccinated mice was also found to contain the highest % $T_{EM}$ cell population, which was again significantly greater than that of either the control, unvaccinated mice, unvaccinated mice challenged with live tumor cells (p<0.00022) or the B16-F10/B7.1/IFNγ/β vaccinated mice (p=0.049; FIG. 23B). The only difference in TCM cell populations was found in the lymph nodes of B16-F10-4/1BBL/B7.1/IFNγ/β vaccinated mice, where the % $T_{CM}$ cells was slightly higher than the levels in the lymph nodes of the control, unvaccinated mice (p=0.004) (FIG. 23C).

Highly elevated % CD8+ and TEM cells produced in mice treated with four doses of the B16-F10/4-1BBL/B7.1/IFNγ/β cell vaccine that remained tumor free after challenge with live tumor cells This section follows on from the Example embodied in FIG. 18, which indicated that a number of mice vaccinated with four doses of any of the three vaccine cell lines (using vaccination Protocol 2) did not form tumors after being challenged on two separate occasions with 5×10$^5$ live B16-F10/B7.1 cells. Thus, the mice remained tumor free for at least 190 days before they were then boosted with an additional 2 doses of vaccine and re-challenged with 5×10$^5$ live B16-F10/B7.1 cells. Spleens were collected from the vaccinated and control mice 6 days after the injection of live tumor cells and their weights were recorded (FIG. 24A). The lymphocytes were then purified from the spleen, blood and lymph nodes and analysed for any differences in % CD4$^+$ and CD8$^+$ T cell populations by flow cytometry. The CD8$^+$ T cell populations were further analysed for the presence or absence of memory T cell markers used to identify $T_{EM}$ and $T_{CM}$ cell subpopulations by flow cytometry.

The analysis of spleen weights showed that a significant difference was present between the treated groups and control mice (p=0.004; FIG. 24A). All of the vaccinated mice were determined to have significantly heavier spleens than the control, unvaccinated mice. B16-F10/4-1BBL/B7.1/IFNγ/β vaccinated mice were found to have the heaviest average spleen weight, which was significantly heavier than the control, unvaccinated mice (p=0.0004) or that of the unvaccinated mice that had been injected with the live tumor cells (p=0.024).

A significant difference in the CD4$^+$ T cell populations within the spleens was detected between the treatment groups (p=0.0013; FIG. 24B). B16-F10/4-1BBL/B7.1/IFNγ/β vaccinated mice were shown to produce the lowest % CD4$^+$ T cells in the spleen, which was significantly lower than the CD4$^+$ values of either the control (p=0.0034), the non-vaccinated mice challenged with live tumor cells (p=0.0001) or the B16-F10/4-1BBL/IFNγ/β vaccinated mice (p=0.022). Furthermore, the % CD4$^+$ T cell populations produced in the blood and lymph nodes of all vaccinated mice were found to be lower than the levels produced in control, untreated mice or the non-vaccinated mice challenged with live tumor cells (FIGS. 24C and D).

In contrast, significantly elevated % CD8$^+$ T cell populations were produced in both the spleen and blood of the B16-F10/4-1BBL/B7.1/IFNγ/β vaccinated mice when compared to all other groups of mice (p<0.0027; FIGS. 24B and C). In addition, the mean % CD8$^+$ T cells produced in the lymph nodes of all vaccinated mice were greater than the values of either the control, untreated mice or the non-vaccinated mice challenged with live tumor cells (FIG. 24D).

Analysis of $T_{EM}$ cells within the spleen (p<0.0001), blood (p<0.0001) and lymph nodes (p=0.002) were all determined to vary significantly between the treatment groups as shown in FIG. 25. Significantly higher % $T_{EM}$ cells were detected in the spleen and blood of all of the vaccinated groups of mice compared to the control, untreated mice. However, the most significant increases in % $T_{EM}$ cells were produced in the samples from the B16-F10/4-1BBL/B7.1/IFNγ/β vaccinated mice compared to all other groups of mice with 75% and 87% of CD8$^+$ T cells in the spleen and blood respectively, identified as $T_{EM}$ cells. Furthermore, the B16-F10/4-1BBL/B7.1/IFNγ/β vaccinated mice were the only group to have significantly elevated % $T_{EM}$ cells in their lymph nodes and this population was highly elevated compared to the % $T_{EM}$ cell populations in the lymph nodes of all the other groups of mice (FIG. 25C).

Example 6

LT$_A$$^{-/-}$ Mice Injected with the B16-F10-4-1BBL-B37.1-IFNγ/β Vaccine Generated Enhanced CD8$^+$ T Cell Responses in the Absence of Dendritic Cells This Example assesses whether the inclusion on 4-1BBL onto the B7.1 expressing melanoma vaccine, in the form of B16-F10/4-1BBL/B7.1/IFNγ/β vaccine cells, is able to elicit a CD8$^+$ T cell immune response without any co-stimulatory activity provided by dendritic cells (DCs). This was achieved by characterizing the immune response of LTα−/− mice treated with either the B16-F10/4-1BBL/B7.1/IFNγ/β or B16-F10/B7.1/IFNγ/β vaccine.

Following vaccination, LTα−/− mice treated with the B16-F10/4-1BBL/B7.1/IFNγ/β vaccine had significantly heavier spleens compared to unvaccinated mice (p=0.002) and mice treated with the B16-F10/B7.1/IFNγ/β vaccine (p=0.022; FIG. 26A). Increased % CD8+ T and decreased % CD4+ T cell populations were produced in the spleens from B16-F10/4-1BBL/B7.1/IFNγ/β vaccinated LTα$^{-/-}$ mice compared to control or B16-F10/B7.1/IFNγ/β vaccinated mice (FIG. 26B). B16-F10/4-1BBL/B7.1/IFNγ/β vaccinated mice also displayed an increased % CD8+ T cell population in peripheral blood compared to control mice but at borderline significance (p=0.057; FIG. 26C).

Next, splenic lymphocytes from control and vaccinated LTα-/- mice were subjected to antigenic stimulation in MLCs. CD8+ T cells derived from B16-F10/4-1BBL/B7.1/IFNγ/β vaccinated LTα$^{-/-}$ mice were effectively expanded in MLCs displaying a significantly increased % CD8+ T cell population compared to populations produced from either control (p=0.003) or B16-F10/B7.1/IFNγ/β vaccinated mice (p=0.048; FIG. 27A). Subsequently, 39% of the CD8+ T cells in MLCs derived from B16-F10/4-1BBL/B7.1/IFNγ/β vaccinated LTα$^{-/-}$ mice were characterised as activated, which was more than 4-fold higher than the population obtained from MLCs derived from unvaccinated animals (FIG. 27B).

CTL analysis using splenic lymphocytes cultured in MLC determined that lymphocytes derived from B16-F10/4-1BBL/B7.1/IFNγ/β vaccinated LTα$^{-/-}$ mice induced the highest proportion of cell death, which was significantly greater than the CTL assays from either the unvaccinated or B16-F10/B7.1/IFNγ/β vaccinated LTα$^{-/-}$ mice (p<0.001; FIG. 27C). Furthermore, lymphocytes from B16-F10/4-1BBL/B7.1/IFNγ/β vaccinated mice were able to generate a 5.63-fold increase in lytic units per effector cell population compared to lymphocytes from control mice.

The vaccines were then assessed for their ability to stimulate T cell responses in vivo by challenging vaccinated LTα$^{-/-}$ mice with live tumour cells. 75% of B16-F10/B7.1/IFNγ/β vaccinated LTα$^{-/-}$ mice survived the live tumour challenge for a period of 60 days and 67% of B16-F10/4-1BBL/B7.1/IFNγ/β vaccinated mice survived the tumour challenge for a total of 131 days, both of which were significantly longer than unvaccinated control mice (p=0.001, and p<0.001 for B16-F10/B7.1/IFNγ/β and B16-F10/4-1BBL/B7.1/IFNγ/β respectively; data not shown). The long-lived anti-tumour response generated in the B16-F10/4-1BBL/B7.1/IFNγ/β vaccinated mice was then characterised following boosting and re-challenging with tumour cells. Initial spleen weights and T cell analyses suggested that immune responses were not altered in vaccinated mice compared to unvaccinated mice as no differences were detected between the groups in terms of spleen weights and % splenic CD8+ T cell populations (FIG. 28A, B). A higher mean % CD8+ T cell population was detected within the peripheral blood of B16-F10/4-1BBL/B7.1/IFNγ/β vaccinated LTα-/- mice, however this difference was only significantly higher than unvaccinated mice that had been injected with live tumour cells (FIG. 28C). More interestingly, when the CD8+ T cell populations were assessed for $T_{EM}$ and $T_{CM}$ subpopulations, 45% of splenic T cells (FIG. 28D) and 60% of peripheral blood T cells (FIG. 28E) were classified as $T_{EM}$ CD8+ T cells. These subpopulations were significantly elevated compared to unvaccinated mice and unvaccinated, tumour bearing mice, indicating that vaccination was able to induce potent memory responses to previously encountered antigens.

Example 7

Optimization of IFN Treatment to Upregulate H-2K$^B$ Expression on the B16-F10 Cell Surface of the Immunomodulatory Preparation In addition to expressing high levels of B7 and/or 4-1BBL, for immunotherapeutic purposes it is beneficial that the cells also express elevated levels of the class I MHC molecule H-2K$^b$ on the cell surface to increase the possibility of antigenic presentation. Significantly, the level of H-2K$^b$ was enhanced by treating the cells with a combination of IFNγ and IFNβ, as assessed using flow cytometry by immunostaining with an FITC-conjugated anti-mouse H-2K$^b$ antibody.

As previously described, cells were treated with each IFN alone and in combination (i.e., IFNγ and IFNβ) before comparing the level of H-2K$^b$ expression on the cell surface. The data in Table 1 show the effect of treating B16-F10 and B16-F10/4-1BBL with IFNγ for 44 hours, with IFNβ for 20 hours or by priming with IFNγ for 44 hours before treating with IFNβ for a further 20 hours. It was found that by further extending the lengths of IFN treatment significantly reduced cell yields and viability (data not shown).

B16-F10 cells treated with either IFNγ alone or IFNβ alone can upregulate MHC class I expression on the cell surface by 11- and 10-fold respectively. Furthermore, B16-F10/4-1BBL cells also exhibit upregulated MHC class I expression after treatment with each IFN individually. However, the B16-F10/4-1BBL cells were shown to be more responsive to IFNγ and less responsive to IFNβ (see, Table 7). Although the wild-type and subline cells exhibit differing responses to each IFN alone, both cell lines showed most significant up-regulation of MHC when a combination of both IFNγ and IFNβ were administered. The overall level of MHC class I expression on the B16-F10/4-1BBL cells was 28-fold greater than the expression on isotype stained cells.

To determine whether the expression of MHC class I could be further increased on the B16-F10/4-1BBL cells, higher concentrations of the IFNγ and IFNβ were also tested. FIG. 29 displays histograms from flow cytometric analysis produced after treating the B16-F10/4-1BBL sort 1 cells with 1000, 2000, or 3000 IU/mL of IFNγ alone or IFNβ. The level of H-2K$^b$ expressed on the B16-F10/4-1BBL cells did not show any further change after treating with increasing concentrations of either IFNγ and/or IFNβ as shown in FIG. 29. Therefore, it was concluded that 1000 IU/mL of IFNγ and IFNβ would be used to treat all vaccine cell lines as this combination synergistically upregulated H-2K$^b$ expression as effectively as when more IFN was used.

TABLE 7

Combined treatment with IFNγ/β increased H-2K$^b$ expression on B16-F10 melanoma cell lines

| Sample | Fold increase compared to isotype control |
| --- | --- |
| B16-F10 | 1 |
| B16-F10/4-1BBL | 1 |
| B16-F10 + IFNγ | 11 |
| B16-F10 + IFNβ | 10 |
| B16-F10 + IFNγ/β | 23 |
| B16-F10/4-1BBL + IFNγ | 25 |
| B16-F10/4-1BBL + IFNβ | 6 |
| B16-F10/4-1BBL + IFNγ/β | 28 |

Example 8

Analysis of Vaccine Preparations for H-2K$^B$, B7.1 and 4-1BBL Co-Expression Use of a BD LSRFortessa flow cytometer allows for a high efficiency signal detection of PC-conjugated antibodies, with an excitation wavelength of 566 nm and an emission wavelength of 576 nm (as the LSRFortessa flow cytometer uses a 561 nm green laser for exciting PE, compared to the 588 nm blue laser which is present in the BD FACSCalibur machine). Some cell surface marker analyses were performed on both machines, and hence, these have been included for comparison as shown in Table 8.

All of the cell lines analysed showed highly upregulated levels of H-2K$^b$ on the cell surface as quantitated using both the FACSCalibur and LSRFortessa when compared to isotype stained samples. The three vaccine cell lines analysed on the FACSCalibur were shown to have similar levels of H-2K$^b$ expression compared to wild-type B16-F10 cells. In comparison, the three immunomodulatory cell lines had a greater fold increase in their H-2K$^b$ expression as compared to wild-type B16-F10 cells, when assessed using the LSR-Fortessa. The 4-1BBL and B7.1 expression levels were also analysed on the cells using both flow cytometers. The B7.1 and 4-1BBL expression data generated using the LSR-Fortessa again showed greater fold increases, which indicated that the LSRFortessa was more sensitive and displayed a higher efficiency for detecting the fluorescence signals.

TABLE 8

Comparison of H-2Kb, B7.1 and 4-1BBL expression on B16-F10 wild-type and sublines detected using the FACSCalibur and LSRFortessa flow cytometers.

| Cell Line | FACSCalibur Untreated | FACSCalibur IFNγ/β | LSRFortessa Untreated | LSRFortessa IFNγ/β |
|---|---|---|---|---|
| B16-F10: | | | | |
| MHC Class I | 1 | 22 | | 17 |
| B7.1 | 1 | | | |
| 4-1BBL | 3 | | | |
| B16-F10-4-1BBL sort 1: | | | | |
| MHC Class I | 1 | 24 | | 39 |
| 4-1BBL | 1104 | | 2119 | 817 |
| B16-F10-B7.1 sort 3, clone 3: | | | | |
| MHC Class I | | 18 | | 26 |
| B7.1 | 24 | | 60 | 49 |
| B16-F10-4-1BBL-B7.1 sort 5, clone 1: | | | | |
| MHC Class I | | 24 | | 36 |
| B7.1 | 49 | | 121 | 91 |
| 4-1BBL | 465 | | 2329 | 668 |

All fold increase values in co-stimulatory molecule expression are shown relative to the values of isotype stained samples (i.e., above background of same sample).

Materials and Methods

General Flow Cytometry Protocols

For all immunofluorescent staining procedures cells were washed and stained in staining medium, which comprised 2% FCS in 1×PBS. For the staining steps, cells were routinely resuspended in 100 µL of staining medium before antibodies were added. In addition to immunofluorescently stained samples, unstained and isotype matched samples were also prepared and analysed for comparison purposes. The equation below was used in order to calculate the factor increase in the level of cell surface marker expression by subtracting the mean fluorescent intensity (MFI) of an unstained sample from that of an antibody (Ab) stained sample. FCS Express and FACS Diva software programs were used to analyse data produced from both the FACSCalibur and LSRFortessa flow cytometers.

$$\text{Factor Increase} = \frac{MFI\ (Ab\ \text{stained cells}) - MFI\ (\text{isotype stained cells})}{MFI\ (\text{unstained cells}) - MFI\ (\text{isotype stained cells})}$$

Analysis of Immune Stimulatory Cell Surface Molecules on Vaccine Cells

Transfection efficiency was determined by staining B16-F10 sublines with antibodies to detect the cell surface markers, B7.1 and 4-1BBL. Cells were detached from their culture vessel and washed with staining medium. To detect for the presence of 4-1BBL on the cells, a PE-conjugated anti-mouse 4-1BBL antibody was used at a concentration of 1 µg per 1×10$^6$ cells in 100 µL of staining medium. To detect for the presence of B7.1 on the cells, a PE-conjugated anti-mouse CD80 antibody was used at a concentration of 0.2 µg per 1×10$^6$ cells in 100 µL of staining medium. A PE-conjugated rat IgG2a isotype matched antibody was used to stain samples that were used as isotype controls. The presence of both of these cell surface molecules were detected using either flow cytometer. To confirm whether the cells expressing 4-1BBL actually expressed a functional and intact 4-1BBL molecule, cells were incubated with a recombinant mouse 4-1BB/Fc chimera primary antibody. The 4-1BB/Fc chimera is the receptor for the 4-1BBL. In order to detect whether the primary antibody bound to 4-1BBL, a PE-conjugated goat anti-human IgG Fcγ fragment specific antibody that also exhibited cross-reactivity with the mouse antigen was added and then analysed on the BD FACSCalibur flow cytometer. To detect for upregulated levels of H-2K$^b$ on IFN treated cells, the cells were stained with an FITC-conjugated anti-mouse H-2K$^b$ Ab at a concentration of 2.5 µg per 1×10$^6$ cells in 100 µL of staining medium.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

REFERENCES

Berd, D., Maguire, H. C., Jr., Schuchter, L. M., Hamilton, R., Hauck, W. W., Sato, T. and Mastrangelo, M. J., Autologous hapten-modified melanoma vaccine as post-surgical adjuvant treatment after resection of nodal metastases, *J Clin Oncol,* 1997, 15(6): 2359-70.

Bray, F., Jemal, A., Grey, N., Ferlay, J., Forman, D., Global cancer transitions according to the Human Development Index (2008-2030): a population-based study, *Lancet Oncol.,* 2012, 13(8): 790-801.

de Rosa, F., Ridolfi L., Ridolfi R., Gentili G., Valmorri L., Nanni O., Petrini M., Fiammenghi L., Granato A. M., Ancarani V., Pancisi E., Soldati V., Cassan S., Riccobon A., Parisi E., Romeo A., Turci L., Guidoboni M., Vaccination with autologous dendritic cells loaded with autologous tumor lysate or homogenate combined with immunomodulating radiotherapy and/or preleukapheresis IFN-α in patients with metastatic melanoma: a randomised "proof-of-principle" phase II study, *J Transl Med,* 2014, 12: 209.

Dezfouli, S., Hatzinisiriou, I. and Ralph, S. J., Enhancing CTL responses to melanoma cell vaccines in vivo: synergistic increases obtained using IFNgamma primed and IFNbeta treated B7-1+B16-F10 melanoma cells, *Immunol Cell Biol,* 2003, 81(6): 459-71.

Fang, L., Lonsdorf, A. S., Hwang, S. T., Immunotherapy for advanced melanoma, *J Invest Dermatol,* 2008, 128(11): 2596-605.

Faries, M. B., Hsueh, E. C., Ye, X., Hoban, M. and Morton, D. L., Effect of granulocyte/macrophage colony-stimulating factor on vaccination with an allogeneic whole-cell melanoma vaccine, *Clin Cancer Res,* 2009, 15(22): 7029-35.

Hsueh, E. C. and Morton, D. L., Antigen-based immunotherapy of melanoma: Canvaxin therapeutic polyvalent cancer vaccine, *Semin Cancer Biol,* 13(6): 401-7.

Jaffee, E. M., Hruban, R. H., Biedrzycki, B., Laheru, D., Schepers, K., Sauter, P. R., Goemann, M., Coleman, J., Grochow, L., Donehower, R. C., Lillemoe, K. D., O'Reilly, S., Abrams, R. A., Pardoll, D. M., Cameron, J. L. and Yeo, C. J., Novel allogeneic granulocyte-macrophage colony-stimulating factor-secreting tumor vaccine for pancreatic cancer: a phase I trial of safety and immune activation, 2001, *J Clin Oncol,* 19(1): 145-56.

Jemal, A., Saraiya, M., Patel, P., Cherala, S. S., Barnholtz-Sloan, J., Kim, J., Wiggins, C. L., Wingo, P. A., Recent trends in cutaneous melanoma incidence and death rates in the United States, 1992-2006, *J Am Acad Dermatol,* 2011, 65(5 Suppl 1): 517-25. e1-3.

Lotem, M., Kadouri, L., Merims, S., Ospovat, I., Nissan, A., Ron, I., Frankenburg, S., Machlenkin, A., Israel, S., Steinberg, H., Hamburger, T. and Peretz, T., HLA-B35 correlates with a favorable outcome following adjuvant administration of an HLA-matched allogeneic melanoma vaccine, *Tissue Antigens,* 2011, 78(3): 203-7.

Macatonia, S. E., Patterson, S., Knight, S. C., Suppression of immune responses by dendritic cells infected with HIV, *Immunology,* 1989, 67(3): 285-9, Macatonia, S. E., Lau, R., Patterson, A., Piching, A. J., Knight, S. C., Dendritic cell infection, depletion and dysfunction in HIV-infected individuals, *Immunology,* 1990, 71: 38-45.

O'Rourke, M. G., Johnson, M., Lanagan, C., See, J., Yang, J., Bell, J. R., Slater, G. J., Kerr, B. M., Crowe, B., Purdie, D. M., Elliott, S. L., Ellem, K. A. and Schmidt, C. W., Durable complete clinical responses in a phase I/II trial using an autologous melanoma cell/dendritic cell vaccine, *Cancer Immunol Immunother,* 2003, 52(6): 387-95.

Ralph, S. J., An update on malignant melanoma vaccine research: insights into mechanisms for improving the design and potency of melanoma therapeutic vaccines, *Am J Clin Dermatol,* 2007, 8(3): 123-41.

Soiffer, R., Hodi, F. S., Haluska, F., Jung, K., Gillessen, S., Singer, S., Tanabe, K., Duda, R., Mentzer, S., Jaklitsch, M., Bueno, R., Clift, S., Hardy, S., Neuberg, D., Mulligan, R., Webb, I., Mihm, M. and Dranoff, G., Vaccination with irradiated, autologous melanoma cells engineered to secrete granulocyte-macrophage colony-stimulating factor by adenoviral-mediated gene transfer augments antitumor immunity in patients with metastatic melanoma, *J Clin Oncol,* 2003, 21(17), 3343-50.

Sondak, V. K., Sabel, M. S. and Mule, J. J., Allogeneic and autologous melanoma vaccines: where have we been and where are we going?, *Clin Cancer Res,* 2006, 12(7 Pt 2): 2337s-2341s.

Trotter, A. S., Sroa, N., Weinkelmann, R. R., Olencki, T., Bechtel, M., A global review of melanoma follow-up guidelines. *J Clin Aesth Derm,* 2014, 6(9): 18-26.

Yang, J. C., Melanoma vaccines, *Cancer J,* 2011, 17(5): 277-82. 27693537

What is claimed is:

1. A composition comprising a B7 molecule, a 4-1BB agonist and animal cancer or tumor cells, said animal cancer or tumor cells having been contacted with at least one exogenous interferon (IFN) for a time and under conditions sufficient to enhance the antigen presenting function of the cells, wherein
   the B7 molecule is a B7.1 or B7.2 molecule;
   the exogenous IFN is not produced by the animal cancer or tumor cells; and
   the animal cancer or tumor cells have been washed to remove the at least one exogenous IFN.

2. A method for enhancing an immune response to a target cancer or tumor antigen in a subject, the method comprising administering to the subject an effective amount of a composition according to claim 1.

3. The method of claim 2, wherein the subject's antigen-presenting cells are depleted or reduced in number.

4. The method of claim 3, wherein the antigen-presenting cells that are depleted or reduced in number are macrophages, dendritic cells and/or B-cells.

5. The method of claim 3, further comprising exposing the subject to an immunosuppressive treatment.

6. The composition of claim 1, wherein the B7 molecule is a B7.1 molecule.

7. The composition of claim 1, wherein the B7 molecule is expressed on the surface of the cells, wherein at least a portion of the molecule is exposed to the extracellular environment.

8. The composition of claim 1, wherein the B7 molecule is present in soluble form.

9. The composition of claim 8, wherein the B7 molecule is a chimeric protein comprising a polypeptide comprising the extracellular domain of a B7 molecule fused or otherwise linked to an immunoglobulin constant region.

10. The composition of claim 1, wherein the 4-1BB agonist is expressed on the surface of the cells, wherein at least a portion of the molecule is exposed to the extracellular environment.

11. The composition of claim 1, wherein the 4-1BB agonist is present in soluble form.

12. The composition of claim 11, wherein the soluble 4-1BB agonist is a chimeric protein comprising a polypeptide comprising the extracellular domain of 4-1BBL fused or otherwise linked to an immunoglobulin constant region.

13. The composition of claim 1, wherein the 4-1BB agonist is a 4-1BBL molecule.

14. The composition of claim 1, wherein the animal cancer or tumor cells are derived from a tissue, organ or system selected from the group consisting of lung, breast, uterus, cervix, ovaries, colon, pancreas, prostate, testes, stomach, bladder, kidney, bone, liver, the reticuloendothelial system, esophagus, brain, skin, and soft tissue.

15. The composition of claim 1, wherein the animal cancer or tumor cells are melanoma cells.

16. The composition of claim 1, wherein the cells have been contacted with an IFNγ and optionally one or both of a first type I IFN and a second type I IFN, wherein the first type I IFN is an IFNβ, and wherein the second type I interferon is an IFNα.

17. A pharmaceutical composition comprising the composition of claim 1, together with a pharmaceutically acceptable carrier, diluent or excipient.

18. An immune-potentiating composition comprising the composition of claim 1, and a pharmaceutically acceptable adjuvant.

19. The immune-potentiating composition of claim 18, wherein the adjuvant is selected from the group consisting of TGF-beta inhibitors, galectin inhibitors and monoclonal antibodies against immunosuppressive inhibitors, wherein the immunosuppressive inhibitors are selected from the group consisting of CTLA4, PD1, PD-L1 and indole dioxygenase (IDO).

20. The composition of claim 1, wherein the cells have been cultured in the presence of IFNγ from about 16 to about 96 hours and subsequently cultured in the presence of one or more type I IFNβ and/or IFNα from about 16 to about 72 hours.

21. The composition of claim 20, wherein the IFNγ is present in the culture medium at a concentration of about 100 to about 2000 international units/mL and wherein the IFNβ and/or IFNα is present in the culture medium at a concentration of about 100 to about 2000 international units/mL.

* * * * *

SEQUENCE LISTING

```
<160> NUMBER OF SEQ ID NOS: 7

<210> SEQ ID NO 1
<211> LENGTH: 288
<212> TYPE: PRT
<213> ORGANISM: Homo sapiens

<400> SEQUENCE: 1

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80
```

-continued

```
Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 2
<211> LENGTH: 329
<212> TYPE: PRT
<213> ORGANISM: Homo sapiens

<400> SEQUENCE: 2

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
```

```
            165                 170                 175
Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
            195                 200                 205

Asp Val Thr Ser Asn Met Thr Ile Phe Cys Ile Leu Glu Thr Asp Lys
            210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
            245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
            275                 280                 285

Arg Glu Glu Ser Glu Gln Thr Lys Lys Arg Glu Lys Ile His Ile Pro
            290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
            325

<210> SEQ ID NO 3
<211> LENGTH: 254
<212> TYPE: PRT
<213> ORGANISM: Homo sapiens

<400> SEQUENCE: 3

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
            85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
            130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
            165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
            195                 200                 205
```

Gly Gln Arg Leu Gly Val His Leu His Thr Glu Ala Arg Ala Arg His
   210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 4
<211> LENGTH: 1680
<212> TYPE: DNA
<213> ORGANISM: Homo sapiens

<400> SEQUENCE: 4

```
aaaaagcggc gcgctgtgtc ttcccgcagt ctctcgtcat ggaatacgcc tctgacgctt      60
cactggaccc cgaagccccg tggcctcccg cgccccgcgc tcgcgcctgc cgcgtactgc     120
cttgggccct ggtcgcgggg ctgctgctgc tgctgctgct cgctgccgcc tgcgccgtct     180
tcctcgcctg ccctgggcc gtgtccgggg ctcgcgcctc gcccggctcc gcggccagcc     240
cgagactccg cgagggtccc gagctttcgc ccgacgatcc cgccggcctc ttggacctgc     300
ggcagggcat gtttgcgcag ctggtggccc aaaatgttct gctgatcgat gggccctga     360
gctggtacag tgacccaggc ctggcaggcg tgtccctgac gggggggcctg agctacaaag     420
aggacacgaa ggagctggtg gtggccaagg ctggagtcta ctatgtcttc tttcaactag     480
agctgcggcg cgtggtggcc ggcgagggct caggctccgt ttcacttgcg ctgcacctgc     540
agccactgcg ctctgctgct ggggccgccg ccctggcttt gaccgtggac ctgccacccg     600
cctcctccga ggctcggaac tcggccttcg gtttccaggg ccgcttgctg cacctgagtg     660
ccggccagcg cctgggcgtc atcttcaca ctgaggccag ggcacgccat gcctggcagc     720
ttacccaggg cgccacagtc ttgggactct tccgggtgac ccccgaaatc ccagccggac     780
tcccttcacc gaggtcggaa taacgtccag cctgggtgca gcccacctgg acagagtccg     840
aatcctactc catccttcat ggagacccct ggtgctgggt ccctgctgct ttctctacct     900
caagggcgctt ggcaggggtc cctgctgctg acctccccctt gaggaccctc ctcacccact     960
ccttccccaa gttggacctt gatatttatt ctgagcctga gctcagataa tatattatat    1020
atattatata tatatatata tttctatta aagaggatcc tgagtttgtg aatggacttt    1080
tttagaggag ttgttttggg gggggggggg tcttcgacat tgccgaggct ggtcttgaac    1140
tcctggactt agacgatcct cctgcctcag cctcccaagc aactgggatt catcctttct    1200
attaattcat tgtacttatt tgcttatttg tgtgtattga gcatctgtaa gtgccagca    1260
ttgtgcccag gctagggggc tatagaaaca tctagaaata gactgaaaga aaatctgagt    1320
tatggtaata cgtgaggaat ttaaagactc atccccagcc tccacctcct gtgtgatact    1380
tgggggctag cttttttctt tctttctttt ttttgagatg gtcttgttct gtcaaccagg    1440
ctagaatgca gcggtgcaat catgagtcaa tgcagcctcc agcctcgacc tcccgaggct    1500
caggtgatcc tcccatctca gcctctcgag tagctgggac cacagttgtg tgccaccaca    1560
cttggctaac tttttaattt ttttgcggag acggtattgc tatgttgcca aggttgttta    1620
catgccagta caattataa taaacactca ttttcctcc ctctgaaaaa aaaaaaaaaa    1680
```

<210> SEQ ID NO 5
<211> LENGTH: 166
<212> TYPE: PRT
<213> ORGANISM: Homo sapiens

<400> SEQUENCE: 5

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 6
<211> LENGTH: 187
<212> TYPE: PRT
<213> ORGANISM: Homo sapiens

<400> SEQUENCE: 6

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

```
<210> SEQ ID NO 7
<211> LENGTH: 212
<212> TYPE: PRT
<213> ORGANISM: Homo sapiens

<400> SEQUENCE: 7

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```